United States Patent
Vernejoul et al.

(10) Patent No.: US 9,567,336 B2
(45) Date of Patent: Feb. 14, 2017

(54) CONJUGATED TLR7 AND/OR TLR8 AND TLR2 AGONISTS

(71) Applicant: CAYLA, Toulouse (FR)

(72) Inventors: Fabienne Vernejoul, Toulouse (FR); Arnaud Debin, Escalquens (FR); Daniel Drocourt, Saint Orens de Gameville (FR); Eric Perouzel, Toulouse (FR); Gerard Tiraby, Toulouse (FR); Thierry Lioux, Balma (FR)

(73) Assignee: INVIVOGEN, Toulouse (FR)

( * ) Notice: Subject to any disclaimer, the term of this patent is extended or adjusted under 35 U.S.C. 154(b) by 736 days.

(21) Appl. No.: 13/832,179

(22) Filed: Mar. 15, 2013

(65) Prior Publication Data
US 2014/0141033 A1    May 22, 2014

Related U.S. Application Data

(60) Provisional application No. 61/727,832, filed on Nov. 19, 2012.

(30) Foreign Application Priority Data

Nov. 19, 2012 (EP) .................................... 12193250

(51) Int. Cl.
*A61K 31/52* (2006.01)
*A61K 31/7076* (2006.01)
*C07D 473/16* (2006.01)
*C07D 471/04* (2006.01)
*A61K 47/48* (2006.01)

(52) U.S. Cl.
CPC ............ *C07D 473/16* (2013.01); *A61K 47/481* (2013.01); *A61K 47/48046* (2013.01); *C07D 471/04* (2013.01)

(58) Field of Classification Search
CPC .. A61K 31/52; A61K 31/7076; C07D 473/16; C07D 471/04
See application file for complete search history.

(56) References Cited

U.S. PATENT DOCUMENTS

2011/0282061 A1   11/2011   Johnson
2012/0294885 A1   11/2012   David et al.

FOREIGN PATENT DOCUMENTS

WO   2009/088401 A2   7/2009

OTHER PUBLICATIONS

Dick RM (2011). "Chapter 2. Pharmacodynamics: The Study of Drug Action". In Ouellette R, Joyce JA. Pharmacology for Nurse Anesthesiology. Jones & Bartlett Learning: pp. 17-26.*
J. G. Cannon Chapter Nineteen in Burger's Medicinal Chemistry and Drug Discovery, Fifth Edition, vol. 1: Principles and Practice, Wiley-Interscience 1995, pp. 783-802.*
Anton Kaiser et al.: "Fully Synthetic Vaccines Consisting of Tumor-Associated MUC1 Glycopeptides and a Lipopeptide Ligand of the Toll-like Receptor 2", Angewandte Chemie International Edition, vol. 49, No. 21, May 10, 2010 (May 10, 2010), pp. 3688-3692, XP055050831, ISSN : 1433-7851, 001: 10.1002/anie.201000462, abstract.
Zeng W et al.: "Lipidation of intact proteins produces highly immunogenic vaccine candidates", Molecular Immunology, Pergamon, GB, vol. 48, No. 4, Jan. 1, 2011 (Jan. 1, 2011), pp. 490-496, XP027578517, ISSN: 0161-5890 [retrieved on Dec. 29, 2010], abstract.
Ghosh et al.: "TLR-TLR cross talk in human PBMC resulting in synergistic and antagonistic regulation of type-1 and 2 interferons, IL-12 and TNF-alpha", International Immunopharmacology, Elsevier, Amsterdam, NL, vol. 7, No. 8, Jun. 11, 2007 (Jun. 11, 2007), pp. 1111-1121, XP022113162, ISSN: 1567-5769, 001: 10.1016/J. INTIMP.2007.04.006 * p. 1119, col. 1, paragraph 1-p. 1120, col. 1, paragraph 1.
M. H. Wenink et al.: "TLR2 Promotes 1-23 Th2/Th17 Responses via TLR4 and TLR7/8 by Abrogating the Type I IFN Amplification Loop", The Journal of Immunology, vol. 183, No. 11, Nov. 13, 2009 (Nov. 13, 2009), pp. 6960-6970, XP055050689, ISSN: 0022-1767, 001: 10.4049/jimmunol.0900713 * abstract *.
Y. C. Liu et al.: "TLR2 Signaling Depletes IRAK1 and Inhibits Induction of Type I IFNby TLR7/9", The Journal of Immunology, vol. 188, No. 3, Jan. 6, 2012 (Jan. 6, 2012), pp. 1019-1026, XP055050692, ISSN: 0022-1767, 001: 10.4049/jimmunol. 1102181 * abstract.
European Search Report, dated Jan. 30, 2013, from corresponding European application.

* cited by examiner

Primary Examiner — Jeffrey S Lundgren
Assistant Examiner — Chris Simmons
(74) Attorney, Agent, or Firm — Young & Thompson

(57) ABSTRACT

A conjugated compound of formula Q-Z—$R^4$ wherein Q is a TLR7 and/or TLR8 agonist and Z—$R^4$ is a TLR2 agonist, and the uses thereof in the treatment of infection, cancer or immune disorders or for use in vaccines.

10 Claims, 6 Drawing Sheets

CONJUGATED TLR7 AND/OR TLR8 AND TLR2 AGONISTS

FIELD OF THE INVENTION

The present invention provides conjugated TLR7 and/or TLR8 and TLR2 small molecule agonists for therapeutic applications. Specifically, the present application relates to novel conjugated compounds that mutually activate TLR7 and/or TLR8 and TLR2 receptors of the innate immune system. The invention provides methods for treating infections, immune disorders and cancer using the molecules of the invention.

BACKGROUND OF THE INVENTION

The innate immune system contains several families of germline-encoded pattern recognition receptors (PRRs), including Toll-like receptors (TLRs), Nod-like receptors (NLRs), RIG-1-like receptors (RLRs), cytosolic DNA sensors (CDSs) and C-type lectins (CLRs) (Newton and Dixit 2012). These receptors recognize microbial components termed pathogen-associated molecular patterns (PAMPs). PAMPs are highly conserved molecular structures on a wide range of pathogens such as bacteria, fungi, parasites and viruses. PAMPs include lipid-based bacterial cell wall components such as lipoproteins and lipopolysaccharides, microbial protein components such as flagellin, and pathogen nucleic acids in the form of double stranded DNA and single or double stranded RNA. In addition some PRRs also recognize 'self' ligands known as damage-associated molecular patterns (DAMPs) released from damaged or dying cells and tissues. Cells of the innate immune system respond to PAMPs and DAMPs by producing proinflammatory cytokines, chemokines and co-stimulatory molecules that are involved in clearing the pathogens and damaged-self. Furthermore, innate immune responses essentially shape the downstream adaptive immune responses to generate a more specific and long lasting immunity (Hoebe et al. 2004; Pasare and Medzhitov 2005). As such, harnessing innate immune signalling pathways is a promising therapeutic strategy to fight infections, immune disorders, as well as in diseases such as cancer.

TLRs are the best-studied class of innate immune receptors recognizing a diverse range of lipid-, protein-, nucleic acid-based PAMPs and DAMPs (Kawai and Akira 2011). The engagement of TLRs with their specific ligands leads to the activation of innate immune responses, and evokes adaptive immune responses through the activation of antigen presenting cells (APCs) and by amplifying B- and T-cell effector cells (Pasare and Medzhitov 2005; MacLeod and Wetzler 2007). Several studies have demonstrated that stimulation of TLRs with specific ligands and combinations of, to fine-tune adaptive immune responses. Moreover the aberrant TLR expression in cancer cells and several TLR polymorphisms identified in tumors indicate a role for TLRs in cancer (El-Omar et al. 2008; Kutikhin 2011; Mandal et al. 2012). The infiltration of TLR-expressing immune cells into the tumor microenvironment further implies the significance of TLRs and cancer (Bennaceur et al. 2009; Sato et al. 2009). However, the precise contribution of TLRs in cancer remains to be understood. Activation of TLRs can have opposing roles by either promoting cancer cell apoptosis or promoting tumor progression and survival (Huang et al. 2008). Overall, TLRs are promising targets for the development of new and effective therapeutic agents (Kanzler et al. 2007; Wang et al. 2008; So and Ouchi 2010). Several small molecules agonists of TLRs have been identified for use as immune stimulants to boost immunity against cancer (Meyer and Stockfleth 2008).

The present invention provides a method to stimulate biological activities of TLR7 and/or TLR8 and TLR2 with a single new conjugated molecule in order to treat diseases such as viral infections, immune disorders as well as cancer.

SUMMARY OF THE INVENTION

Provided herein are molecules and compositions and their application to modulate activities of TLR7 and/or TLR8 and TLR2 receptors of the innate immune system. This invention provides conjugated molecules that are TLR7 and/or TLR8 and TLR2 agonists able to mutually activate TLR7 and/or TLR8 and TLR2 receptors.

The synthetic molecules of the present invention are conjugated compounds of Formula I:

$$Q\text{-}Z\text{—}R^4 \qquad \text{Formula I}$$

with a molecular weight of less than 1000 Daltons in size, hereafter defined as small molecules.

One application of the molecules of the invention includes their use as anti-cancer agents or as vaccine adjuvants.

Toll-Like Receptors

TLRs are expressed by cells of the immune system and by certain non-immune cells such as epithelial and tumor cells. To date, 10 TLR isoforms have been identified in humans and 11 in mice. TLRs are type I membrane proteins with distinct cellular expression patterns and sub-cellular localization. TLR1, 2, 4, 5 and 6, are localized to the plasma membrane whereas TLR3, 4, 7, 8 and 9 reside in endosomal compartments, with TLR4 shuttling between the plasma membrane and endosomes. Engagement of TLRs with their specific ligands activates two major signalling pathways that are mediated by the adaptor proteins myeloid differentiation primary response gene 88 (MyD88) or TIR-domain-containing adaptor-inducing interferon-β (TRIF). Signalling cascades mediated by these pathways lead to the activation of transcription factors such as nuclear factor-kappa-B (NF-κB), activating protein-1 (AP-1) and interferon regulatory factors (IRFs) leading to the transcription of various genes for the production of inflammatory and anti-inflammatory cytokines, chemokines, and co-stimulatory molecules.

Since the induction of the adaptive immune system in vertebrates is heavily influenced by the innate immune system, TLR activation is an effective operation to effectively prime the adaptive response mediated by clonally distributed B- and T-cells. Several small molecule agonists of TLRs have been identified to shape adaptive immune responses to clear pathogens as well as to circumvent the process of carcinogenesis (Adams 2009; Rakoff-Nahoum and Medzhitov 2009). Agonists for TLR2 (Zhang et al. 2011), TLR3 (Salaun et al. 2011), TLR4 (Garay et al. 2007), TLR7 or TLR8 (Schon and Schon 2004) and TLR9 (Krieg 2008) have shown promise as anti-cancer treatments.

TLR7 and/or TLR8

TLR7 and TLR8 are, respectively, expressed in the endosomes of plasmacytoid dendritic cells (pDCs), macrophages and B cells, or myeloid dendritic cells (mDCs) and monocytes. TLR7 and TLR8 play a major role in the anti-viral response during viral infection by their ability to recognize single stranded RNA PAMPs. Several low molecular weight activators of TLR7 have been identified, which can be classified into three groups imidazoquinolines, nucleoside analogs of purines and 3-deazapurine derivatives (Hemmi et al. 2002; Lee et al. 2003; Jones et al. 2011). Imidazoquinoline derivatives include 1H-imidazo[4,5-c]quinolones (described in Gerster et al., U.S. Pat. No. 4,689,338 (Riker)) and imiquimod (3M-Aldara™, R-837, S-26308). Other members of imidazoquinolines are Resiquimod (R-848, S-28609), Gardiquimod, and CL097 (InvivoGen), which in contrast to imiquimod are also ligands for the TLR8 receptor.

Aldara™ is a cream formulation of imiquimod licensed for the topical treatment of anogenital warts, actinic keratosis and superficial basal cell carcinoma in humans. Nucleoside analogs of purines include 8-hydroxyadenines, such as 9-benzyl-8-hydroxy-2-(2-methoxyethoxy)adenine (SM-360320), (Kurimoto et al. 2004) and the compound CL264 (InvivoGen), which is derived from SM-360320 by incorporating the amino-acid glycine, on the benzyl group. The third class of TLR7 agonists is 3-deazapurines, which are purine derivatives that include an amine functional group on the benzyl moiety (Jones et al. WO Pat. No. 2007/093901 (Pfizer)).

TLR7 and TLR8 are targets for anti-cancer therapy (Smits et al. 2008; Bourquin et al. 2011; Hotz and Bourquin 2012). A variety of different small molecule compounds that are TLR7 modulators, either purine or imidazoquinoline derivatives, have been reported for the treatment of infections and diseases, in particular to treat cancer of the skin and bladder, autoimmune diseases, allergic diseases and as adjuvants for vaccines (Wu et al. US Pat. No. 2011/0053893 (Novartis); Isobe et al. U.S. Pat. No. 8,044,056 (Sumitomo); Fink et al. U.S. Pat. No. 7,485,432 (3M); Gorden et al. US Pat. No. 2011/0070575 (Coley); Johnson US Pat. No. 2011/0282061 (Glaxo); Biggadike et al. US Pat. No. 2011/0229500 (Glaxo); Cook et al. US Pat. No. 2010/0240623 (AstraZeneca); Carson et al. US Pat. No. 2010/0210598). More recently efficacy of TLR7 agonists have been reported in renal cell carcinoma (Kauffman et al. 2012).

TLR2

TLR2 is the most ubiquitous of the TLRs found expressed on the surface of all cells of the immune system, including monocytes, macrophages, dendritic cells, and B cells. TLR2 recognizes a large set of structurally diverse ligands including peptidoglycan, lipoteichoic acid and lipoprotein from gram-positive bacteria, lipoarabinomannan from mycobacteria, and zymosan from yeast cell wall. The ability for this wide range of recognition is due to the ability of TLR2 to form heterodimers with TLR1 and TLR6. Furthermore, ligand delivery by accessory molecules CD14 and CD36 are involved to enhance receptor signaling. Lipoproteins/lipopeptides are the major agonists for TLR2 (Zahringer et al. 2008). TLR2 dimerization with TLR1 recognizes tri-acylated lipopeptides, whereas TLR2/TLR6 heterodimers recognize di-acylated lipopeptides. Several TLR2 ligands, particularly lipopeptides, are exploited as vaccine adjuvants and their efficacy as anti-tumor agents are being assessed. The synthetic tri-acylated lipopeptide $Pam_3CSK_4$ has been proven to be a potent adjuvant for various vaccines, including a sublingual allergy vaccine, flu vaccine and leishmaniasis vaccine (Lombardi et al. 2008; Jayakumar et al. 2011; Caproni et al. 2012). TLR2 is associated with arthritis, in particular rheumatoid arthritis, in lung disease, and in cancer (Leah 2011; Palsson-McDermott et al. 2007; Schmidt et al. 2007). Recent studies are focused on the design of new synthetic TLR2 immunomodulatory agents to be effective as therapeutics (Nakaar et al. US Pat No. 2009/0028889 (Vaxinnate); Finberg et al. U.S. Pat. No. 2011/0152251). TLR2 agonists have been shown to induce tumor regression or prolong survival in cancer patients (Garay et al. 2007; Curtin et al. 2009; Zhang et al. 2011). However targeting TLR2 for therapeutic reasons has been complicated due to its ability to detect a great number and variety of PAMPs and also DAMPs, and its implication in auto-immune diseases. It has been demonstrated that combinations of agonists of the innate immune system can effectively enhance adjuvancy. For instance combining ligands for TLRs may better mimic viral recognition (Whitmore et al. 2004) or induce effective tumor-specific responses (Garaude et al. 2012). Furthermore TLR2/6 agonist with a TLR9 agonist has been reported to induce a synergistic response in the resistance to pneumonia (Duggan et al. 2011; Tuvim et al. 2012)

A number of small molecule agonists of TLR2 have recently been described that specifically activate human TLR2 (Agnihotri et al. 2011). $Pam_2CS$, the backbone TLR2 agonist, has been reported to exhibit potent adjuvantic activity in a model of immunization without inducing an inflammatory response (Salunke et al. 2012). Derivatives of these small molecules TLR2 agonists have been conjugated to TLR7 ligands to form a single molecule and are described in the present invention.

The synthetic immunogenic conjugated molecules of the present invention include compounds of Formula II:

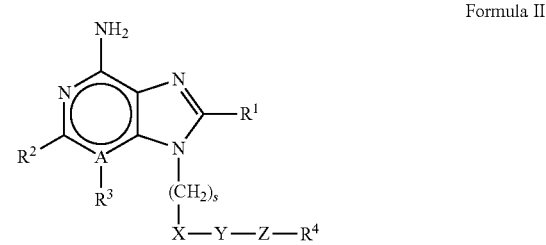

Formula II wherein A, $R^1$, $R^2$, $R^3$, X, Y, Z, and $R^4$ are as defined hereafter.

Purine, imidazoquinoline or 3-deazapurine derivatives described herein disclose modulators of TLR7 and/or TLR8 and Z—$R^4$ is a modulator of TLR2.

The object of the present invention is to provide a novel low molecular weight TLR7 and/or TLR8 agonist covalently linked to a TLR2 agonist.

Furthermore, the present invention relates to a process for preparing a heterocyclic compound covalently linked to an acylated S-glyceryl or 2-hydroxythioethyl cysteine of the above Formula II or its pharmaceutically acceptable salt.

DETAILED DESCRIPTION OF THE INVENTION

The present invention provides novel low molecular weight conjugated compounds comprising a TLR7 and/or TLR8 agonist covalently linked to a TLR2 agonist that induce innate immune responses when contacting cells. The compounds of the invention are therefore interferon inducers, anti-cancer agents, anti-infectious agents, therapeutic agents for immunological diseases and vaccine adjuvants. More particularly, the molecules of the invention comprise heterocyclic compounds that are TLR7 and/or TLR8 agonists of Formula I or II as defined below, or pharmaceutically acceptable salt thereof. Furthermore, the present invention relates to a process for preparing heterocyclic compounds of the Formula I or II, or pharmaceutically acceptable salts thereof.

Unless stated otherwise, the following terms used in the specification and claims have the meanings indicated below.

$C_i$-$C_j$ alkyl means a linear or branched alkyl group comprising from i to j carbon atoms. Alkyl groups include for instance methyl, ethyl, n-propyl, isopropyl, n-butyl, isobutyl, pentyl, and hexyl.

$C_{i-j}$ alkenyl means an unsaturated hydrocarbon chain wherein i denotes the number of carbon atoms in the hydrocarbon chain and j denotes the number of double bonds in the hydrocarbon chain. Alkenyl groups include for instance vinyl, allyl, octenyl, oleyl, arachidonyl.

$C_i$-$C_j$ alkylamino means a $C_i$-$C_j$ alkyl-NH— group wherein $C_i$-$C_j$ alkyl is defined as above. Alkylamino groups include for instance methylamino, ethylamino, n-propylamino, or n-butylamino.

Di($C_i$-$C_j$ alkyl)amino means a ($C_i$-$C_j$ alkyl)$_2$N— group wherein $C_i$-$C_j$ alkyl is as defined above. Dialkylamino groups include for instance di methylamino or diethylamino.

$C_i$-$C_j$ alkoxy means a $C_i$-$C_j$ alkyl-O— group wherein $C_i$-$C_j$ alkyl is defined as above. Alkoxy groups include for instance methoxy or ethoxy.

$C_i$-$C_j$ cycloalkyl means a non-aromatic saturated carbocyclic radical, consisting of one or several rings, comprising from i to j carbon atoms. Cycloalkyl groups include for instance cyclopropyl, cyclobutyl, cyclopentyl, cyclohexyl, cycloheptyl, decahydronaphthalene, or octahydro-1H-indene.

$C_i$-$C_j$ carbocyclic means a non-aromatic saturated carbocyclic ring comprising from i to j carbon atoms. Carbocyclic groups include for instance cyclopropyl, cyclobutyl, cyclopentyl, cyclohexyl, cycloheptyl.

$C_i$-$C_j$ cycloalkyl-$C_m$—$C_n$ alkyl means a $C_i$-$C_j$ cycloalkyl-R— group wherein R is a linear or branched alkyl group comprising from m to n carbon atoms. $C_3$-$C_6$cycloalkyl-$C_1$-$C_6$alkyl groups include for instance ethylcyclopentyl, propylcyclopentyl, ethylcyclohexyl, or propylcyclohexyl.

$C_i$-$C_j$ cycloalkyl-$C_m$-$C_n$ alkylamino means a $C_i$-$C_j$ cycloalkyl-R—NH— group wherein R is a linear or branched alkyl group comprising from m to n carbon atoms. $C_3$-$C_6$cycloalkyl-$C_1$-$C_6$alkylamino groups include for instance cyclopentylmethanamino, 2-cyclopentylethanamino, cyclohexylmethanamino, or 2-cyclohexylethanamino.

$C_i$-$C_j$ alkoxy$C_m$-$C_n$ alkylamino means a $C_i$-$C_j$ alkoxy-R—NH— group wherein R is a linear or branched alkyl group comprising from m to n carbon atoms. $C_1$-$C_{10}$alkoxy$C_1$-$C_{10}$alkylamino groups include for instance 2-ethoxyethanamino, 2-propoxyethanamino, 3-ethoxypropan-1-amino, 3-propoxypropan-1-amino.

$C_i$-$C_j$ alkoxy$C_m$-$C_n$ alkoxy means a $C_i$-$C_j$ alkoxy-R— group wherein R is a $C_m$-$C_n$ alkoxy group as defined above. $C_1$-$C_{10}$alkoxy$C_1$-$C_{10}$alkoxy groups include for instance 2-ethoxyethoxy, 2-propoxyethoxy, 3-ethoxypropoxy, or 3-propoxypropoxy.

$C_i$-$C_j$ aryl means an aromatic carbocyclic radical consisting of one or several rings, containing from i to j carbon atoms. Aryl groups include for instance phenyl.

$C_i$-$C_j$ heterocyclyl and $C_i$-$C_j$ heterocycle respectively means a non-aromatic saturated cyclic radical and cycle consisting of one or several rings, comprising from i to j atoms including one or several heteroatoms chosen among N, O and S. Heterocyclyl groups include for instance tetrahydrofuranyl, tetrahydropyranyl, tetrahydrothioaziridinyl, N-pyrrolidinyl, N-piperidinyl, or N-morpholinyl.

$C_i$-$C_j$ alkoxycarbonyl means a $C_i$-$C_j$ alkoxy-CO— group wherein the $C_i$-$C_j$alkoxy group is as defined above.

$C_i$-$C_j$ alkanoyl means a $C_i$-$C_j$ alkyl-CO— group wherein the $C_i$-$C_j$ alkyl group is as defined above.

The suffix "ene" means that the radical is divalent. For instance, $C_1$-$C_6$ alkylene means a linear or branched divalent hydrocarbon chain comprising from 1 to 6 carbon atoms, or $C_6$-$C_{20}$ arylene means an aromatic carbocyclic divalent radical consisting of one or several rings, containing from 6 to 20 carbon atoms.

The "specific side chain of an amino acid" means the R group of an amino acid having the generic Formula H$_2$NCHRCOOH Amino acids include for instance the L or D isomers of alanine, valine, leucine, isoleucine, phenylalanine, tryptophan, methionine, glycine, serine, threonine, cysteine, tyrosine, asparagine, glutamine, aspartic acid, glutamic acid, lysine, arginine, proline and histidine.

The term "agonist," as used herein, refers to a compound that can combine with a receptor (e.g., a TLR) to produce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may be referred to as an agonist of a particular TLR (e.g., a TLR7 agonist) or a particular combination of TLRs (e.g., a TLR2/6 agonist is an agonist of TLR2 and TLR6).

An agonist that selectively modulates biological activity through a particular TLR may be a TLR-selective agonist.

A TLR agonist is any compound or substance that functions to activate a TLR, e.g., to induce a signaling event mediated by a TLR signal transduction pathway. Suitable TLR agonists of the invention include TLR7 and/or TLR8 agonists and TLR2 agonists.

"TLR7 and/or TLR8" agonist refers to a molecule that is an agonist of TLR7 only, TLR8 only or both TLR7 and TLR8. TLR7 and/or TLR8 agonists are well known in the art.

Examples of TLR7 agonists are purine or purine-like molecules such as 8-hydroxyadenine, imidazoquinoline and derivatives such as imiquimod, and pyridinomidazol.

Some molecules, such as Resiquimod (R848), Gardiquimod and CL097 (InvivoGen), are both TLR7 and TLR8 agonists. These molecules that are both TLR7 and TLR8 agonists are also called herein TLR7/8 agonists.

"TLR2" agonists of the invention include synthetic mono-acetylated, di-acylated or tri-acylated lipopeptides.

TLR2 agonists include Pam$_2$Cys (dipalmitoyl-S-glyceryl cysteine) or S-[2,3-bis(palmitoyloxy)-(2RS)-propyl]-(R)-cysteine, where "Pam$_2$" is "dipalmitoyl-S-glyceryl"). Derivatives of Pam$_2$Cys are also suitable TLR2 agonists, where derivatives include, but are not limited to Pam$_2$CSK$_4$ (dipalmitoyl-S-glyceryl cysteine-serine-(lysine)$_4$ or Pam$_2$Cys-Ser-(Lys)$_4$, a synthetic di-acylated lipopeptide). Synthetic TLRs agonists have been described in the literature.

TLR2 agonists also include synthetic Pam$_3$Cys (tripalmitoyl-S-glyceryl cysteine) or S-[2,3-bis(palmitoyloxy)-(2RS)-propyl]-N-palmitoyl-(R)-cysteine, where "Pam$_3$" is "tripalmitoyl-S-glyceryl"). Derivatives of Pam$_3$Cys are also suitable TLR2 agonists, where derivatives include, but are not limited to Pam$_3$Cys-Ser-(Lys)$_4$ or S-[2,3-bis(palmitoyloxy)-(2-R,S)-propyl]-N-palmitoyl-(R)-Cys-(S)-Ser-(Lys)$_4$.

Another non-limiting example of a suitable TLR2 agonist is a mono-acylated lipopeptide or mono-acylated amino acid where the thioglycerol moiety is replaced with a thioethanol bridge. These TLR2 derivatives have been described in the literature and include mono-acetylated 2-hydroxythioethyl-cysteine. Derivatives of mono-acylated are also suitable TLR2 agonists, where derivatives include, but are not limited to ethylmyristate, ethylpalmitate and ethylstearate.

In some embodiments, a suitable TLR2 agonist activates TLR2, potentially in heterodimerisation with TLR1 or TLR6. The molecules of the present invention have TLR2 agonist activity and may activate TLR1 or TLR6 due to heterodimer formation.

The molecules of the present invention are in fact conjugated compounds comprising a TLR7 and/or TLR8 agonist that is covalently attached to a TLR2 agonist.

"Treatment or treating" refers to both curative treatment and prophylactic or preventive measures, wherein the object is to prevent or slow down the targeted pathologic condition or disorder. Those in need of treatment include those already with the disorder as well as those prone to have the disorder or those in whom the disorder is to be prevented. Hence, the subject to be treated herein may have been diagnosed as having the disorder or may be predisposed or susceptible to the disorder.

"Pharmaceutically acceptable salts" of a compound means salts that are pharmaceutically acceptable and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

"Solvates" means solvent additions forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

Polymorphs as referred to herein can include crystalline and amorphous forms, which can be further characterised as follows:

i) Crystalline forms have different arrangements and/or conformations of the molecules in the Crystal lattice, (ii) Amorphous forms consist of disordered arrangements of molecules that do not possess a distinguishable crystal lattice.

A first object of the present invention is a conjugated compound of Formula I:

$$Q\text{-}Z\text{—}R^4 \qquad \text{Formula I}$$

wherein:

Q is a TLR7 and/or TLR8 agonist; and

Z—$R^4$ is a TLR2 agonist selected from the group consisting of:

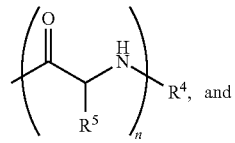

Formula III

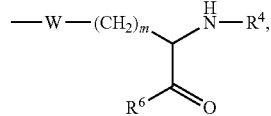

Formula IV wherein:

$R^5$ is the specific side chain of an amino acid;

n is 0 or 1;

W is a single bond, —O—, —S—, —NH—, —C(O)—, or —S(O)$_2$—;

m is an integer from 1 to 4 (thus m is 0, 1, 2, 3 or 4);

$R^6$ is H, OH, —O—$C_1$-$C_{30}$alkyl, —NH—$C_1$-$C_{30}$alkyl, —S—$C_1$-$C_{30}$alkyl, or —O—$C_2$-$C_{30}$alkylenyl;

$R^4$ is a lipid of formula V:

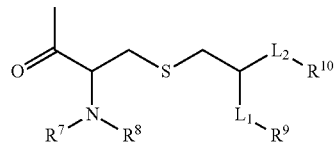

Formula V wherein:

$R^7$ and $R^8$ are independently from each other H, $C_1$-$C_{30}$alkyl, $C_2$-$C_{30}$alkylenyl, —C(O)—$C_1$-$C_{30}$alkyl, —C(O)—$C_2$-$C_{30}$alkylenyl, or —C(O)—O—$C_1$-$C_{30}$alkyl;

$R^9$ is $C_1$-$C_{30}$alkyl or $C_2$-$C_{30}$alkylenyl;

$R^{10}$ is $C_1$-$C_{30}$alkyl or $C_2$-$C_{30}$alkylenyl;

$L_1$ is absent, —OC(O)—, —O—, —NR$^{11}$C(O)—, —OC(O)NR$^{11}$— or —CH$_2$— wherein $R^{11}$ is H, $C_1$-$C_{30}$alkyl or $C_2$-$C_{30}$alkylenyl;

$L_2$ is —CH$_2$OC(O)—, —CH$_2$O—, —CH$_2$NR$^{11}$C(O)— or —CH$_2$—, if $L_1$ is absent $L_2$ is —OC(O)—, —O—, —NR$^{11}$C(O)—, —NR$^{10}$R$^{11}$, —OC(O)NR$^{11}$— or —CH$_2$— wherein $R^{11}$ is as defined above.

Preferably, the compounds of formula I are imidazoquinoline, purine and 3-deazapurine derivatives, i.e. the radical Q of Formula I contains a moiety which is selected from the group consisting of imidazoquinoline, purine and 3-deazapurine derivatives.

Hence, the radical Q may be represented by the following formula:

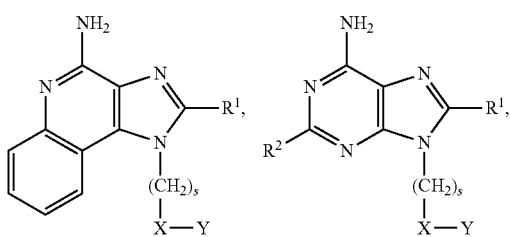

(imidazoquinoline derivative)  (purine derivative)

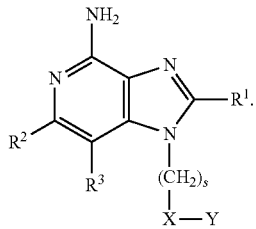

(3-deazapurine derivative)

A preferred class of compounds provided by the present invention comprises those of the general Formula II:

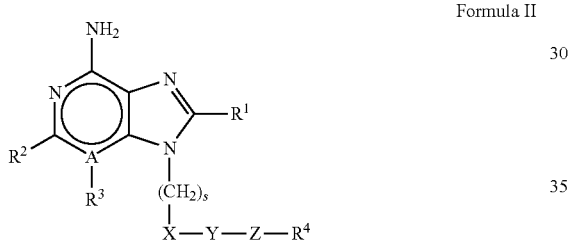

Formula II a tautomer thereof or a pharmaceutically acceptable salt, solvate or polymorph of said compound or tautomer, wherein:

A is a carbon or nitrogen atom;

$R^1$ is —H, —OH, —SH, —NH$_2$, —CF$_3$, halogen, or a group chosen from C$_1$-C$_6$alkyl, C$_1$-C$_6$alkylamino, C$_1$-C$_6$alkoxy, C$_3$-C$_6$cycloalkyl-C$_1$-C$_6$alkyl, C$_3$-C$_6$cycloalkyl-C$_1$-C$_6$alkylamino, C$_3$-C$_6$cycloalkyl, C$_1$-C$_6$alkoxyC$_1$-C$_6$alkylamino, or C$_1$-C$_6$alkoxyC$_1$-C$_6$alkoxy, (C$_1$-C$_6$alkyl)-E-(C$_1$-C$_6$alkylene)- wherein E is —O—, —S—, —N(R$^{12}$)—, —C(O)— or —S(O)$_2$— and R$^{12}$ is —H, carboxyl, —NH$_2$, C$_1$-C$_6$alkyl, C$_1$-C$_6$alkoxy, C$_1$-C$_6$alkanoyl, C$_6$-C$_{20}$aryl, C$_6$-C$_{20}$ heteroaryl, or C$_1$-C$_6$alkoxycarbonyl, said group being optionally terminally substituted with a hydroxyl, amino, thiol, hydrazino, hydrazido, azido, acetylenyl, carboxyl, or maleimido group;

$R^2$ and $R^3$ independently from each other are H, OH, SH, NH$_2$, CF$_3$, halogen, C$_1$-C$_{10}$alkyl, C$_1$-C$_{10}$alkylamino, C$_1$-C$_{10}$dialkylamino, C$_1$-C$_{10}$alkoxy, C$_1$-C$_{10}$alkoxy-C$_1$-C$_{10}$ alkylamino, C$_1$-C$_{10}$alkoxy-C$_1$-C$_{10}$alkoxy, C$_1$-C$_{10}$alkoxy-C$_5$-C$_7$heterocycle, C$_1$-C$_{10}$alkyamino-C$_5$-C$_7$heterocycle, —NH—SO$_2$—C$_1$-C$_6$alkyl, —C(O)—C$_1$-C$_6$alkyl, —O—C(O)—C$_1$-C$_6$alkyl, —C(O)—C$_1$-C$_{10}$alkylamino, —C(O)—C$_1$-C$_{10}$dialkylamino, C$_5$-C$_{10}$aryl, C$_5$-C$_9$heterocyclyl, C$_3$-C$_9$ carbocyclyl, C$_1$-C$_{10}$alkylamino-C$_2$-C$_7$heterocycle, (C$_1$-C$_6$alkoxy)-E-(C$_1$-C$_6$alkylene) or when taken together, $R^2$ and $R^3$ form a fused C$_6$-C$_{20}$ aryl, C$_4$-C$_{20}$ heteroaryl, C$_5$-C$_7$-carbocycle or a C$_4$-C$_7$heterocycle; where carbocycle, heterocycle, aryl, and heteroaryl are optionally substituted with one or more groups independently selected from F, Cl, Br, I, —CH$_3$, —CH$_2$CH$_3$, CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CHF$_2$, —CO$_2$H, —COCH$_3$, —CO$_2$CH$_3$, —C(CH$_3$)$_2$CO$_2$CH$_3$, —CO$_2$C(CH$_3$)$_3$, —COCH(OH)CH$_3$, —COCH(CH$_3$)$_2$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino;

$R^3$ is absent when A is a nitrogen atom;

s is an integer from 1 to 4 (thus s is 0, 1, 2, 3 or 4);

X is an unbranched —(C$_1$-C$_6$ alkylene)-, —(C$_6$-C$_{20}$arylene)-, —(C$_4$-C$_{20}$heteroarylene)-, —(C$_1$-C$_6$ alkylene)-E-(C$_1$-C$_6$ alkylene)-, —(C$_1$-C$_6$ alkylene)-(C$_3$-C$_7$-carbocyclylene)-, —(C$_1$-C$_6$ alkylene)-(C$_3$-C$_7$-heterocyclylene)-, —(C$_1$-C$_6$ alkylene)-(C$_6$-C$_{20}$ arylene)-, —(C$_1$-C$_6$ alkylene)-(C$_4$-C$_{20}$ heteroarylene)-, —(C$_1$-C$_6$ alkylene)-E-(C$_1$-C$_7$ carbocyclylene)-, —(C$_1$-C$_6$ alkylene)-E-(C$_3$-C$_7$-heterocyclylene)-, —(C$_1$-C$_6$ alkylene)-E-(C$_6$-C$_{20}$ arylene)-, —(C$_1$-C$_6$ alkylene)-E-(C$_4$-C$_{20}$ heteroarylene)-, where alkylene, carbocyclylene, heterocyclylene, arylene, and heteroarylene are optionally substituted with one or more groups independently selected from F, Cl, Br, I, —CH$_3$, —CH$_2$CH$_3$, CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CHF$_2$, —CO$_2$H, —COCH$_3$, —CO$_2$CH$_3$, —C(CH$_3$)$_2$CO$_2$CH$_3$, —CO$_2$C(CH$_3$)$_3$, —COCH(OH)CH$_3$, —COCH(CH$_3$)$_2$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino, and E is as defined above;

Y is a single bond, —O—, —S—, —N(R$^{12}$)—, —C(O)—, or —S(O)$_2$— and R$^{12}$ is as defined above;

Z—R$^4$ is selected from the group consisting of:

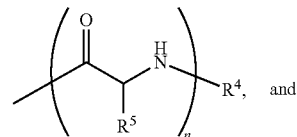

Formula III and

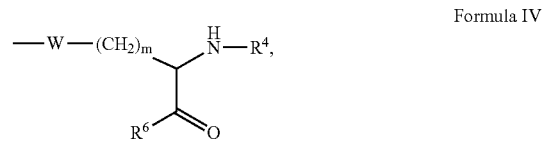

Formula IV wherein:

$R^5$ is the specific side chain of an amino acid;

n is 0 or 1;

W is a single bond, —O—, —S—, —NH—, —C(O)—, or —S(O)$_2$—;

m is an integer from 1 to 4 (thus m is 0, 1, 2, 3 or 4);

$R^6$ is H, OH, —O—$C_1$-$C_{30}$alkyl, —NH—$C_1$-$C_{30}$alkyl, —S—$C_1$-$C_{30}$alkyl, —O—$C_2$-$C_{30}$alkylenyl $R^4$ is a lipid of formula V:

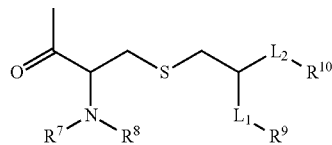

Formula V wherein:

$R^7$ and $R^8$ are independently from each other H, $C_1$-$C_{30}$alkyl, $C_3$-$C_{30}$alkylenyl, —C(O)—$C_1$-$C_{30}$alkyl or —C(O)—$C_2$-$C_{30}$alkylenyl, —C(O)—O—$C_1$-$C_{30}$alkyl;

$R^9$ is $C_1$-$C_{30}$alkyl or $C_2$-$C_{30}$alkylenyl;

$R^{10}$ is $C_1$-$C_{30}$alkyl or $C_2$-$C_{30}$alkylenyl;

$L_1$ is absent, —OC(O)—, —O—, —NR$^{11}$C(O)—, —OC(O)NR$^{11}$— or —CH$_2$— wherein R$^{11}$ is H, $C_1$-$C_{30}$alkyl or $C_2$-$C_{30}$alkylenyl;

$L_2$ is —CH$_2$OC(O)—, —CH$_2$O—, —CH$_2$NR$^{11}$C(O)— or —CH$_2$—, if $L_1$ is absent $L_2$ is —OC(O)—, —O—, —NR$^{11}$C(O)—, —NR$^{10}$R$^{11}$, —OC(O)NR$^{11}$— or —CH$_2$— wherein R$^{11}$ is as defined above.

In one embodiment, the compounds of the invention are chosen among purine derivatives wherein:

A is a nitrogen atom, $R^3$ is absent and $R^2$ is H, OH, SH, NH$_2$, CF$_3$, halogen, $C_1$-$C_{10}$ alkyl, $C_1$-$C_{10}$ alkylamino, $C_1$-$C_{10}$dialkylamino, $C_1$-$C_{10}$alkoxy, $C_1$-$C_{10}$alkoxy-$C_1$-$C_{10}$ alkylamino, $C_1$-$C_{10}$alkoxy-$C_1$-$C_{10}$alkoxy, $C_1$-$C_{10}$alkoxy-$C_5$-$C_7$heterocycle, $C_1$-$C_{10}$ alkyamino-$C_5$-$C_7$heterocycle, —NH—SO$_2$—$C_1$-$C_6$alkyl, —C(O)—$C_1$-$C_6$alkyl, —O—C(O)—$C_1$-$C_6$alkyl, —C(O)—$C_1$-$C_{10}$alkylamino, —C(O)—$C_1$-$C_{10}$dialkylamino, $C_5$-$C_{10}$aryl, $C_5$-$C_9$heterocyclyl, $C_3$-$C_9$ carbocyclyl, $C_1$-$C_{10}$alkylamino-$C_2$-$C_7$heterocycle, ($C_1$-$C_6$alkoxy)-E-($C_1$-$C_6$alkylene) and preferably $R^1$ is —H, —OH, —SH, —NH$_2$, $C_1$-$C_6$alkyl, such as methyl, ethyl, propyl or butyl, $C_1$-$C_6$alkylamino such as methylamino, ethylamino, propylamino or butylamino, $C_1$-$C_6$alkoxy such as methoxy, ethoxy, propoxy or butoxy, ($C_1$-$C_6$alkyl)-E-($C_1$-$C_6$alkylene), wherein E is —O— or —NH—, such as —CH$_2$—NH—C$_2$H$_5$, —CH$_2$—O—C$_2$H$_5$, —(CH$_2$)$_2$—NH—CH$_3$, or —(CH$_2$)$_2$—O—CH$_3$, more preferably $R^1$ is —OH.

In other embodiment, the compounds of the invention are chosen among imidazoquinoline derivatives wherein:

A is a carbon atom and $R^2$ and $R^3$ form together a fused phenyl optionally substituted with one or more groups independently selected from F, Cl, Br, I, —CH$_3$, —CH$_2$CH$_3$, CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CHF$_2$, —CO$_2$H, —COCH$_3$, —CO$_2$CH$_3$, —C(CH$_3$)$_2$CO$_2$CH$_3$, —CO$_2$C(CH$_3$)$_3$, —COCH(OH)CH$_3$—COCH(CH$_3$)$_2$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino, and preferably $R^1$ is —H, —OH, —SH, —NH$_2$, $C_1$-$C_6$alkyl, such as methyl, ethyl, propyl or butyl, $C_1$-$C_6$alkylamino such as methylamino, ethylamino, propylamino or butylamino, $C_1$-$C_6$alkoxy such as methoxy, ethoxy, propoxy or butoxy, ($C_1$-$C_6$alkyl)-E-($C_1$-$C_6$alkylene), wherein E is —O— or —NH—, such as —CH$_2$—NH—C$_2$H$_5$, —CH$_2$—O—C$_2$H$_5$, —(CH$_2$)$_2$—NH—CH$_3$, or —(CH$_2$)$_2$—O—CH$_3$.

In other embodiment, the compounds of the invention are chosen among 3-deazapurine derivatives wherein:

A is a carbon atom and $R^2$ and $R^3$ independently from each other are H, OH, SH, NH$_2$, CF$_3$, halogen, $C_1$-$C_{10}$alkyl, $C_1$-$C_{10}$alkylamino, $C_1$-$C_{10}$dialkylamino, $C_1$-$C_{10}$alkoxy, $C_1$-$C_{10}$alkoxy-$C_1$-$C_{10}$ alkylamino, $C_1$-$C_{10}$alkoxy-$C_1$-$C_{10}$alkoxy, $C_1$-$C_{10}$alkoxy-$C_5$-$C_7$heterocycle, $C_1$-$C_{10}$alkyamino-$C_5$-$C_7$heterocycle, —NH—SO$_2$—$C_1$-$C_6$alkyl, —C(O)—$C_1$-$C_6$alkyl, —O—C(O)—$C_1$-$C_6$alkyl, —C(O)—$C_1$-$C_{10}$alkylamino, —C(O)—$C_1$-$C_{10}$dialkylamino, $C_5$-$C_{10}$aryl, $C_5$-$C_9$heterocyclyl, $C_3$-$C_9$ carbocyclyl, $C_1$-$C_{10}$alkylamino-$C_2$-$C_7$heterocycle, ($C_1$-$C_6$alkoxy)-E-($C_1$-$C_6$alkylene) and preferably $R^1$ is —H, —OH, —SH, —NH$_2$, $C_1$-$C_6$alkyl, such as methyl, ethyl, propyl or butyl, $C_1$-$C_6$alkylamino such as methylamino, ethylamino, propylamino or butylamino, $C_1$-$C_6$alkoxy such as methoxy, ethoxy, propoxy or butoxy, ($C_1$-$C_6$alkyl)-E-($C_1$-$C_6$alkylene), wherein E is —O— or —NH—, such as —CH$_2$—NH—C$_2$H$_5$, —CH$_2$—O—C$_2$H$_5$, —(CH$_2$)$_2$—NH—CH$_3$, or —(CH$_2$)$_2$—O—CH$_3$, more preferably $R^1$ is —OH.

The lipid moiety $R^4$ includes synthetic analogues of a bacterial lipoprotein known as MALP-2, derived from the cytoplasmic membrane of *Mycoplasma* fermentans:

dipalmitoyl-S-glyceryl cysteine (Pam$_2$Cys). Pam$_2$Cys is a ligand for both TLR2 and TLR6 (Okusawa et al, 2004);

tripalmitoyl-S-glyceryl cysteine (Pam$_3$Cys). Pam$_3$Cys is a ligand for both TLR2 and TLR1;

or a mono-acylated 2-hydroxythioethyl cysteine, which is a specific ligand for human TLR2 (Agnihotri et al. 2011).

Exemplary fatty acids include, but are not limited to, stearoyl, palmitoyl, myristoyl, lauroyl, and decanoyl groups. More generally, any $C_2$ to $C_{30}$ saturated, monounsaturated, or polyunsaturated fatty acyl group is thought to be useful, including, but not limited to vinyl, allyl, octenyl, oleyl, or arachidonyl groups.

The lipoamino acid N-palmitoyl-S[2,3-bis(palmitoyloxy) propyl]cysteine, also known as Pam$_3$C, Pam$_3$Cys or Pam$_3$Cys-OH (Wiesmuller et al. 1983) is a synthetic version of the N-terminal moiety of Braun's lipoprotein that spans the inner and outer membranes of Gram negative bacteria. Pam$_3$Cys has the structure of following formula:

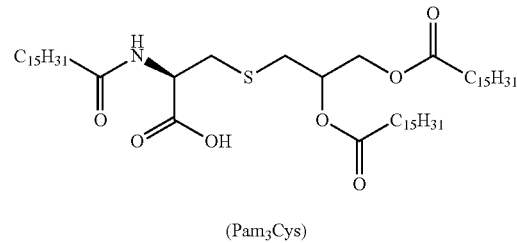

(Pam$_3$Cys)

N-acyl-S-(2-hydroxyalkyl)cysteine is an intermediate in the preparation of lipopeptides that are used as synthetic adjuvants, B lymphocyte stimulants, macrophage stimulants, or synthetic vaccines. Metzger et al. (U.S. Pat. No. 5,700,910) teach the use of such compounds as intermediates in the synthesis of $Pam_3Cys$-OH and of lipopeptides that comprise this lipoamino acid or an analog thereof at the N-terminus. The lipopeptides are prepared by coupling a lipoamino acid moiety to the peptide moiety during the synthesis process.

$Pam_2Cys$ (also known as dipalmitoyl-S-glyceryl-cysteine or S-[2,3-bis(palmitoyloxy)propyl]cysteine), an analogue of $Pam_3Cys$, has been synthesized (Metzger et al. 1995) and has been shown to correspond to the lipid moiety of MALP-2, a macrophage-activating lipopeptide isolated from mycoplasma (Muhlradt et al. 1998; Sacht et al. 1998) $Pam_2Cys$ has the structure of following formula:

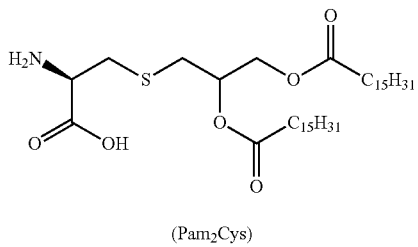

($Pam_2Cys$)

$Pam_2Cys$ is reported to be a more potent stimulator of splenocytes and macrophages than $Pam_3Cys$ (Metzger et al. 1995; Muhlradt et al. 1998)

Monoacyl lipopeptides also known as S-(2-acyloxyethyl) cysteinyl]-serine methyl ester is described to have human specific TLR2 agonistic properties (Agnihotri et al. 2011; Salunke et al. 2012):

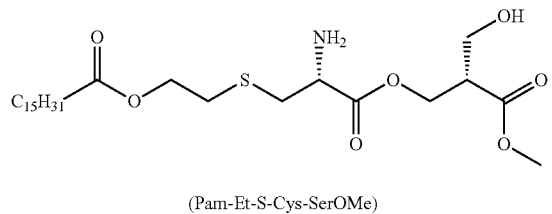

(Pam-Et-S-Cys-SerOMe)

A specific class of compounds of Formula II comprises those where Y is —NH—, —O—, —S—, or —C(O)—.

A specific class of compounds of Formula II comprises those where X is a —($C_6$-$C_{20}$arylene) (preferably a phenylene), a —($C_1$-$C_6$ alkylene)- (preferably an ethylene or a propylene), or a —($C_4$-$C_{20}$heteroarylene)- (preferably a pyridinylene, a pyrimidinylene, or a pyridazylene).

A specific class of compounds of Formula II comprises those where s is 1.

A specific class of compounds of Formula II comprises those where $R^1$ is —H, —OH, —SH, —$NH_2$, $C_1$-$C_6$alkyl, such as methyl, ethyl, propyl or butyl, $C_1$-$C_6$alkylamino such as methylamino, ethylamino, propylamino or butylamino, $C_1$-$C_6$alkoxy such as methoxy, ethoxy, propoxy or butoxy, ($C_1$-$C_6$alkyl)-E-($C_1$-$C_6$alkylene), wherein E is —O— or —NH—, such as —$CH_2$—NH—$C_2H_5$, —$CH_2$—O—$C_2H_5$, —($CH_2$)$_2$—NH—$CH_3$, or —($CH_2$)$_2$—O—$CH_3$.

A specific class of compounds of Formula II comprises those where A is a nitrogen atom, $R^2$ is a $C_1$-$C_6$alkylamino, such as propylamino or butylamino, $C_1$-$C_6$alkoxy such as propoxy, or butoxy, ($C_1$-$C_6$alkoxy)-E-($C_1$-$C_6$alkylene), wherein E is —O— or —NH— such as —O—($CH_2$)$_2$—O—$CH_3$, and $R^3$ is absent.

A specific class of compounds of Formula II comprises those where A is a carbon atom and $R^2$ and $R^3$ form a fused $C_6$-$C_{20}$ aryl, preferably a phenyl, a —($C_4$-$C_{20}$heteroaryl)- (preferably a pyridinyl, a pyrimidinyl, or a pyridazyl), or a —($C_5$-$C_7$carbocycle)-(preferably a cyclohexyl).

A specific class of compounds of Formula II comprises those where A is a carbon atom and $R^3$ is a hydrogen atom and $R^2$ is $C_1$-$C_6$alkylamino, such as propylamino or butylamino, $C_1$-$C_{10}$alkylamino-$C_2$-$C_7$heterocycle, such as —NH—$CH_2$—$C_2$-$C_7$heterocyclic group, in particular —NH—$CH_2$-tetrahydropyranyl or —NH—$CH_2$-tetrahydrofuranyl, $C_1$-$C_6$alkoxy such as propoxy or butoxy, $C_1$-$C_{10}$alkoxy-$C_2$-$C_7$heterocycle, such as —O—$CH_2$—$C_2$-$C_7$heterocyclic group in particular —O—$CH_2$-tetrahydropyranyl or —O—$CH_2$-tetrahydrofuranyl, ($C_1$-$C_6$alkoxy)-E-($C_1$-$C_6$alkylene)-, wherein E is —O— or —NH— such as —O—($CH_2$)$_2$—O—$CH_3$.

A specific class of compounds of Formula I or II comprises those where —Z— is absent.

A specific class of compounds of Formula I or II comprises those where —Z—$R^4$ is of Formula III wherein n=1 and $R^5$ is the specific side chain of an amino acid, such as —$CH_2$OH, for serine or —($CH_2$)$_2$—COOH for glutamic acid or —($CH_2$)$_2$—$COOCH_3$ for glutamic acid with a methyl ester, —$CH_2$—COOH for aspartic acid or —$CH_2$—$COOCH_3$ for aspartic acid with a methyl ester.

A specific class of compounds of Formula I or II comprises those where —Z—$R^4$ is of Formula IV wherein m=1, 2, 3 or 4, W is —O—, —NH—, or —C(O)— and $R^6$ is —OH, —O—$C_1$-$C_{30}$alkyl such as methoxy or ethoxy, or —NH—$C_1$-$C_{30}$alkyl such as methylamino or ethylamino.

A specific class of compounds of Formula I or II comprises those where $R^4$ is a lipid of formula V:

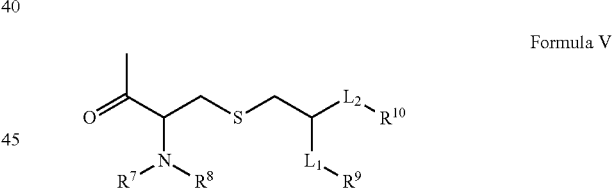

Formula V wherein:

$R^7$ and $R^8$ are independently from each other H or —C(O)—$C_1$-$C_{30}$alkyl such as —$COCH_3$, —$COC_{13}H_{27}$, —$COC_{15}H_{31}$, or —$COC_{17}H_{35}$;

$R^9$ and $R^{10}$ are independently from each other $C_1$-$C_{30}$alkyl, such as —$COC_{13}H_{27}$, —$COC_{15}H_{31}$, or —$COC_{17}H_{35}$; and $L_1$ is absent and $L_2$ is —OC(O)—; or $L_1$ is —OC(O)— and $L_2$ is —$CH_2$OC(O)—.

A preferred class of compounds of Formula I or II is any combination of the specific classes defined above.

In one preferred embodiment of Formula II:
A is nitrogen,
$R^1$ is —OH,
$R^2$ is a $C_1$-$C_6$alkylamino, such as NH—($CH_2$)$_3$$CH_3$,
$R^3$ is absent,
X is a phenylene,
Y is —NH—,
s=1, Z—R$^4$ is of Formula III, wherein:
n=0 or n=1 and R$^5$ is the specific side chain of an amino acid, such as —CH$_2$OH,
R$^4$ is a lipid of Formula V, wherein:
R$^7$ and R$^8$ are both a hydrogen atom,
R$^9$ and R$^{10}$ are independently from each other C$_1$-C$_{30}$alkyl, such as —COC$_{13}$H$_{27}$, —COC$_{15}$H$_{31}$, or —COC$_{17}$H$_{35}$; and
L$_1$ is absent and L$_2$ is —OC(O)—; or
L$_1$ is —OC(O)— and L$_2$ is —CH$_2$OC(O)—.
In another preferred embodiment of Formula II:
A is carbon,
R$^1$ is a H, or (C$_1$-C$_6$alkyl)-E-(C$_1$-C$_6$alkylene)-, wherein E is —O— or —NH—, such as —CH$_2$—NH—C$_2$H$_5$ or —CH$_2$—O—C$_2$H$_5$,
R$^2$ and R$^3$ form a fused C$_6$-C$_{20}$ aryl, preferably a phenyl,
X is an ethylene,
Y is —NH—,
s=1,
Z—R$^4$ is of Formula III as defined previously, wherein:
n=0 or n=1 and R$^5$ is the specific side chain of an amino acid, such as —CH$_2$OH, and
R$^4$ is a lipid of Formula V as defined previously, wherein:
R$^7$ and R$^8$ are both a hydrogen atom,
R$^9$ and R$^{10}$ are independently from each other C$_1$-C$_{30}$alkyl, such as —COC$_{13}$H$_{27}$, —COC$_{15}$H$_{31}$, or —COC$_{17}$H$_{35}$; and
L$_1$ is absent and L$_2$ is —OC(O)—; or
L$_1$ is —OC(O)— and L$_2$ is —CH$_2$OC(O)—.
In another preferred embodiment of Formula II:
A is carbon,
R$^1$ is a OH,
R$^2$ is CF$_3$, C$_1$-C$_{10}$alkylamino-C$_5$-C$_7$heterocycle such as —NH—CH$_2$—C$_5$-C$_7$heterocyclic group, in particular —NH—CH$_2$-tetrahydropyranyl or —NH—CH$_2$-tetrahydrofuranyl, or C$_1$-C$_{10}$alkoxy-C$_5$-C$_7$heterocycle such as —O—CH$_2$-C$_5$-C$_7$heterocyclic group, in particular —O—CH$_2$-tetrahydropyranyl or —O—CH$_2$-tetrahydrofuranyl,
R$^3$ is H,
X is an phenylene, or a pyridinylene,
Y is —NH—,
s=1, Z—R$^4$ is of Formula III as defined previously, wherein:
n=0 or n=1 and R$^5$ is the specific side chain of an amino acid, such as —CH$_2$OH,
R$^4$ is a lipid of Formula V as defined previously, wherein:
R$^7$ and R$^8$ are both a hydrogen atom,
R$^9$ and R$^{10}$ are independently from each other C$_1$-C$_{30}$alkyl, such as —COC$_{13}$H$_{27}$, —COC$_{15}$H$_{31}$, or —COC$_{17}$H$_{35}$; and
L$_1$ is absent and L$_2$ is —OC(O)—; or
L$_1$ is —OC(O)— and L$_2$ is —CH$_2$OC(O)—.
Another preferred embodiment of the compounds according to the present invention relates to compounds of Formula I or Formula II selected from the group consisting of:

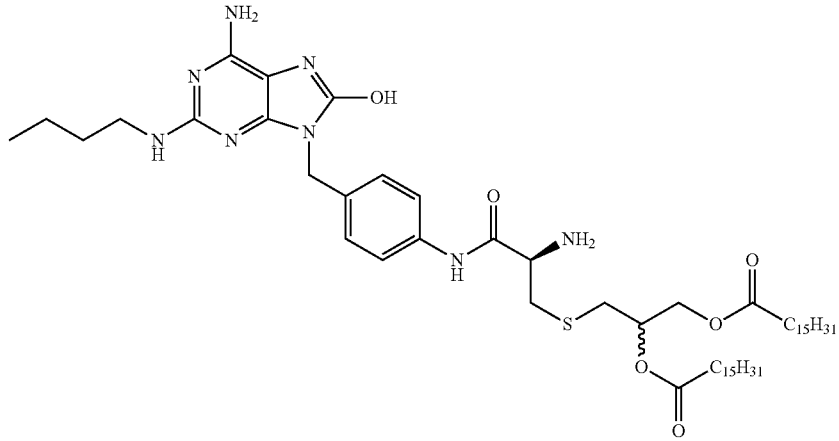

CL401

(R)-3-(2-amino-3-(4-((6-amino-2-(butylamino)-8-hydroxy-9H-purin-9-yl)methyl)phenyl amino)-3-oxopropylthio)propane-1,2-diyl dipalmitate,

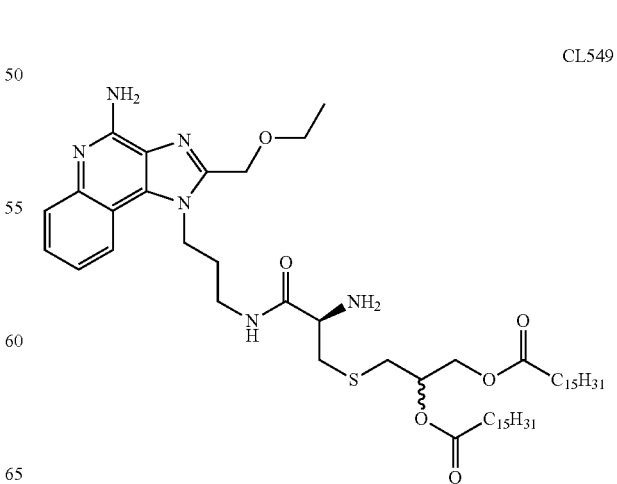

CL549

17

(R)-3-(2-amino-3-(3-(4-amino-2-(ethoxymethyl)-1H-imidazo[4,5-c]quinolin-1-yl)propyl amino)-3-oxopropylthio)propane-1,2-diyl dipalmitate,

CL550

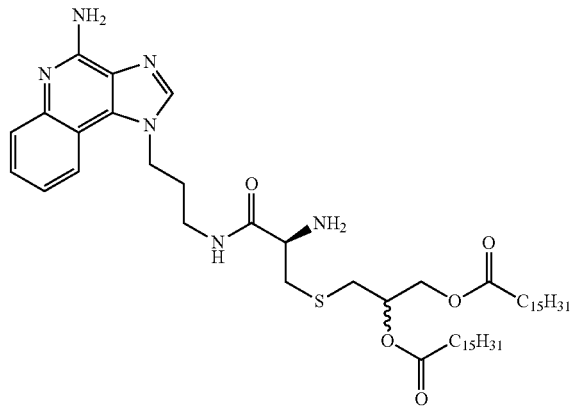

(R)-3-(2-amino-3-(3-(4-amino-1H-imidazo[4,5-c]quinolin-1-yl)propylamino)-3-oxopropylthio)propane-1,2-diyl dipalmitate,

CL551

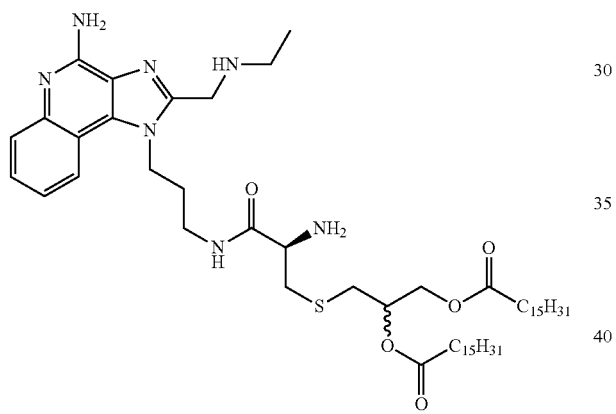

18

(R)-3-(2-amino-3-(3-(4-amino-2-((ethylamino)methyl)-1H-imidazo[4,5-c]quinolin-1-yl)propyl amino)-3-oxopropylthio)propane-1,2-diyl dipalmitate,

CL552

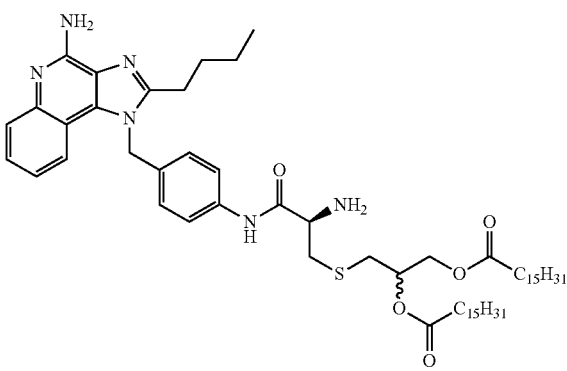

(R)-3-(2-amino-3-(4-((4-amino-2-butyl-1H-imidazo[4,5-c]quinolin-1-yl)methyl)phenyl amino)-3-oxopropylthio)propane-1,2-diyl dipalmitate,

CL453

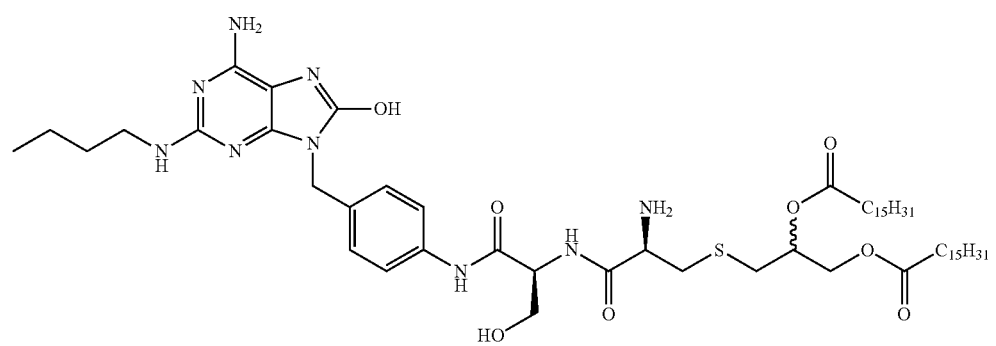

3-((R)-2-amino-3-((S)-1-(4-((6-amino-2-(butylamino)-8-hydroxy-9H-purin-9-yl)methyl)phenylamino)-3-hydroxy-1-oxopropan-2-ylamino)-3-oxopropylthio)propane-1,2-diyl dipalmitate,
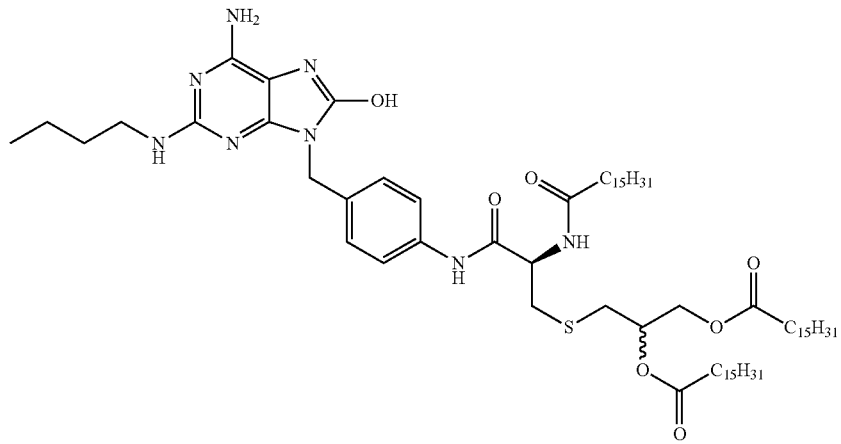
CL446
(R)-3-(3-(4-((6-amino-2-(butylamino)-8-hydroxy-9H-purin-9-yl)methyl)phenylamino)-3-oxo-2-palmitamidopropylthio)propane-1,2-diyl dipalmitate,
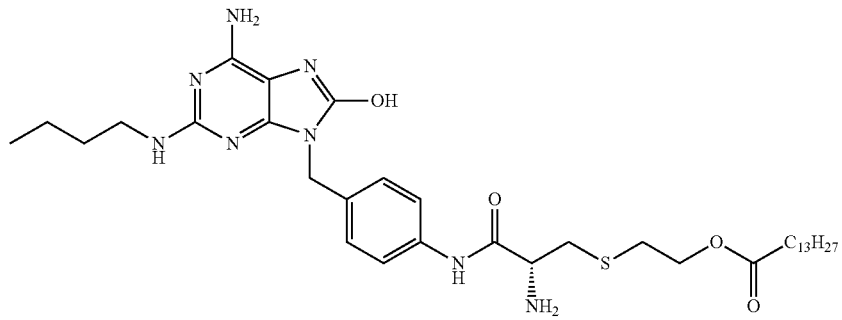
CL555
(R)-2-(2-amino-3-(4-((6-amino-2-(butylamino)-8-hydroxy-9H-purin-9-yl)methyl)phenylamino)-3-oxopropylthio)ethyl tetradecanoate,
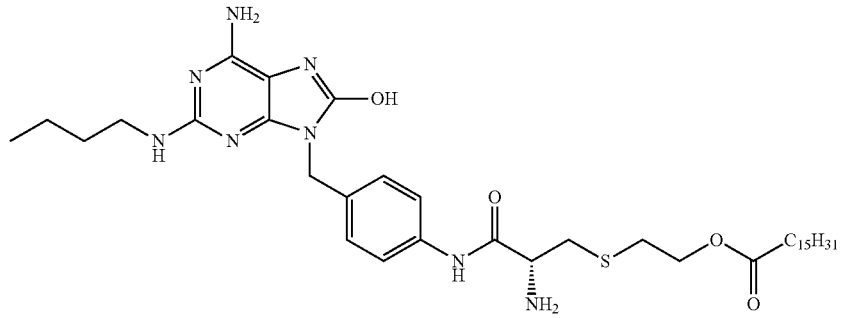
CL556

(R)-2-(2-amino-3-(4-((6-amino-2-(butylamino)-8-hydroxy-9H-purin-9-yl)methyl)phenylamino)-3-oxopropylthio)ethyl palmitate,
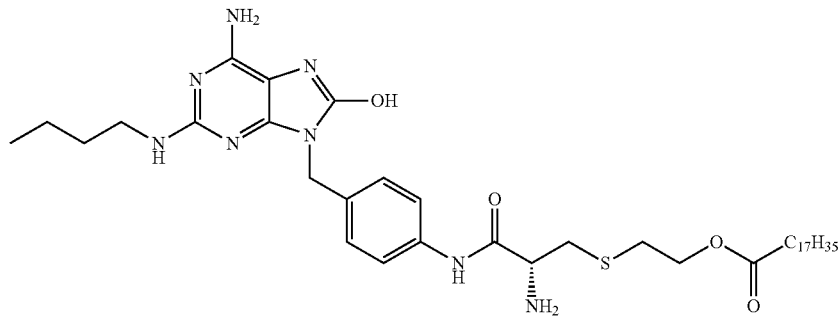
CL557
(R)-2-(2-amino-3-(4-((6-amino-2-(butylamino)-8-hydroxy-9H-purin-9-yl)methyl)phenylamino)-3-oxopropylthio)ethyl stearate,
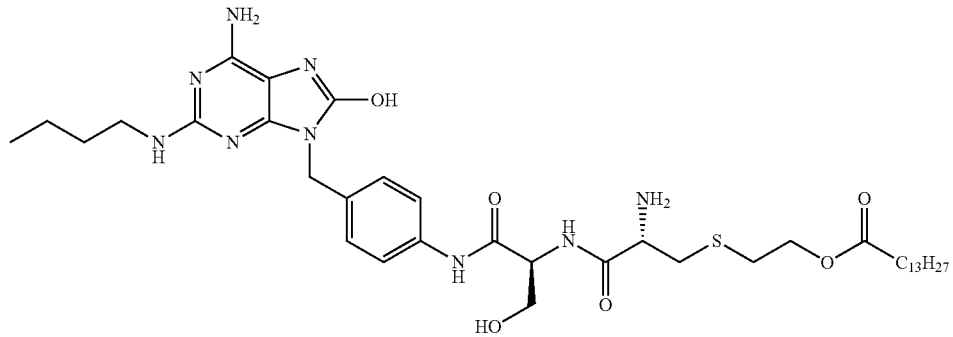
CL558
2-((S)-2-amino-3-((S)-1-(4-((6-amino-2-(butylamino)-8-hydroxy-9H-purin-9-yl)methyl)phenylamino)-3-hydroxy-1-oxopropan-2-ylamino)-3-oxopropylthio)ethyl tetradecanoate,
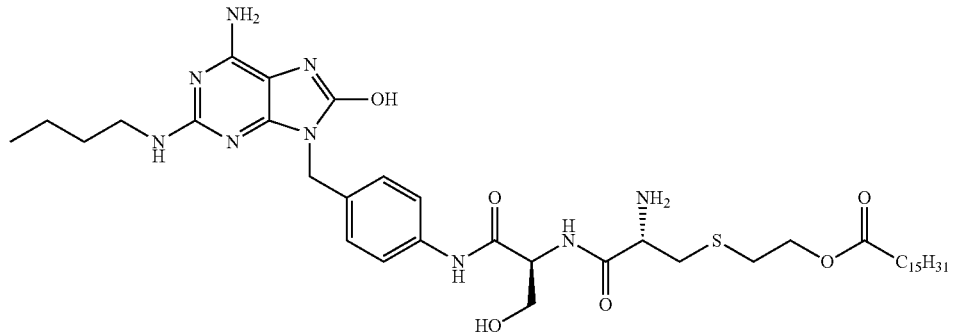
CL559

2-((S)-2-amino-3-((S)-1-(4-((6-amino-2-(buty-lamino)-8-hydroxy-9H-purin-9-yl)methyl)phe-nylamino)-3-hydroxy-1-oxopropan-2-ylamino)-3-oxopropylthio)ethyl palmitate,

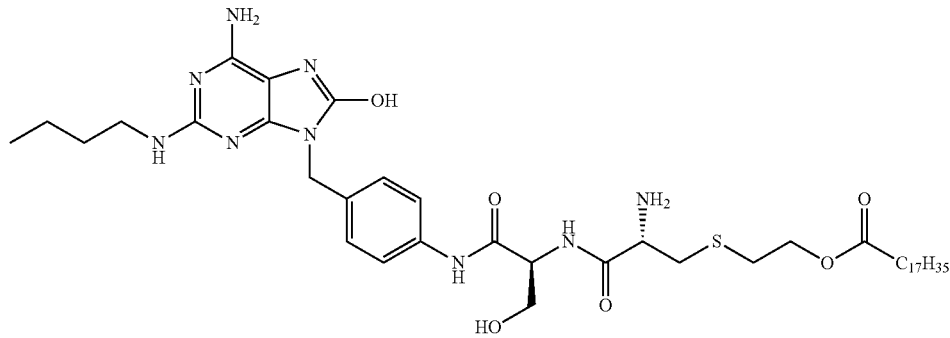
CL560

2-((S)-2-amino-3-((S)-1-(4-((6-amino-2-(buty-lamino)-8-hydroxy-9H-purin-9-yl)methyl)phe-nylamino)-3-hydroxy-1-oxopropan-2-ylamino)-3-oxopropylthio)ethyl stearate,

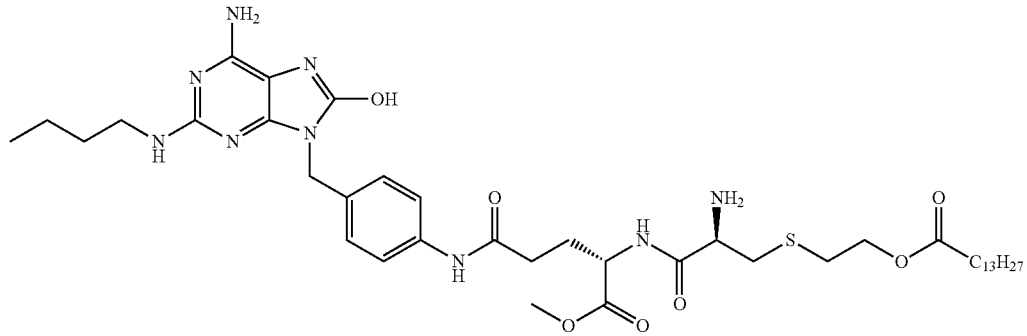
CL-572

2-((R)-2-amino-3-((S)-5-(4-((6-amino-2-(buty-lamino)-8-hydroxy-9H-purin-9-yl)methyl)phe-nylamino)-1-methoxy-1,5-dioxopentan-2-ylamino)-3-oxopropylthio)ethyl tetradecanoate, (R)-2-(2-amino-3-(3-(4-amino-2-(ethoxymethyl)-1H-imidazo[4,5-c]quinolin-1-yl)propyl amino)-3-oxopropylthio)ethyl stearate, and

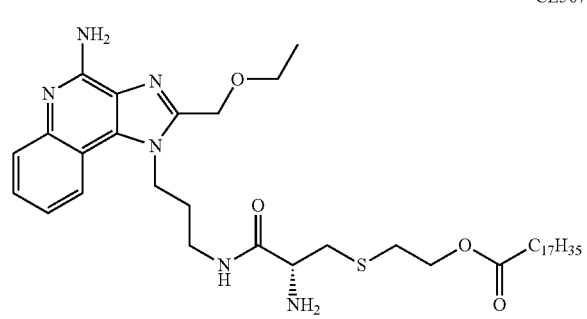
CL567

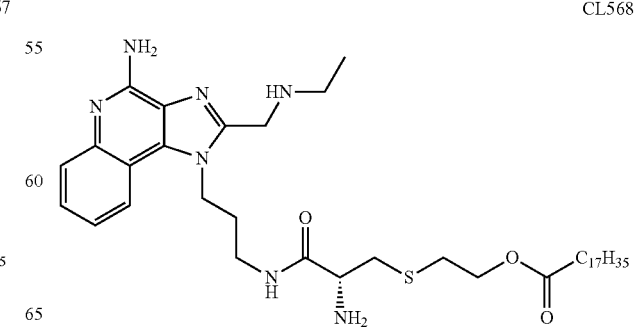
CL568

(R)-2-(2-amino-3-(3-(4-amino-2-((ethylamino)
methyl)-1H-imidazo[4,5-c]quinolin-1-yl)propy-
lamino)-3-oxopropylthio)ethyl stearate, a tautomer thereof or a pharmaceutically acceptable salt, solvate or polymorph of said compound or tautomer.

The conjugated compounds of Formula II containing one or more asymmetric carbon atoms can exist as two or more stereoisomers. Where a compound of Formula II contains an alkenyl or alkenylene group, geometric cis/trans (or Z/E) isomers are possible. Where structural isomers are interconvertible via a low energy barrier, tautomeric isomerism ('tautomerism') can occur. The invention includes the use of conjugated compound of TLR7 and/or TLR8 and TLR2 agonists. The conjugates may include acylated S-glyceryl-cysteine or acylated S-ethyl-cysteine linked to a TLR7 or TLR7/8 agonist via an amino acid linker.

The conjugated molecules of the invention may exist unsolvated or in solvated forms of pharmaceutically acceptable salts. The compounds of Formula I and their pharmaceutically acceptable salts, solvates and polymorphs are useful because they have pharmacological activity in animals, including humans. More particularly, they are useful in the immune modulation for the treatment of a disease. In one aspect, the compounds of the invention are useful in the treatment of viral, bacterial, fungal, and protozoal infections, tumors or cancer, or immunological diseases. In yet another aspect, the compounds of the invention are useful as vaccine adjuvants. Accordingly the invention provides a compound of Formula I or a pharmaceutically acceptable salt, solvate or derivative thereof for use as a medicament, in immune modulation for the treatment of a disease.

Another object of the present invention is a pharmaceutical composition comprising the conjugated compound of Formula I as defined previously and a pharmaceutically acceptable excipient or carrier.

A pharmaceutically acceptable excipient or carrier means an excipient or carrier that is useful in preparing a pharmaceutical composition that is safe, non-toxic and neither biologically nor otherwise undesirable, and includes and excipient that is acceptable for human use as well as veterinary use.

The conjugated compounds of the invention are typically provided in aqueous solutions which may contain excipients such as salts, carbohydrates and buffering agents (preferably to a pH from 3 to 9). For some applications, they may be more suitably formulated as a sterile non-aqueous solution or as a dried form to be used in conjunction with a suitable vehicle such as sterile, pyrogen-free water. The preparation of conjugated compounds of Formula I under sterile conditions, for example, by lyophilisation, may readily be accomplished using standard pharmaceutical techniques well known to those skilled in the art. Furthermore, the conjugated compounds of the invention can be formulated as other topical forms such as lotions, gels, emulsions or ointments etc.

Treatment

Another object the invention is a vaccine comprising the conjugated compound of Formula I as defined previously.

Another object of the present invention is a conjugated compound of Formula I as defined above for use in a therapeutic treatment in human or animals.

Another object of the present invention is a conjugated compound of Formula I as defined previously for use in the treatment of a pathology selected from the group consisting of an infection, a cancer and an immune disorder.

Another object of the present invention is a conjugated compound of Formula I as defined previously for use in the treatment of a pathology which may be alleviated by the induction of an immune response via TLR7 and/or TLR8, and TLR2 pathway(s).

The conjugated compounds of Formula I and their pharmaceutically acceptable salts, solvates and polymorphs are useful because they have pharmacological activity in animals, including humans. More particularly, they are useful in the treatment of a disorder in which the modulation, especially agonism, of TLR7 and/or TLR8 and/or TLR2 is implicated. In one aspect, the compounds of the invention are useful in the treatment of infections caused by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, or respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), a retrovirus (e.g., a lentivirus such as HIV) or a filovirus (e.g., Ebola virus or Marburg virus).

In another aspect, the conjugated compounds of the invention are useful to treat tumors or cancers including but not limited to carcinomas, sarcomas, and leukemia, e.g. skin cancers, squamous cell carcinoma, pancreatic carcinoma, hepatocarcinoma, renal cell carcinoma, Kaposi's sarcoma, melanoma, renal cell carcinoma, myelogeous leukemia, chronic lymphocytic leukemia, multiple myeloma, non-Hodgkin's lymphoma.

In yet another aspect, the conjugated compounds of the invention are useful to treat bacterial, fungal, and protozoal infections including but not limited to infections caused by bacteria of the genus *Escherichia, Enterobacter, Salmonella, Staphylococcus, Klebsiella, Proteus, Pseudomonas, Streptococcus, Chlamydia*, or fungal infections such as candidiasis, aspergillosis, histoplasmosis, cryptococcal meningitis.

In yet another aspect, the conjugated compounds of the invention are useful to treat Th2-mediated diseases, including but not limited to atopic diseases, such as atopic dermatitis or eczema, eosinophilia, asthma, allergy, allergic rhinitis In yet another aspect, the compounds of the invention are useful in the treatment of autoimmune diseases.

Another object of the present invention is a method for treating pathology selected from the group consisting of an infection, a cancer and an immune disorder in a subject in need thereof comprising administering to said subject a therapeutically effective amount of the conjugated compound of Formula I as defined previously.

Another object of the present invention is a method for inducing an immune response via:

TLR7 and/or TLR8 pathway(s); and/or

TLR2 pathway in a patient, comprising administering to said patient a therapeutically effective amount of the conjugated compound of Formula I as defined previously.

In a preferred embodiment, the method is for inducing an immune response via:

TLR7 and/or TLR8 pathway(s) and

TLR2 pathway in a patient.

Indeed, in the most preferred embodiment, the conjugated compound of Formula I is both an agonist of TLR7 and/or TLR8 and of TLR2. Thus, the conjugated compound of the invention may "activate" and/or be a positive modulator of the receptor(s) TLR7 and/or TLR8 and the receptor TLR2.

Another object of the present invention is the use of a conjugated compound of Formula I as defined previously for the preparation of a medicament for the treatment of an infection, a cancer or an immune disorder.

Methods of Administration

The therapeutically effective amount of the compound or Formula I as defined previously may be administered directly into the blood stream, into muscle, into tumor, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for administration include needle (including microneedle) injectors, needle-free injectors and infusion techniques. Compounds of the invention may be administered intratumorally. The preparation of intratumoral formulations under sterile conditions may readily be accomplished using standard pharmaceutical techniques well known to those skilled in the art.

In another embodiment, the therapeutically effective amount of the conjugated compound of Formula I as defined previously may also be administered topically as creams or as other topical forms known to those skilled in the art.

The dosage can vary within wide limits and will, of course, be fitted to the individual requirements in each particular case. In general, in the case of administration to adults a convenient daily dosage of the conjugated compound of the invention should be about 1 µg to about 500 mg, preferably about 100 µg to about 1 mg. The daily dosage may be administered as a single dose or in divided doses and, in addition, the upper dosage limit referred to earlier may be exceeded when this is found to be indicated.

Chemistry

The conjugated compounds of the present invention can be synthesized by an appropriate combination of generally well known synthetic methods. Techniques employed in synthesizing the compounds of the disclosure are both readily apparent and accessible to those of skill in the relevant art. The discussion below is offered to illustrate a number of the diverse methods available for use in assembling the compounds of the disclosure. However, the discussion is not intended to define the scope of reactions or reaction sequences that are useful in preparing the compounds of the present disclosure. The conjugated compounds of this disclosure may be made by the procedures and techniques disclosed in the Examples section below, as well as by known organic synthesis techniques.

The conjugated compounds of the present disclosure may be synthesized using one or more protecting groups generally known in the art of chemical synthesis. The term "protecting group" refers to chemical moieties that block some or all reactive moieties of a compound and prevent such moieties from participating in chemical reactions until the protective group is removed. Examples of the moieties listed are described in 'Protective Groups in Organic Synthesis' by Green and Wuts, third edition, (John Wiley and Sons, 1999). Where different protecting groups were employed, each (different) protecting group was removable by a different means. Protective groups that were cleaved under totally disparate reaction conditions allowed for differential removal of such protecting groups. For example, protective groups can be removed by acid, base, and hydrogenolysis.

An object of the present invention is a process for the manufacture of the compounds of Formula I as defined previously, which comprises reacting a compound of Formula VI:

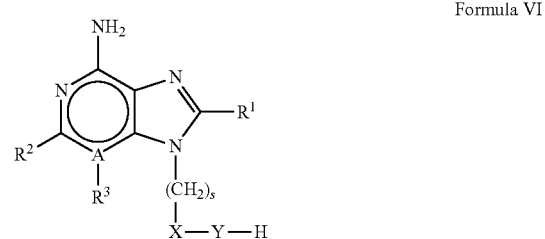

Formula VI wherein $R^1$, $R^2$, $R^3$, A, s, and X are as defined previously, with a compound of Formula VII:

H—Z—$R^4$   Formula VII wherein Z and $R^4$ are as defined previously, or reacting a compound of formula VIII:

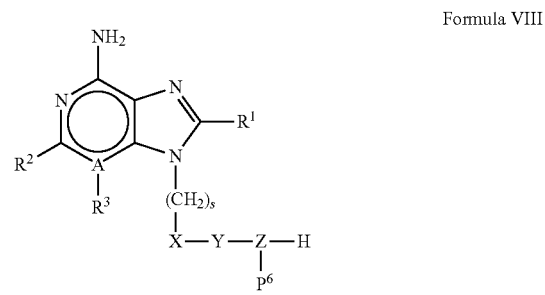

Formula VIII wherein R', $R^2$, $R^3$, A, s, X, Y and Z are as defined above, and $P^6$ is a protecting group, with a compound of Formula IX:

HO—$R^4$   Formula IX wherein $R^4$ is as defined above, followed by a deprotection step.

These processes provide:

TLR7/TLR2 purine derivatives of Formula X:

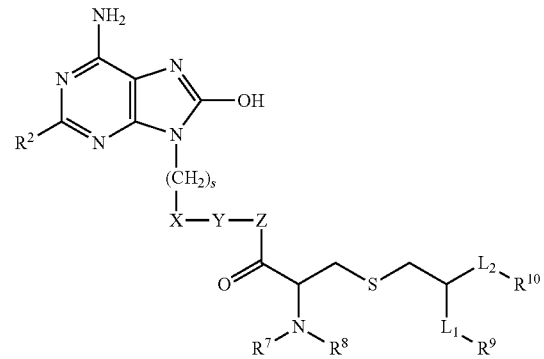

Formula X

TLR7 and/or TLR8/TLR2 imidazoquinoline derivatives of Formula XI:

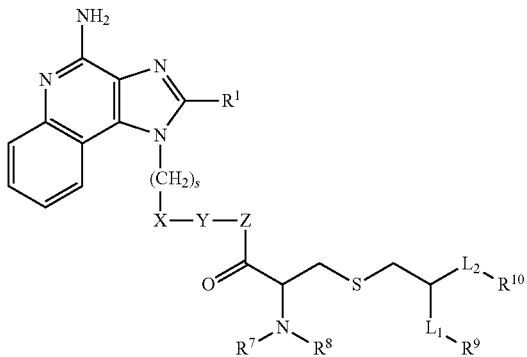

Formula XI

TLR7 and/or TLR8/TLR23-deazapurine derivatives of Formula XII:

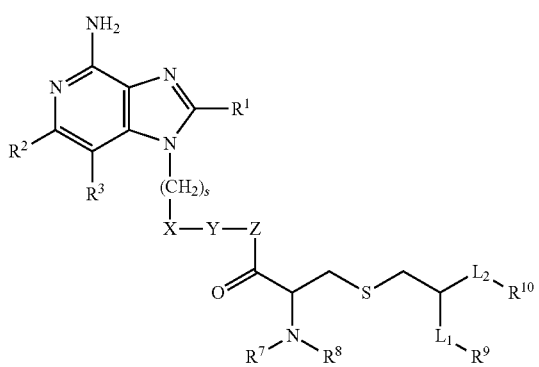

Formula XII

The compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

In particular, a compound of Formula $X_A$ is the tautomer of the compound of Formula $X_B$:

Scheme 1

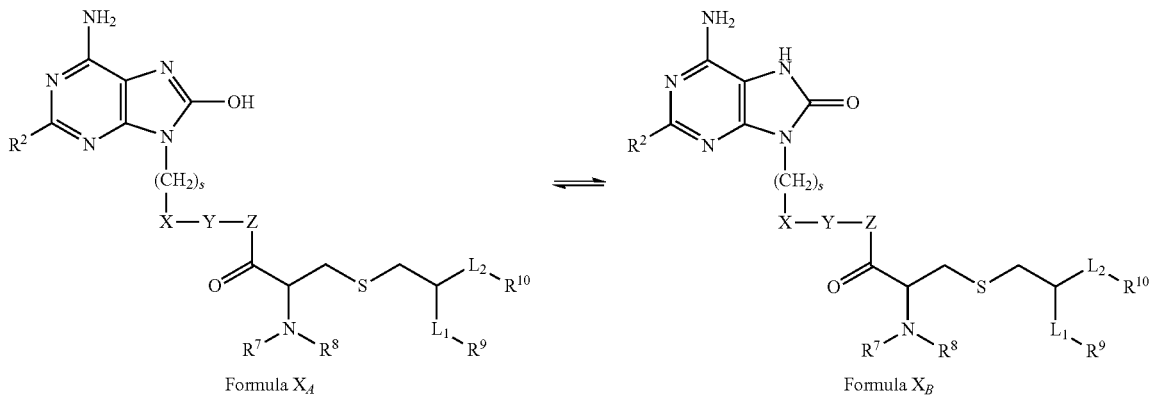

Formula $X_A$

Formula $X_B$

It will be appreciated by those skilled in the art that certain of the procedures described in the schemes for the preparation of compounds of Formula I or intermediates thereof may not be applicable to some of the possible substituents. It will be further appreciated by those skilled in the art that it may be necessary or desirable to carry out the transformations described in the schemes in a different order from that described, or to modify one or more of the transformations, to provide the desired compound of Formula I.

It will be still further appreciated by those skilled in the art that it may be necessary or desirable at any stage in the synthesis of compounds of Formula I to protect one or more sensitive groups in the molecule so as to prevent undesirable side reactions. In particular, it may be necessary or desirable to protect amino groups. The protecting groups used in the preparation of compounds of Formula I may be used in conventional manner. See, for example, those described in 'Protective Groups in Organic Synthesis' by Green and Wuts, third edition, (John Wiley and Sons, 1999), in particular chapter 7, pages 494-653 ("Protection for the Amino Group"), incorporated herein by reference, which also describes methods for the removal of such groups.

The TLR2 agonist lipid derivatives of Formula V as described previously can be prepared according to reaction Scheme 2 to provide the compounds HO—$R^4$ of Formulas 9 or 12:

Scheme 2
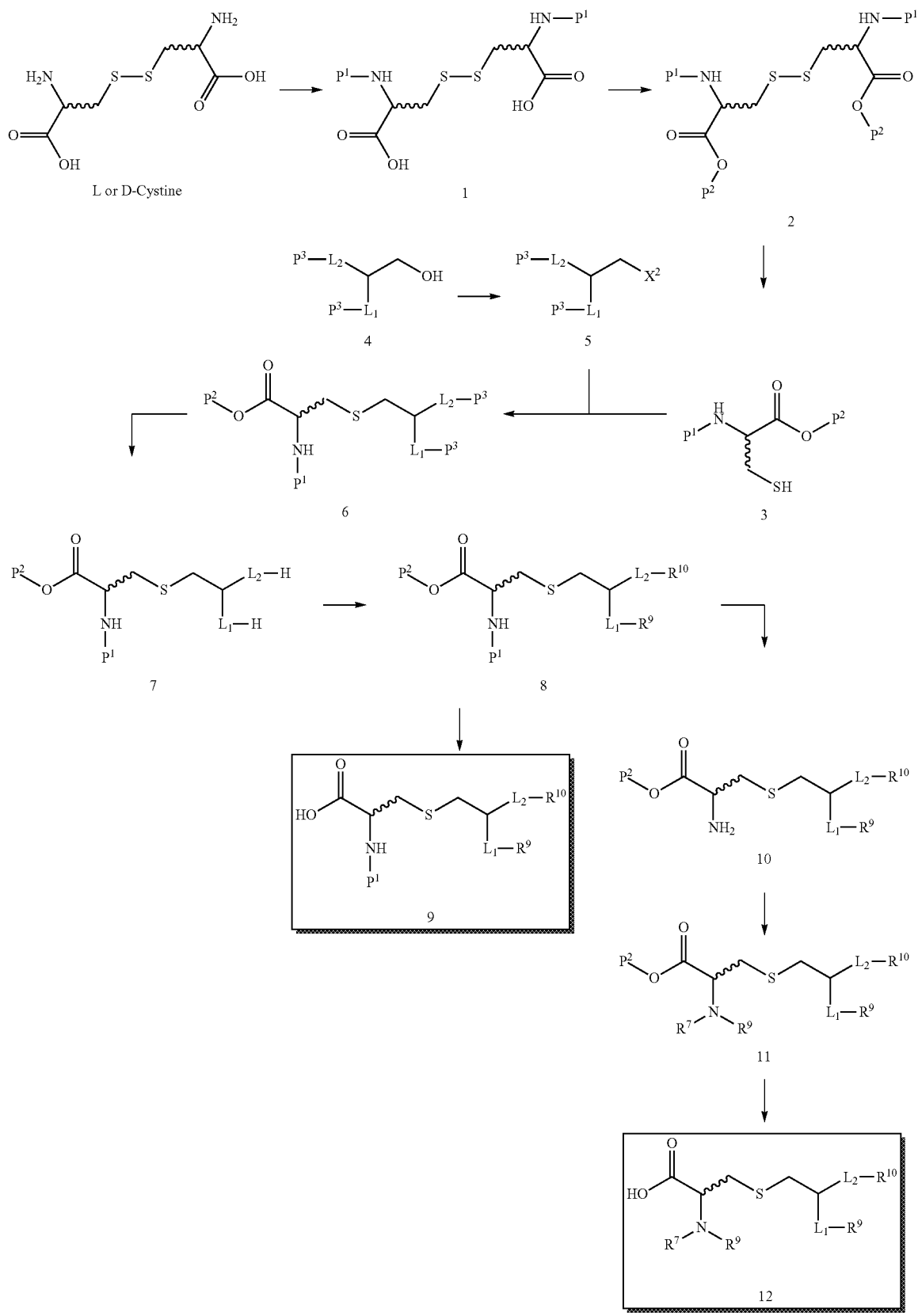

In the above formulas, $X^2$ is halogen or leaving group $P^1$, $P^2$, $P^3$ are different protecting groups, $L_1$, $L_2$, $R^7$, $R^8$, $R^9$, and $R^{10}$ are as defined previously.

The amine function of the commercially available L or D-Cystine can be, suitably, protected as known in the peptide art. For example, the tert-butoxycarbonyl (Boc) group is preferred for protection of the two amino group at the a position of the cystine to provide the compound 1.

The carboxylic acid function of compound 1 can be, then, protected by conventional methods. Typically, the carboxylic acid is treated with an alcohol in the presence of an acid catalyst. Alternatively, the carboxylic acid may be converted to an activated salt, such as a cesium salt, and treated with an alkyl or alkylene halide. In the practice of this invention the acid is protected with the allylic group. Typically, the acid or a salt thereof is reacted with the allyl bromide or iodide in a polar aprotic solvent such as dimethylformamide to provide compound 2.

The disulphide bond of the correctly protected cystine 2 can be reduced with $PBu_3$, DTT, or other suitable reductant to give the free thiol 3.

The primary hydroxyl group of the correctly protected glycerol 4 (wherein L1 is —CH2-O— and L2-O) can be easily converted into an eliminable group, for example a sulphonyloxy group, by reaction with a methanesulphonyl chloride in the presence of triethylamine in dichloromethane or of p-toluenesulphonyl chloride in pyridine. Preferably, the selective activation of the primary alcohol is carried out to halogenation type reactions which are practically prepared by reaction with iodide, triphenylphosphine, and imidazole (Garegg, P. J. et al., J. Chem. Soc. Perkin 1, 681 1982). This reaction provides the compound 5 in which $X^2$ is an iodine atom.

The condensation reaction between compound 3 and 5 in presence of base (for example triethylamine in DMF) provides totally protected the thioethanol or thioglycerol motif with the cysteine compound 6.

The protection on glycerol moiety can be, then, selectively removed to provide the compound 7.

The alcohol function of compound 7 can be, preferably, acylated. The reaction is carried out by adding a fatty acid to a solution of the compound 7 dissolved in a suitable organic solvent, such as dichloromethane, in the presence of a suitable catalyst, such as ethyldimethylaminopropylcarbodiimide (EDCI)-DMAP to provide diacylester 8.

The carboxylic protection of compound 8 can be removed by acid, base or hydrogenolysis. In the case of the allylic ester protecting group, the organic soluble palladium complex is used. The complex of choice is tetrakis (triphenylphosphine)palladium-(0). Other utilizable soluble palladium complexes are palladium(II), dichloro-di[benzonitrile]palladium(II) and palladium(II) diacetate in conjunction with several equivalents of triphenylphosphine (see Fieser and Fieser, "Reagents for Organic Synthesis", Vol V, pp. 497, 503, 504). The quantity of catalyst utilized in the process of this invention is typically 0.25-5 mole percent of the allylic ester. This reaction provides the compound 9 which can be used as $R_4$—OH derivatives.

Alternately, the protection of the amino group of compound 8 can be removed. Preferably, the Boc group is cleaved with HCl in organic solvents or with TFA in organic solvents. This reaction provides the compound 10.

The free amine function of compound 10 can be, then, acylated. The N-acylated compound can be prepared using acylating reagents such as organic acid halides or organic acid anhydrides or using fatty acid with a coupling reagent such as DCC, CDI, EDC, or optionally with a tertiary amine base and/or catalyst, e.g., DMAP. Preferably, fatty acid is introduced on amine of compound 10 using a coupling agent such as HATU in the presence of an amine such as DIEA in polar solvent such as DMF or dichloromethane to provide compound 11.

The carboxylic protection of compound 11 can be removed to provide compound 12 as described below for compound 9. The compound 12 can be used as $R_4$—OH derivatives.

The TLR2 agonist of Formula III and IV as described previously can be prepared according to reaction Scheme 3 to provide the compounds H—Z—$R^4$ of Formula 15 or 16:

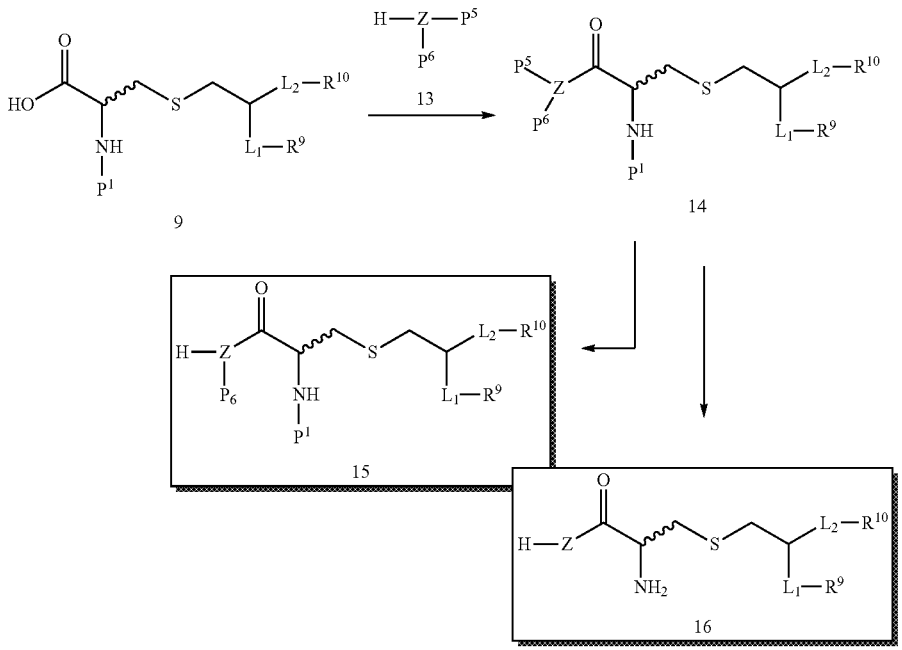

Scheme 3

In the above formulas, $P^1$, $P^5$, $P^6$ are different protecting groups, $L_1$, $L_2$, $R^7$, $R^8$, $R^9$, and $R^{10}$ are same as defined previously.

The compound 14 is prepared from respectively compounds 9 and 13 by any well-known peptide synthesis procedure in the art. The most commonly employed methods for peptide bond formation in solution include: the carbodiimide method (DCC, DIC), symmetric or mixed anhydrides, active esters (OPfp, Odhbt, OSu), phosphonium salts (BOP, PyBOP, AOP, PyAOP) and uronium/guanidinium-mediated salt built around processes using HOBt and HAOt (HBTU, HATU, HBPyU, COMU etc). HATU reacts exclusively with carboxylate salts (R—COO—); mixtures of HATU and a carboxylic acid (R—COOH) remain stable. This procedure eliminates the requirement for a separate neutralization step saving time and minimizing diketopiperazine formation. Three equivalents of base (DIEA or NMM) are necessary to neutralize the carboxylic acid, the amine salt, and the acidic hydroxybenzotriazole. When using HATU, the reaction mixture has to be kept near basic pH in order to ensure a fast coupling. Under such conditions, the coupling rate is so high that racemization is negligible using urethane-protected amino acid couplings and fairly low in segment coupling. The excess of acid and "onium" salt (HATU) is typically 1.1 molar equivalent in solution synthesis. This reaction is preferably carried out in a solvent such as methylene chloride, chloroform, tetrahydrofuran, dioxane, ethyl acetate, or the like under ice-cooling to at ambient temperature and the reaction in the presence of an inert gas is usually carried out in an anhydrous, but not critical, conditions. The reaction temperature is selected from the range between about room temperature and around boiling point of the solvent.

The protection $P^5$ on compound 14 can be removed selectively by acid, base or hydrogenolysis to afford the compound 15. The compound 15 can be used as H—Z—$R^4$ derivatives.

The total deprotection of compound 14 by acid, base or hydrogenolysis can afford the compound 16. The compound 16 can be used as H—Z—$R^4$ derivatives.

The purine derivatives of Formula X can be prepared by the following methods. The starting compounds not disclosed below can be prepared by a similar method to the following method or by a known method and similar methods to that.

Scheme 4

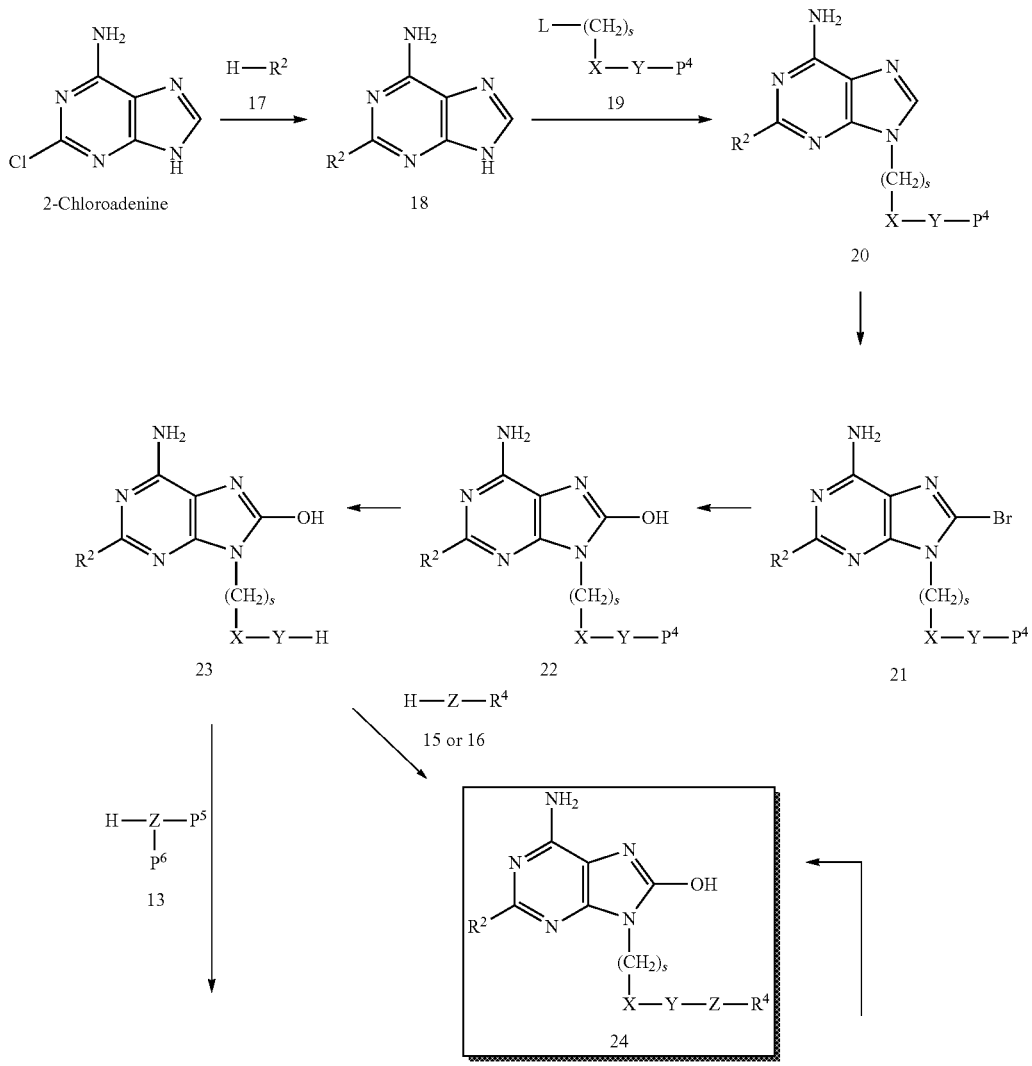

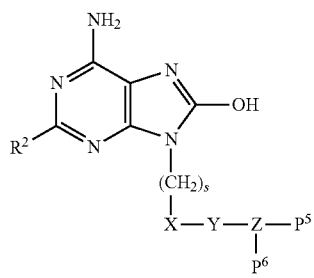

25

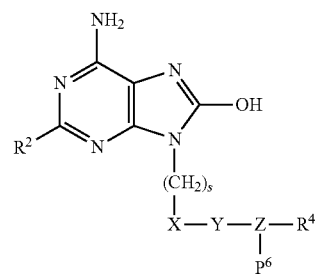

27

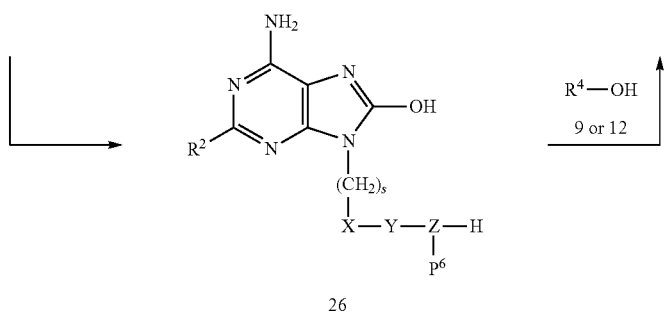

26

In the above formulas, L is a leaving group, $P^4$, $P^5$ and $P^6$ are different protecting groups $R^2$, s, X, Y, Z and $R^4$ are as defined previously.

Commercially available 2-Chloroadenine can be reacted with compound 17 in an organic solvent. When compound 17 is an amine, the reaction is preferably carried out in the amine as solvent. Reaction vessels such as an autoclave etc. may be used in the reaction, if necessary. When compound 17 is alcohol or thioalcohol, the reaction is preferably carried out in the presence of a base. The bases are alkali metals, such as sodium or potassium, alkali metal hydrides, such as sodium hydride or potassium hydride, organometalic compounds, such as methyl lithium, butyl lithium or lithium diisopropylamide. The base is preferably used about equimolar to compound 17. The organic solvents are aprotic solvents, such as dimethylformamide, acetonitrile or hexamethylphosphoroustriamide, or ethers such as diethyl ether, tetrahydrofuran or 1,4-dioxane or diglyme. The reaction temperature is selected from the range between about room temperature and around the boiling point of the solvent.

The chlorine atom of 2-chloroadenine can be also coupled under a variety of conditions in which a reactive organometallic reagent can be treated with 2-chloroadenine in the presence of a transition metal catalyst, for example a stannane, zincate or boronic acid in the presence of a palladium catalyst, to give the 2-substituted adenine 18.

Compound 18 and compound 19 can react in the presence of a base in an organic solvent. Compound 19 can be used about equal molar or several molars to compound 18. Bases are inorganic bases such as alkali metal carbonates (e.g. sodium carbonate, potassium carbonate, cesium carbonate), or organic bases, such as tertiary amines (e.g. triethylamine, diisopropylethylamine) or pyridines (e.g. 4-dimethylaminopyridine, pyridine). The base is preferably used about equimolar to compound 19. The organic solvents are halogenated hydrocarbons such as tetrachloromethane, chloroform or methylene chloride, ethers such as diethyl ether, tetrahydrofuran or 1,4-dioxane, or aprotic solvents, such as dimethylformamide, dimethyl sulfoxide, acetonitrile or hex-amethylphosphoroustriamide. The reaction temperature is selected from the range between about 0° C. and around the boiling point of the solvent.

Compound 20 can react with a brominating reagent such as bromine, hydrobromic acid perbromide, N-bromo succinimide, etc. in an organic solvent. A reaction promoter such as sodium acetate may be added to the reaction mixture. The brominating reagent is used from equimolar to several moles of compound 20, preferably from equimolar to one and one-half moles. The organic solvents are halogenated hydrocarbons, such as tetrachloromethane, chloroform or methylene chloride, ethers such as diethyl ether, acetic acid, or carbon disulfide. The reaction temperature is selected from the range between about 0° C. and around boiling point of the solvent.

Compound 21 can react with an alcohol such as methanol in the presence of a base in an organic solvent. The bases are alkali metals, such as sodium or potassium, alkali metal hydrides, such as sodium hydride or potassium hydride, organometallic compounds, such as methyl lithium, butyl lithium or lithium diisopropylamide. The base is preferably used from about equal molar to about two times as much to compound 21. The organic solvents are ethers, such as diethyl ether, tetrahydrofuran or 1,4-dioxane, or aprotic solvents, such as dimethylformamide, dimethyl sulfoxide, acetonitrile or hexamethylphosphoroustriamide. The alcohol as the reagent, such as methanol, ethanol, propanol or butanol may serve as a solvent. The reaction temperature is selected from the range between about room temperature and around boiling point of the solvent. This intermediate can be hydrolysed under either acidic or basic conditions, typically with an acid in water or a mixture of water and an organic solvent. The acids are inorganic acids, such as hydrochloric acid or hydrobromic acid, or organic acids such as trifluoroacetic acid. The organic solvents are ethers, such as diethyl ether or tetrahydrofuran, aprotic solvents such as dimethylformamide, alcohols, such as methanol, ethanol or propanol, or acetic acid. The reaction temperature is selected from the range between about room temperature and around boiling point of the solvent.

The protection on compound 22 can be removed by acid, base or hydrogenolysis.

The compounds 24 and 25 are prepared from compound 23 and respectively compounds 15 or 16 and 13 by any well-known peptide synthesis as described previously for compound 14. The protection $P^5$ on compound 25 can be removed selectively by acid, base or hydrogenolysis to afford the compound 26.

Compound 26 and compounds 9 or 12 can react by any well-known peptide synthesis as described previously for compound 14.

The protection on compound 27 can be removed by acid, base or hydrogenolysis to afford the desired compound 24.

Imidazoquinolines derivatives of Formula XI of the invention can be prepared according to reaction Scheme 5:

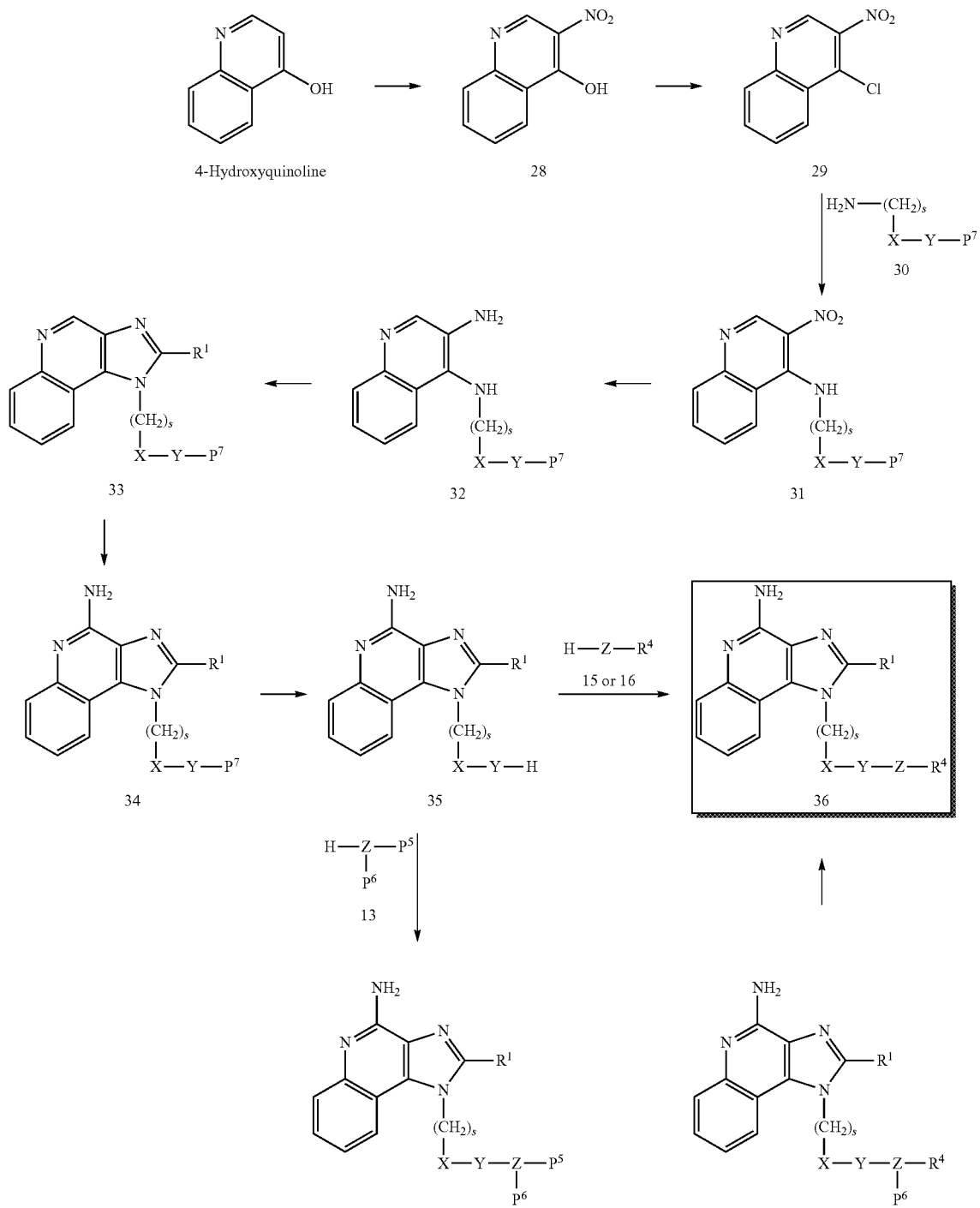

-continued

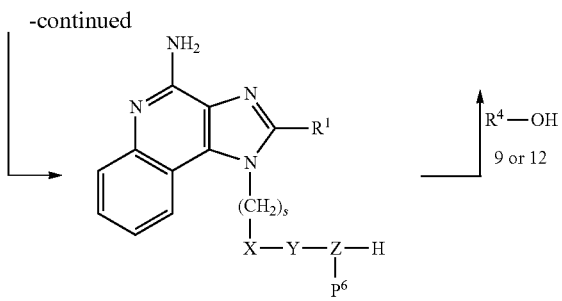

38

In the above formulas P⁷ is a protecting group P⁵, P⁶, L, R¹, R⁴, s, X, Y, and Z are as defined previously.

The reaction scheme begins with a commercially available 4-hydroxyquinoline. The nitration of a 4-hydroxyquinoline provide the 3-nitro-4-hydroxyquinoline compound 28. Conventional conditions for such reactions are well known. Preferred conditions in the instance afford a product of Formula 28 in superior yield compared with conditions used in the prior art, involve heating at about 125° C.-130° C. in propionic acid in the presence of nitric acid.

Compound 28 is chlorinated at the 4-position to provide a 3-nitro-4chloroquinoline compound 29. Preferred conditions involve chlorination in methylene chloride with a Vilsmeier reagent prepared from thionyl chloride and N,N-dimethylformamide. In such a reaction, the compound of Formula 28 is suspended in methylene chloride, and a slight molar excess of thionyl chloride and N,N-dimethylformamide is added to the suspension. Heating to reflux facilitates the chlorination.

Compound 29 is reacted with an amine of Formula 30. The reaction can be carried out by adding amine to a solution of compound 29 in a suitable solvent such as chloroform or dichloromethane in presence of base such as triethylamine or diisopropyl-ethylamine and optionally heating.

Compound 31 is reduced to provide a quinoline-3,4-diamine compound 32. Compound 31 may then be reduced under any of the conditions known in the literature to reduce a nitro aromatic compound to an amine using for example iron or tin in HCl, hydrogenation in the presence of a transition metal catalyst such as palladium, platinum or nickel or a chemical reductant such as lithium aluminium hydride to give 32. Preferably, the reduction is carried out using a conventional heterogeneous hydrogenation catalyst such as platinum on carbon or palladium on carbon. The reaction can conveniently be carried out in a suitable solvent such as ethanol, isopropyl alcohol or toluene.

Compound 32 is reacted with a carboxylic acid or an equivalent thereof to provide a 1H-imidazo[4,5-c]quinoline compound 33. Suitable equivalents to carboxylic acid include acid halides, orthoesters, and 1,1-dialkoxyalkyl alkanoates. The carboxylic acid or equivalent is selected such that it will provide the desired R¹ substituent in a compound 33. For example, triethyl orthoformate will provide a compound where R¹ is hydrogen and triethyl orthoacetate will provide a compound where R¹ is methyl. The reaction can be run in the absence of solvent or in an inert solvent such as toluene. The reaction is run with sufficient heating to drive off any alcohol or water formed as a byproduct of the reaction.

Compound 33 is oxidized to provide a 1H-imidazo[4,5-c]quinoline-5N-oxide using a conventional oxidizing agent that is capable of forming N-oxides. Preferred reaction conditions involve by reacting a solution of a compound 33 in chloroform with 3-chloroperoxybenzoic acid at ambient conditions. The intermediate 1H-imidazo[4,5-c]quinoline-5N-oxide is then directly aminated to provide a 1H-imidazo[4,5-c]quinolin-4-amine compound 34. In this step the N-oxide compound is reacted with an acylating agent such as: alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. The product obtained is mixed with an excess of an aminating agent. Suitable aminating agents include ammonia (e.g., in the form of ammonium hydroxide) and ammonium salts (e.g., ammonium carbonate, ammonium bicarbonate, ammonium phosphate) Ammonium hydroxide is preferred. The reaction is preferably carried out by dissolving the N-oxide compound in an inert solvent such as dichloromethane, adding the aminating agent to the solution, and then slowly adding the acylating agent. The product or a pharmaceutically acceptable salt thereof can be isolated using conventional methods.

The protection on compound 34 can be removed by acid, base or hydrogenolysis to provide compound 35.

The compounds 36 and 37 are prepared from compound 35 with respectively compounds 15 or 16 and 13 by any well-known peptide synthesis procedure in the art as described above for compound 14.

The protection P⁵ on compound 37 can be removed selectively by acid, base or hydrogenolysis to provide the compound 38.

Compound 38 and compounds 9 or 12 can react by any well-known peptide synthesis procedure in the art as described above for compound 14.

The protection on compound 39 can be removed by acid, base or hydrogenolysis to provide compound 36.

3-deazapurine derivatives of Formula XII of the invention can be prepared according to reaction Scheme 6:

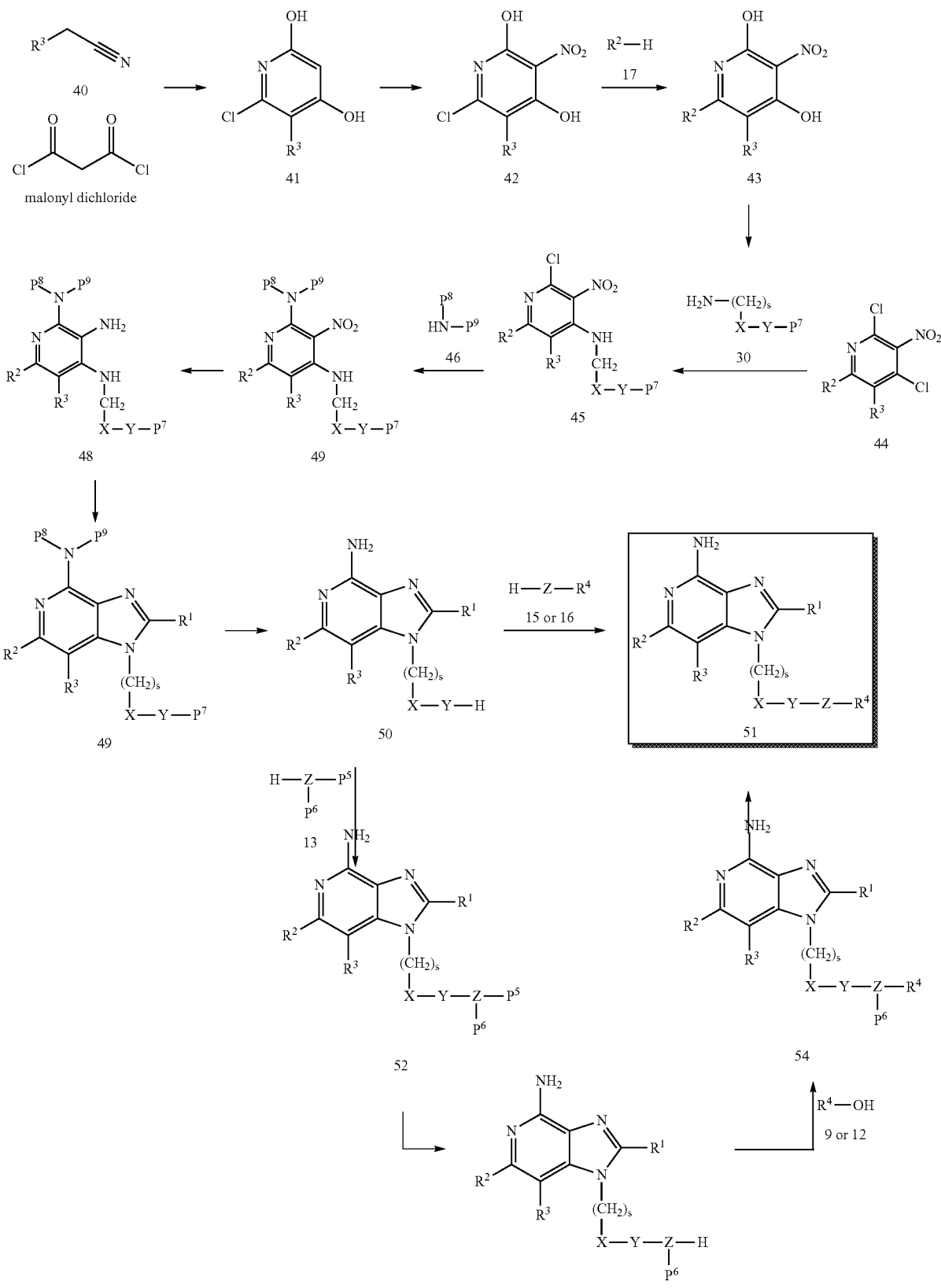
Scheme 6

In the above formulas, $P^8$ and $P^9$ are different protecting groups, $P^5$, $P^6$, $P^7$, L, $R^1R^2$, $R^3$, $R^4$, s, X, Y, and Z are as defined previously.

A commercially available nitrile 40 which possesses a methylene group adjacent to the nitrile function is reacted with malonyl dichloride to provide the pyridines 41. (Synthesis, 1984, 765-766).

The pyridines 41 is then nitrated using method described above for the 4-hydroxyquinoline.

The chlorine atom of compound 42 is then reacted with compound 17 as described above for the preparation of compound 18.

Compound 43 is chlorinated using a variety of conditions which convert hydroxyl groups to chlorines, such as thionyl chloride or phosphorus oxychloride to give 44. Preferred condition is described above for the preparation of compound 29.

Compound 44 is reacted with an amine of general Formula 30, as described above for the preparation of compound 31. This amine preferentially reacts at the 4-chloro group to give 45. Some displacement of both chlorine groups or a minor amount of displacement at the 2-chloro group can occur, but does not detract from the ability to secure predominantly compound 45.

Compound 45 is then reacted with ammonia $P^8$=$P^9$=H in methanol at 150° C. under pressure to give compound 47. Alternatively, compound 45 can be reacted with a protected form of ammonia 46, in which $P^8$ and $P^9$ protecting group which can later removed under mild conditions, such as dibenzylamine or diallylamine.

The compound 47 is then reduced under conditions as described above for compound 31 to give compound 48.

Compound 48 is then reacted with a source of C=0 such as 1,1-carbonyldiimidazole or phosgene. Alternatively, compound 48 can be reacted with a carboxylic acid or an equivalent, as described for compound 32, to provide a 1H-imidazo[4,5-c]pyridine compound 49.

The protection on compound 49 can be removed by acid, base or hydrogenolysis to provide compound 50.

The compounds 51 and 52 are prepared from compound 50 with respectively compounds 15 or 16 and 13 by any well-known peptide synthesis procedure in the art as described above for compound 14.

The protection $P^5$ on compound 52 can be removed selectively by acid, base or hydrogenolysis to provide compound 53.

Compound 53 and compounds 9 or 12 can react by any well-known peptide synthesis procedure in the art as described above for compound 14.

The protection on compound 54 can be removed by acid, base or hydrogenolysis to provide compound 51.

BRIEF DESCRIPTION OF THE DRAWINGS

The invention will be further illustrated by the following figures and examples. However, these examples and figures should not be interpreted in any way as limiting the scope of the present invention.

FIGURES

Figure 1A:
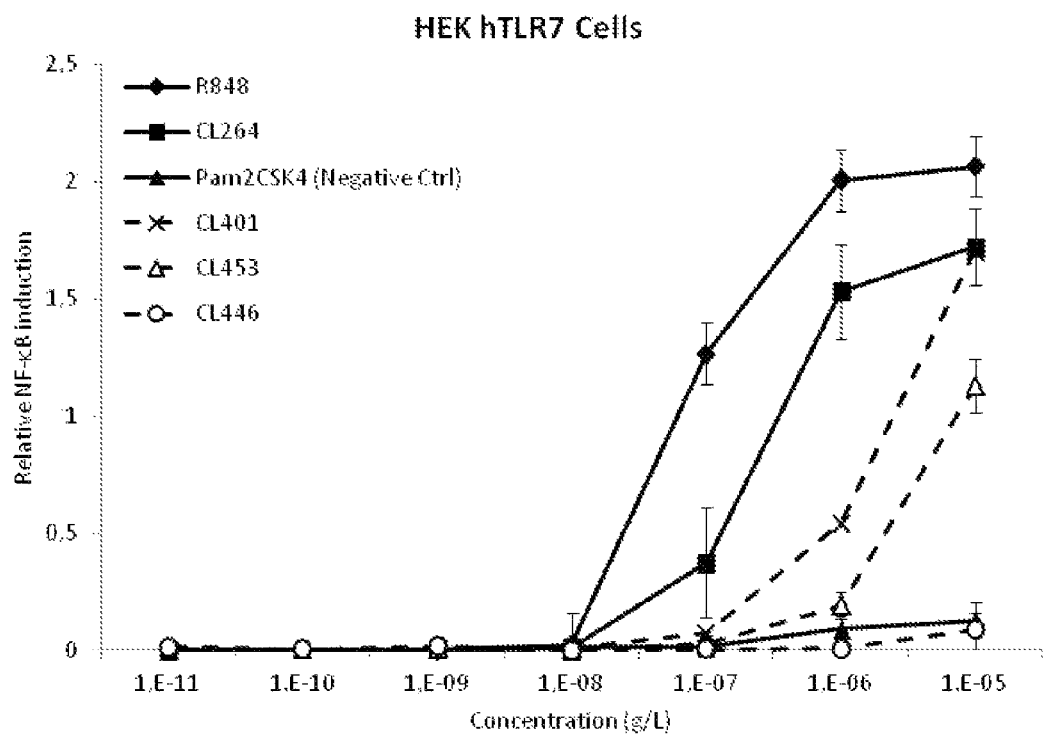
FIG. 1A is a graphical representation of the activity of di- or tri-acylated molecules of the invention towards human TLR7.
Figure 1B:
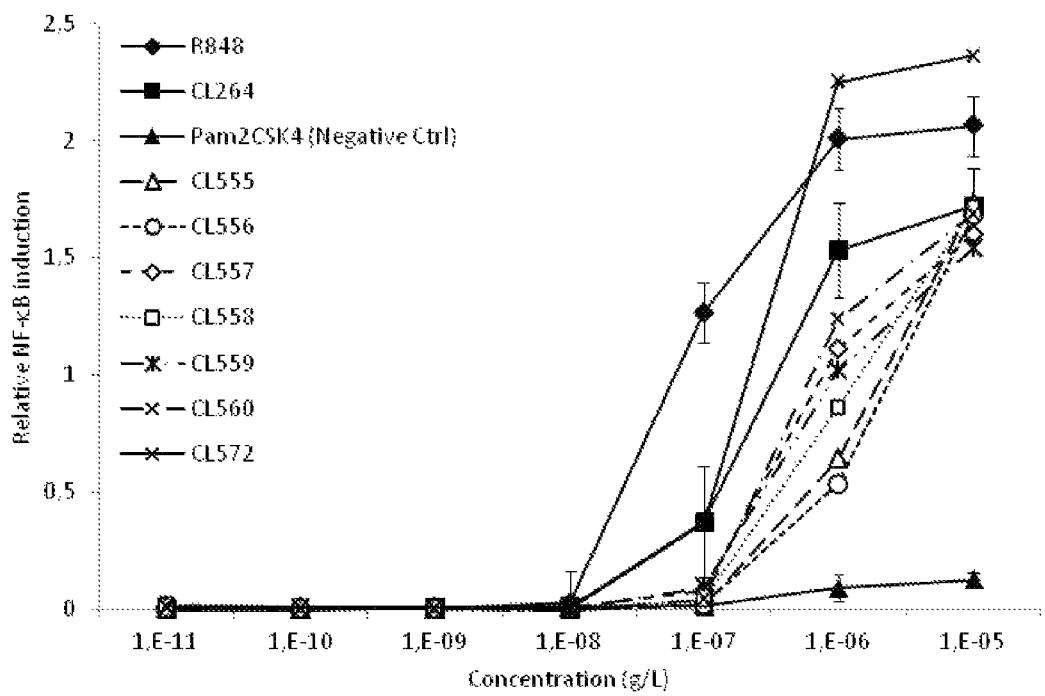
FIG. 1B is a graphical representation of the activity of mono-acylated molecules of the invention towards human TLR7.
Figure 2A:
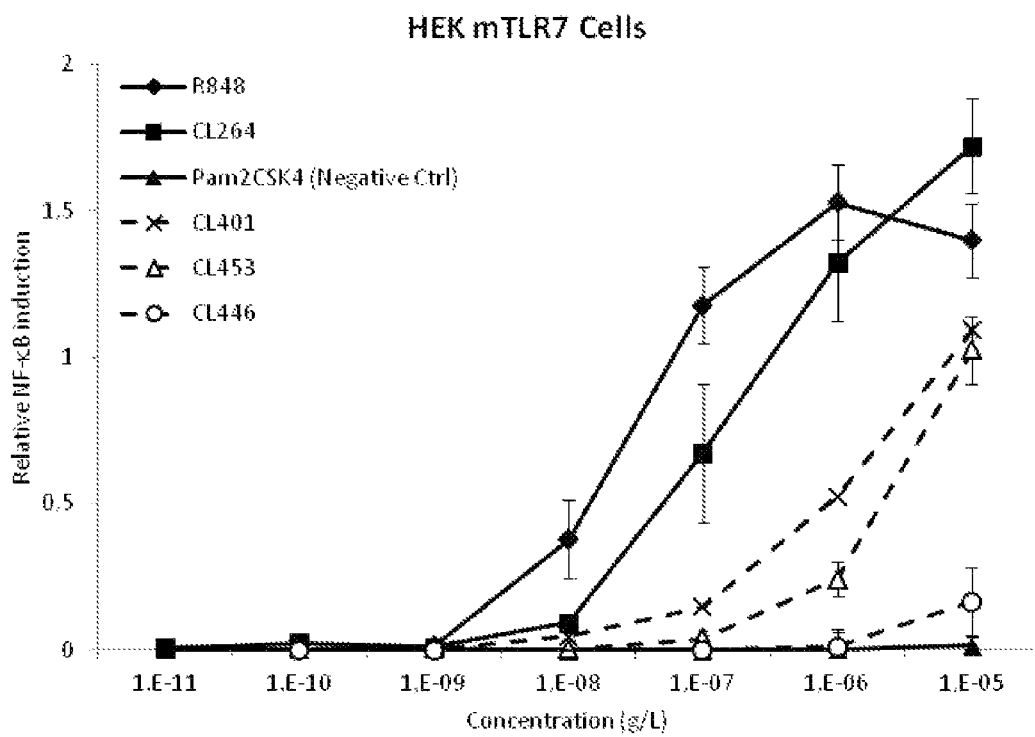
FIG. 2A is a graphical representation of the activity of di- or tri-acylated molecules of the invention towards murine TLR7.
Figure 2B:
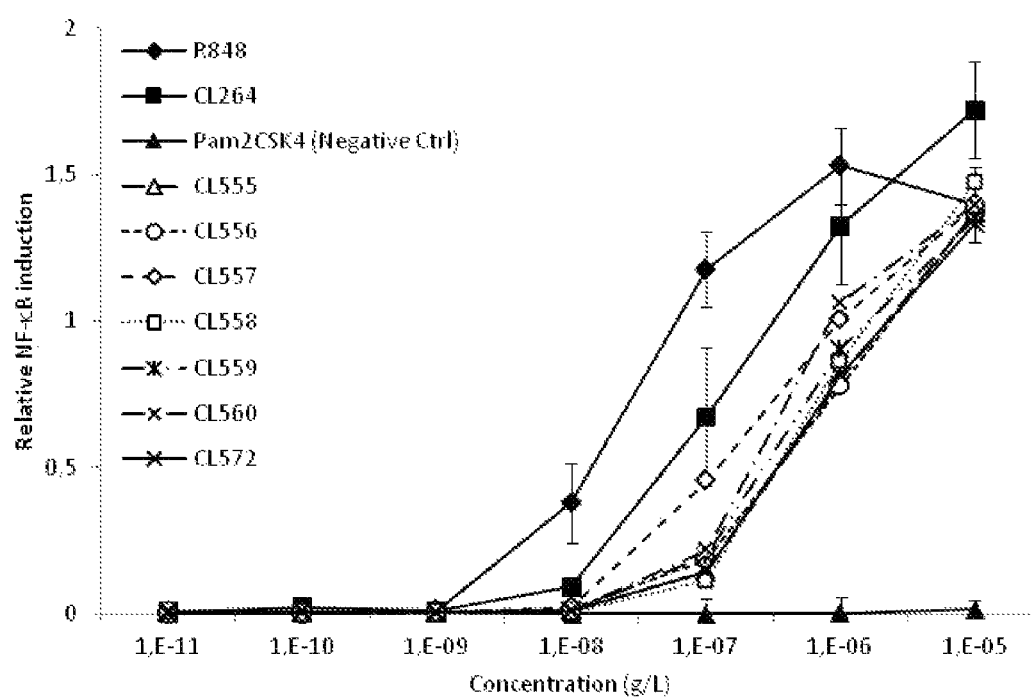
FIG. 2B is a graphical representation of the activity of mono-acylated molecules of the invention towards murine TLR7.

FIGS. 1A, 1B, 2A and 2B demonstrate the ability of conjugated molecules of the invention (CL401, CL453, CL446, CL555, CL556, CL557, CL558, CL559, CL560 and CL572) to activate TLR7 receptors. Activity was assessed using HEK Blue™ human TLR7 reporter cells. FIG. 1A shows activity of di- or tri-acylated molecules of the invention and FIG. 1B shows activity of mono-acylated molecules of the invention towards human TLR7. Activity was also assessed using HEK Blue™ murine TLR7 reporter cells. FIG. 2A shows activity of di- or tri-acylated molecules of the invention and FIG. 2B shows activity of mono-acylated molecules of the invention towards murine TLR7. Positive controls include TLR7 agonists R848 (InvivoGen) and CL264 (InvivoGen). Negative control used is TLR2 agonist $Pam_2CSK_4$ (InvivoGen).

Figure 3A:
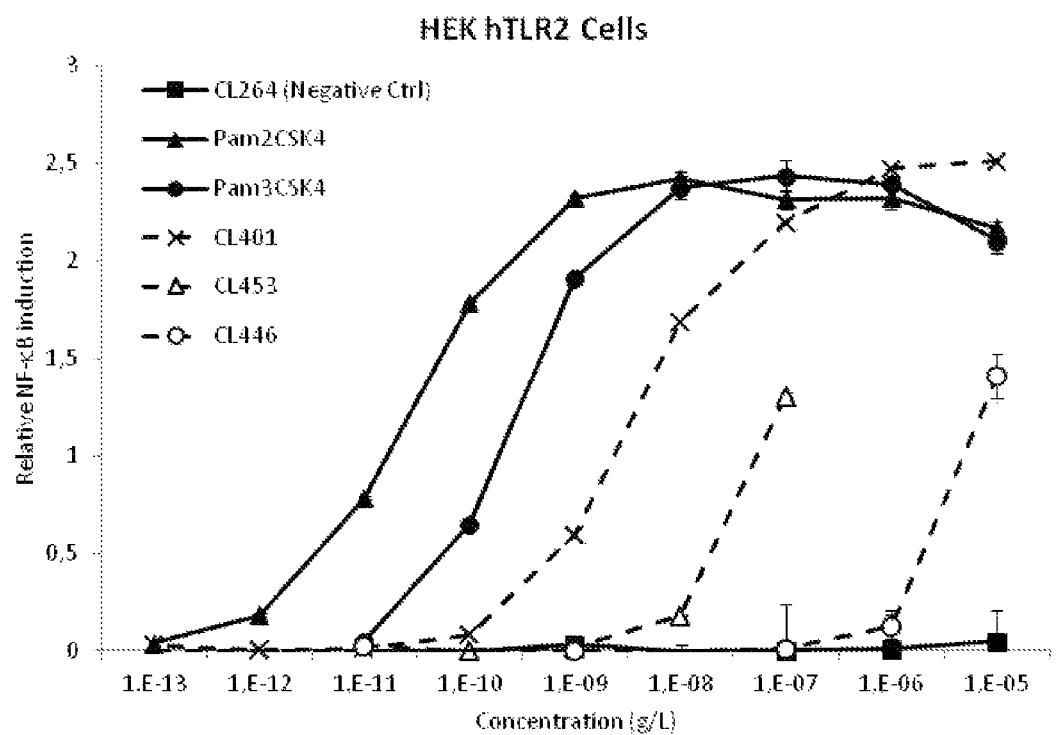
FIG. 3A is a graphical representation of the activity of di- or tri-acylated molecules of the invention towards human TLR2.
Figure 3B:
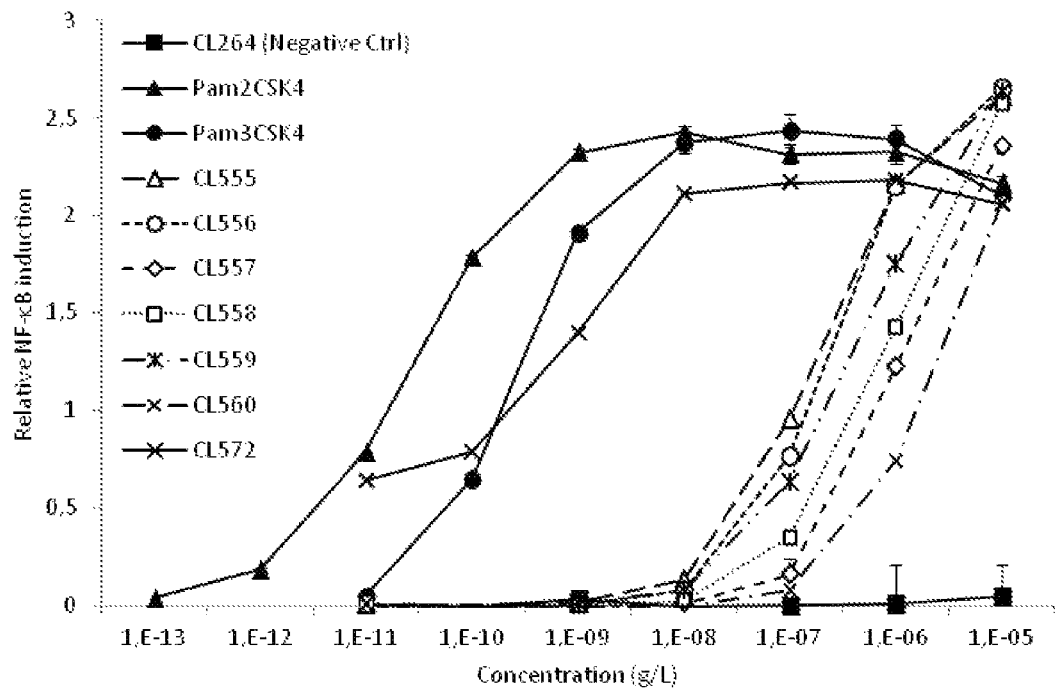
FIG. 3B is a graphical representation of the activity of mono-acylated molecules of the invention towards human TLR2.

FIGS. 3A and 3B demonstrate the ability of conjugated molecules of the invention (CL401, CL453, CL446, CL555, CL556, CL557, CL558, CL559, CL560 and CL572) to activate TLR2 receptor. Activity was assessed using HEK Blue™ human TLR2 reporter cells. FIG. 3A shows activity of di- or tri-acylated molecules of the invention and FIG. 3B shows activity of mono-acylated molecules of the invention towards human TLR2. Positive controls include TLR2 agonists $Pam_2CSK_4$ and $Pam_3CSK_4$ (InvivoGen). Negative control used is TLR7 agonist CL264.

Figure 4:
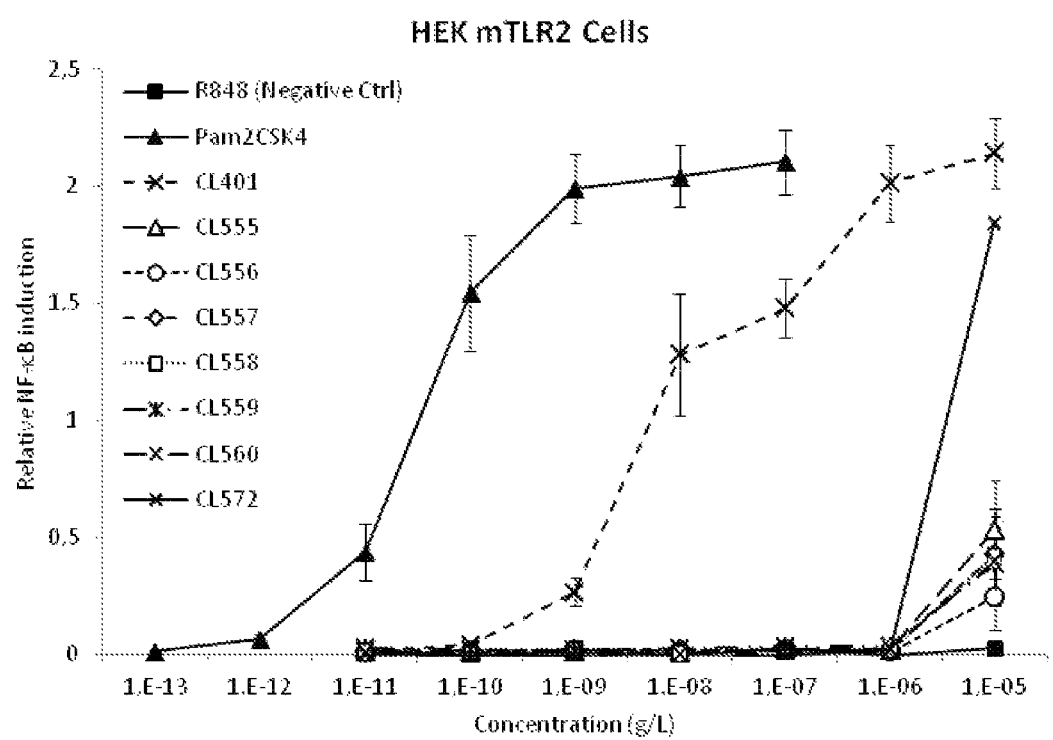
FIG. 4 is a graphical representation of the ability of conjugated molecules of the invention (CL401, CL555, CL556, CL557, CL558, CL559, CL560 and CL572) to activate TLR2 receptor.

FIG. 4 demonstrates the ability of conjugated molecules of the invention (CL401, CL555, CL556, CL557, CL558, CL559, CL560 and CL572) to activate TLR2 receptor. Activity was assessed using HEK Blue™ murine TLR2 reporter cells. The graph shows activity of best di-acylated molecule and activity of mono-acylated molecules of the invention towards murine TLR2. The positive control used is TLR2 agonist $Pam_2CSK_4$ and the negative control used is TLR7/8 agonist R848.

Figure 5A:
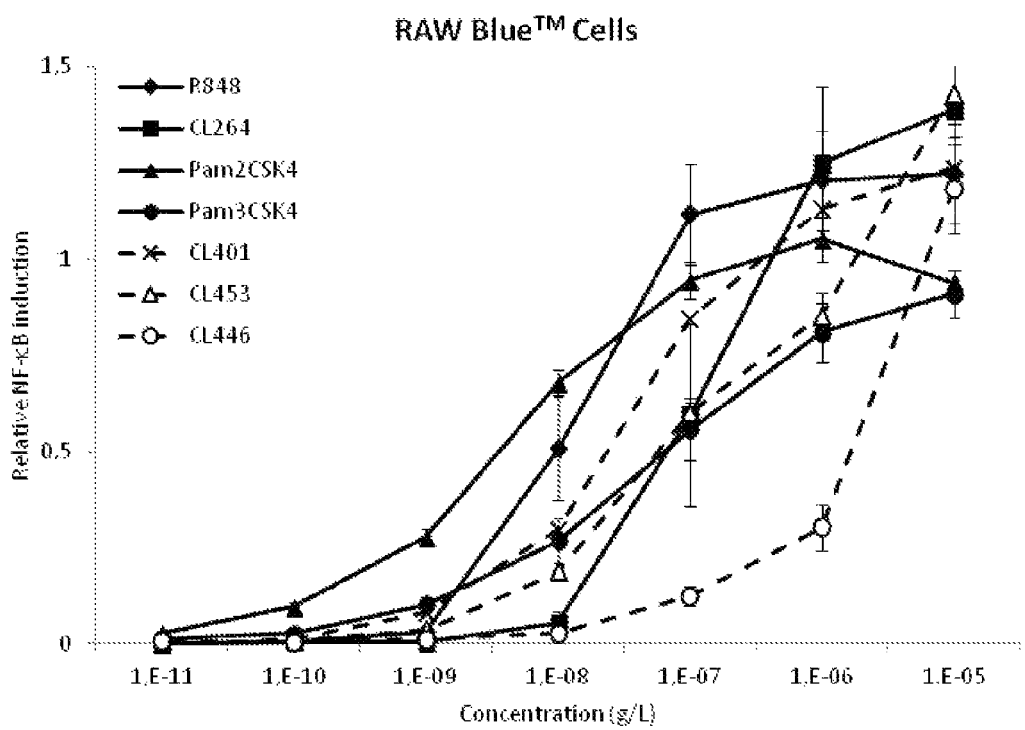
FIG. 5A is a graphical representation of the activity of di- or tri-acylated molecules of the invention towards murine TLR7.
Figure 5B:
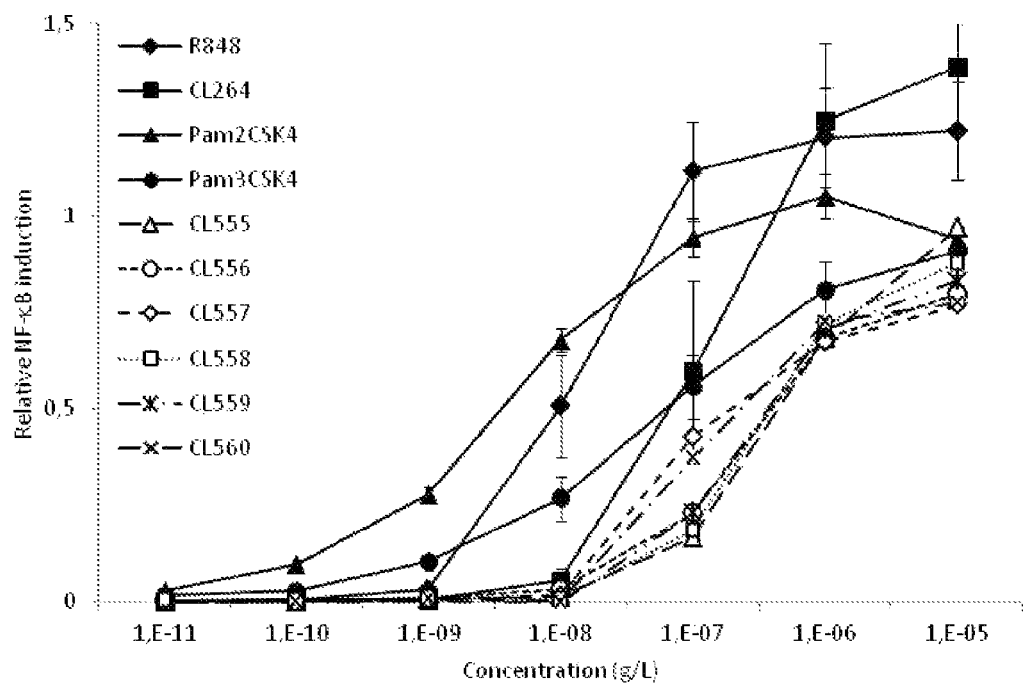
FIG. 5B is a graphical representation of the activity of mono-acylated molecules of the invention towards murine TLR7.

FIGS. 5A and 5B demonstrate the ability of conjugated molecules of the invention (CL401, CL453, CL446, CL555, CL556, CL557, CL558, CL559 and CL560) to activate NF-κB in immune cells, using the murine monocytic macrophage cell line, RAW 264.7. The graphs show the induction of NF-κB in RAW-Blue™ cells. FIG. 5A shows activity of di- or tri-acylated molecules of the invention and FIG. 5B shows activity of mono-acylated molecules of the invention towards murine TLR7. Positive controls include TLR2 agonists Pam$_2$CSK$_4$ and Pam$_3$CSK$_4$ and TLR7 agonists CL264 and R848.

Figure 6A:
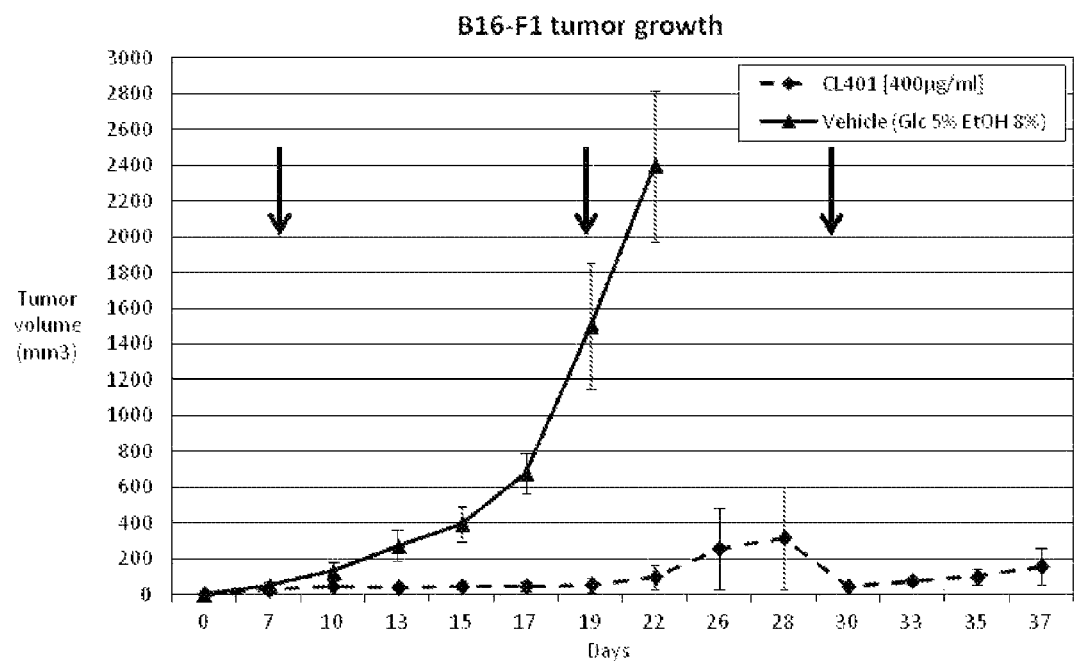
FIG. 6A is a graphical representation depicting the tumor volume over time of CL401-treated mice compared to control vehicle treated.
Figure 6B:
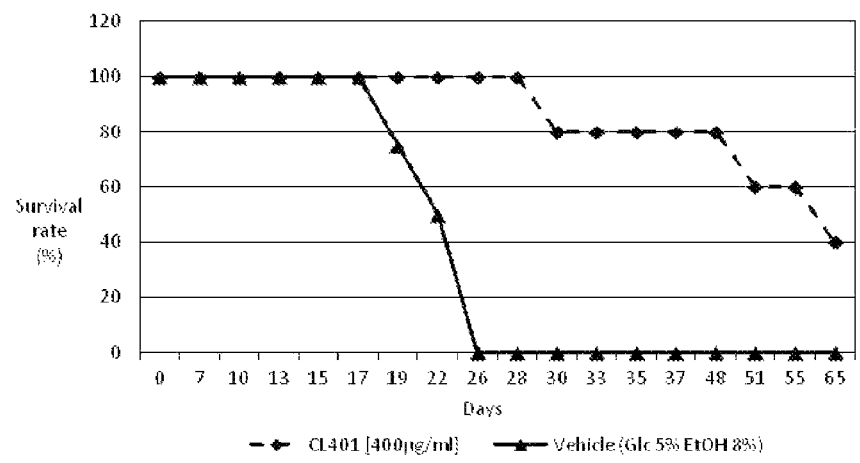
FIG. 6B is a graphical representation depicting the survival curve of the CL401-treated mice compared to control vehicle treated.

FIGS. 6A and 6B demonstrate the in vivo results in B16-F1 allograft tumor mouse model treated with CL401 conjugated small molecule of the invention. The graph in FIG. 6A shows the tumor volume over time of CL401-treated mice compared to control vehicle treated. Arrows indicate timing of intra-tumoral injections and the error bars indicate standard error of the 7 mice. The graph in FIG. 6B shows the survival curve of the CL401-treated mice compared to control vehicle treated.

EXAMPLES

Methods of Synthesis

The present invention is next described by means of the following examples. However, the use of these and other examples anywhere in the specification is illustrative only, and in no way limits the scope and meaning of the invention or of any exemplified form. Likewise, the invention is not limited to any particular preferred embodiments described herein. Indeed, many modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Abbreviations

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification:

AcOH for acetic acid; Boc for tert-butyloxy carbonyl; Boc$_2$O for di-tert-butyl dicarbonate; CDCl$_3$-d$_1$ for deuterated chloroform; Cs$_2$CO$_3$ for cesium carbonate; ° C. for degree Celsius; DCM for dichloromethane; δ for chemical shift, DIEA for N,N-Diisopropylethylamine; DMAP for N,N-dimethylamino pyridine; DMF for N,N-dimethyl formamide; DMSO-d$_6$ for deuterated dimethylsulfoxide; EDCI for 1-(3-diethylaminopropyl)-3-ethylcarbodiimide hydrochloride; EtOH for ethanol; Et$_2$O for diethyl ether; EtOAc for ethyl acetate; ES for electrospray ionization; eq. for equivalent; g grams; $^1$H for hydrogen-1; HATU for O-(7-Azabenzotriazol-1-yl)-N,N,N',N'-tetramethyluronium hexafluorophosphate; HCl for hydrochloric acid; HPLC for high performance liquid chromatography; h for hours; mg for milligrams; KHSO4 for potassium hydrogenosulfate; mCPBA for meta-Chloroperoxybenzoic acid; MgSO$_4$ for magnesium sulfate; MeOH for methanol; mL for milliliters; mmol for millimoles; MHz for megahertz; min for minutes; μL for microliters; MS for mass spectrometry; N for normality of a solution; Na$_2$CO$_3$ for sodium carbonate; Na$_2$SO$_4$ for sodium sulfate; Na$_2$S$_2$O$_3$ for sodium thiosulfate; NaHCO$_3$ for sodium hydrogenocarbonate; NH$_4$Cl for ammonium chloride; NH$_4$OH for ammonium hydroxide; NMR for nuclear magnetic resonance; P$_2$O$_5$ for phosphorus pentoxide; Pd/C for Palladium on activated charcoal; ppm for parts per million; rt for room temperature; TFA for trifluoroacetic acid; THF for tetrahydrofuran; TLC for thin layer chromatography; and Z for benzyloxy carbonyl;

General Information

Characterization:

1. Proton NMR Spectra: Unless otherwise indicated, all $^1$H NMR spectra were run on a Bruker series 300 MHz instrument. Where so characterized, all observed protons are reported as parts-per-million (ppm) downfield from tetramethylsilane (TMS) or other internal reference in the appropriate solvent indicated. NMR spectra were recorded on a Brucker 300 spectrometer. For $^1$H (300 MHz) spectra δ values were referenced to CDCl$_3$-d$_1$ (7.26 ppm) or DMSO-d$_6$ (2.50 ppm). The peak patterns are indicated as follows: s: singlet, sl: large singlet, d: doublet, t: triplet, q: quartet, m: multiplet.

2. Mass Spectra (MS): Analyses were run on an Agilent Model 6130 quadrupole MS. Unless otherwise indicated, all mass spectral data for starting materials, intermediates and/or exemplary compounds are reported as mass/charge (m/z), having an (M+H)$^+$ molecular ion. The molecular ion reported was obtained by electrospray detection method (commonly referred to as an ESI MS). Compounds having an isotopic atom, such as bromine and the like, are generally reported according to the detected isotopic pattern, as appreciated by those skilled in the art.

3. Naming Convention The compounds disclosed and described herein have been named using the naming convention provided with Chem-Draw Ultra 11.0 software, available in Chem. Office. Chem.-Draw utilizes the ISIS Draw software compound naming convention, as appreciated by those skilled in the art.

Reagents and solvents: All commercially available reagents and protected amino acids were purchased and used without further purification. All the solvents used for reactions were distilled over appropriate drying reagents prior to use. Commercially available ACS grade solvents (>99.0% purity) were used for column chromatography without any further purification.

Reactions and Purifications: For all of the following examples, standard work-up and purification methods known to those skilled in the art can be utilized. Unless otherwise indicated, all temperatures are expressed in ° C. (degrees Centigrade). All reactions conducted at room temperature unless otherwise noted. All reactions and fractions from column chromatography were monitored by thin layer chromatography (TLC) using glass plates with a UV fluorescent indicator (normal SiO$_2$, Merck 60 F254). One or more of the following methods were used for visualization: UV absorption by fluorescence quenching; (Ninhydrin/Ethanol or H$_2$SO$_4$/Ethanol) solution. Flash chromatography was performed using Merck type 60, 230-400 mesh silica gel.

Example 1

Molecule CL401

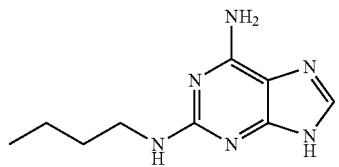

Intermediate 1

6-amino-2-butylamino-9H-purine: 2-Chloroadenine (10.0 g, 59 mmol), butylamine (43 mL, 589 mmol) and water (40 mL) were placed in an autoclave (250 mL), and the content of the autoclave was allowed to react at 180° C. for 18 h. The reaction solution was concentrated under reduced pressure, and water was poured into the residue to precipitate a solid. The precipitated solid was sequentially washed with water, EtOH and acetone. Thus, 10.39 g of the title compound was obtained as a yellowish orange powdery solid (yield: 86%). Intermediate 1 was characterized by the following spectroscopic data: $^1$H NMR (DMSO-$d_6$, 300 MHz): 11.92 (br. S, 1H), 7.63 (s, 1H), 6.51 (br. s, 2H), 6.04 (s, 1H), 3.19 (q, 2H), 1.51 (m, 2H), 1.33 (m, 2H), 0.92 (t, 3H).

Intermediate 2

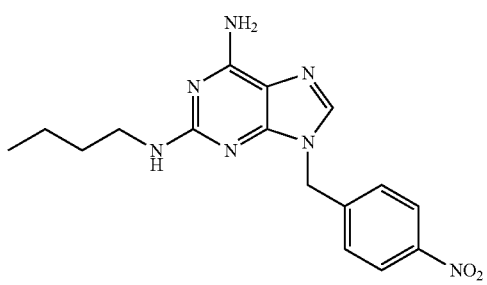

N2-butyl-9-(4-nitrobenzyl)-9H-purine-2,6-diamine: 6-amino-2-butylamino-9H-purine, intermediate 1 (9.93 g, 48.2 mmol) and $Cs_2CO_3$ (15.69 g, 48.2 mmol) were suspended in DMF (200 mL). 4-nitrobenzyl bromide (12.48 mg, 57.8 mmol) was added thereto and the mixture was stirred at room temperature for 18 h. After condensing the suspension in vacuo, to the residue was added brine and the mixture was extracted with ethyl acetate. The organic layer was washed the mixture was with brine, dried on $MgSO_4$, filtered and the solvent was evaporated in vacuo. The residue was purified on column of silica gel (5% MeOH/DCM) to give the subject compound (11.51 g, yield 70%). Intermediate 2 was characterized by the following spectroscopic data: $^1$H NMR (DMSO-$d_6$, 300 MHz) δ (ppm) 8.19 (d, 2H), 7.83 (s, 1H), 7.49 (d, 2H), 6.69 (sl, 2H), 6.25 (t, 1H), 5.34 (s, 2H), 3.17 (m, 2H), 1.41 (m, 2H), 1.25 (q, 2H), 0.83 (t, 3H).

Intermediate 3

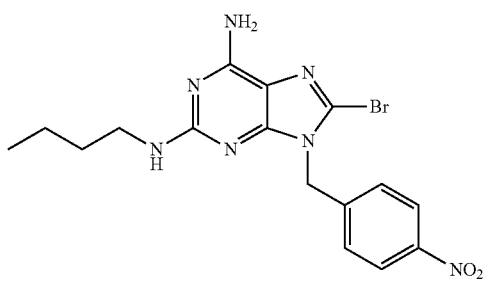

8-bromo-N2-butyl-9-(4-nitrobenzyl)-9H-purine-2,6-diamine: To a solution of intermediate 2 (11.50 g, 33.7 mmol) in 200 mL of $CHCl_3$ was added bromine (12.93 mL, 80.92 mmol). The solution was stirred at room temperature for 18 h. Then, aqueous $Na_2S_2O_3$ was added to the reaction mixture. The precipitate obtained was filtered off and washed with water and DCM. The solid was purified on column of silica gel (3% MeOH/DCM) to give the subject compound (14.17 g, yield 100%). Intermediate 3 was characterized by the following spectroscopic data: $^1$H NMR (DMSO-$d_6$, 300 MHz) δ (ppm) 8.21 (d, 2H), 7.51 (d, 2H), 5.39 (s, 2H), 3.15 (m, 2H), 1.44 (m, 2H), 1.27 (q, 2H), 0.82 (t, 3H).

Intermediate 4

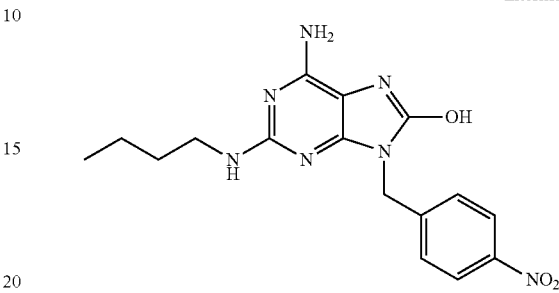

6-amino-2-(butylamino)-9-(4-nitrobenzyl)-9H-purin-8-ol: To a solution of intermediate 3 (14.17 g, 33.72 mmol) in 150 mL of dioxane was added 100 mL of HCl 37% solution. The mixture was refluxed on heating under stirring for 18 h. The mixture was concentrated in vacuo and the pH was adjusted to 5 with 2N aqueous NaOH to precipitate a solid. The solid was filtered, washed with water and dried in vacuo in presence of $P_2O_5$ to give the subject compound (11.05 g, yield 90%). Intermediate 4 was characterized by the following spectroscopic data: $^1$H NMR (DMSO-$d_6$, 300 MHz) δ (ppm) 10.35 (sl, 1H), 8.19 (d, 2H), 7.53 (d, 2H), 7.23 (sl, 2H), 4.98 (s, 2H), 3.19 (m, 2H), 1.41 (m, 2H), 1.24 (q, 2H), 0.80 (t, 3H).

Intermediate 5

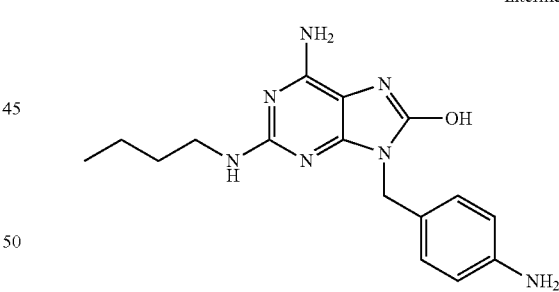

6-amino-9-(4-aminobenzyl)-2-(butylamino)-9H-purin-8-ol: To a solution of intermediate 4 (11.05 g, 30.9 mmol) in a mixture of THF/MeOH (1/1) (200 mL) was added Pd/C (1.79 g, 1.6 mmol), the reaction mixture was stirred at rt under hydrogen atmosphere for 18 h. Then the mixture was filtered off over Celite, washed with MeOH. The filtrate was concentrated in vacuo and the residue was purified on column of silica gel with DCM/MeOH (0-7%) as eluent to give the subject compound (7.52 g, yield 74%). Intermediate 5 was characterized by the following spectroscopic data: $^1$H NMR (DMSO-$d_6$, 300 MHz) δ (ppm) 10.02 (sl, 1H), 7.07 (d, 2H), 6.87 (sl, 2H), 6.77 (sl, 2H), 6.58 (d, 2H), 4.65 (s, 2H), 3.23 (m, 2H), 1.49 (m, 2H), 1.33 (q, 2H), 0.92 (t, 3H).

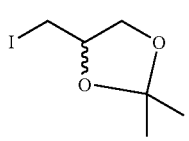

Intermediate 6

4-(iodomethyl)-2,2-dimethyl-1,3-dioxolane: To a solution of (2,2-dimethyl-1,3-dioxolan-4-yl)methanol (10 g, 75.67 mmol) in dry toluene (200 mL) were added triphenylphosphine (23.82 g, 90.81 mmol), imidazole (15.45 g, 227 mmol), and iodine (24.97 g, 98.36 mmol). The mixture was stirred at 90° C. for 3 h. The solvent was then removed in vacuo and the residue was dissolved in DCM (200 mL) and washed with saturated $Na_2S_2O_3$ solution water and brine. The organic layer was dried over $MgSO_4$, filtered and concentrated in vacuo. The crude compound was purified on column of silica gel (DCM) to give the subject compound (15.79 g, yield 86%). Intermediate 6 was characterized by the following spectroscopic data: $^1$H NMR ($CDCl_3$-$d_1$, 300 MHz) δ (ppm) 4.33 (m, 1H), 4.19 (m, 1H), 3.82 (m, 1H), 3.32 (m, 1H), 3.27 (m, 1H), 1.49 (s, 3H), 1.38 (s, 3H).

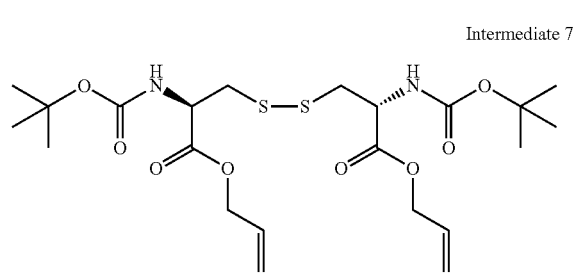 [SMILES: C=CCOC(=O)[C@H](CSSC[C@H](NC(=O)OC(C)(C)C)C(=O)OCC=C)NC(=O)OC(C)(C)C]

Intermediate 7

(2R,2'R)-diallyl 3,3'-disulfanediylbis(2-(tert-butoxycarbonylamino)propanoate): To a solution of L-cystine (13 g, 54.1 mmol) in water (200 mL) was added triethylamine (22.81 mL, 162.3 mmol). The mixture was stirred at rt for 5 min then was added dropwise a solution of $Boc_2O$ (35.42 g, 162.3 mmol) in dioxane. The mixture was stirred at rt overnight. The solvent was then removed in vacuo and the residue was dissolved in EtOAc (200 mL) and washed with 0.1 N HCl solution, water and brine. The organic layer was dried over $MgSO_4$, filtered and concentrated in vacuo. The crude compound was dried and dissolved in dry DMF. To this solution was $Cs_2CO_3$ (19.12 g, 58.7 mmol) and allyl bromide (9.92 mL, 117.4). The mixture was stirred at rt overnight. The solvent was removed in vacuo and the residue was dissolved in EtOAc (200 mL), washed with 0.1 N HCl solution, water and brine. The organic layer was dried over $MgSO_4$, filtered and concentrated in vacuo. The crude compound was purified on column of silica gel (2% MeOH/DCM) to give the subject compound (22.53 g, yield 80%). Intermediate 7 was characterized by the following spectroscopic data: $^1$H NMR (DMSO-$d_6$, 300 MHz) δ (ppm) 7.43 (d, 2H), 5.89 (m, 2H), 5.29 (m, 4H), 4.59 (d, 4H), 4.02 (m, 2H), 3.07 (m, 4H), 1.38 (s, 18H).

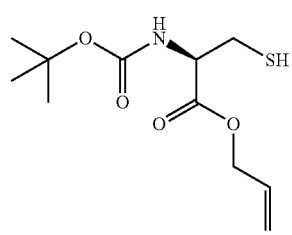

Intermediate 8

(R)-allyl 2-(tert-butoxycarbonylamino)-3-mercaptopropanoate: The intermediate 7 (20.00 g, 38.4 mmol) was suspended in a mixture of ethyl acetate/5% w/v aqueous $NaHCO_3$ (1:1, 400 mL) within a tuba-sealed 500 mL round bottomed flask. The flask was then purged with nitrogen to displace any air within the vessel. This solution was vigorously stirred and tributylphosphine (20.85 ml, 84.5 mmol) was added by positive displacement. The reaction mixture was then agitated for 2 h. At the end of this time the reaction was quenched by the careful addition of 1 M aqueous $KHSO_4$ (60 mL). The reaction mixture was then transferred to a separating funnel and the crude product was extracted into ethyl acetate (3×200 mL). The organic fractions were then combined and concentrated in vacuo to afford viscous brown oil. The crude oil was purified on column of silica gel (15% EtOAc/Cyclohexane) to give the subject compound (19.00 g, yield 94%). Intermediate 8 was characterized by the following spectroscopic data: $^1$H NMR ($CDCl_3$-$d_1$, 300 MHz) δ (ppm) 5.94 (m, 1H), 5.34 (m, 3H), 4.67 (m, 3H), 4.26 (m, 1H), 3.01 (m, 2H), 1.46 (s, 9H).

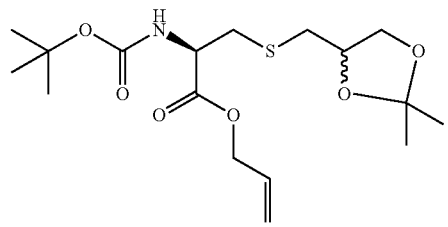

Intermediate 9

(R)-allyl 2-(tert-butoxycarbonylamino)-3-(2,2-dimethyl-1,3-dioxolan-4-yl)methylthio)propanoate: To a solution of intermediate 8 (7.34 g, 28.1 mmol) in dry DMF (100 mL) were added triethylamine (15.39 mL, 109.5 mmol) and intermediate 1 (8.83 g, 36.51 mmol). The mixture was stirred at 80° C. overnight. The solvent was then removed in vacuo and the residue was dissolved in DCM (150 mL) and washed with 0.1 N HCl solution water and brine. The organic layer was dried over $MgSO_4$, filtered and concentrated in vacuo. The crude compound was purified on column of silica gel (2% MeOH/DCM) to give the subject compound (7.18 g, yield 68%). Intermediate 9 was characterized by the following spectroscopic data: $^1$H NMR ($CDCl_3$-$d_1$, 300 MHz) δ (ppm) 5.93 (m, 1H), 5.39 (m, 1H), 5.30 (m, 2H), 4.67 (d, 2H), 4.60 (m, 1H), 4.24 (m, 1H), 4.11 (m, 1H), 3.70 (m, 1H), 3.06 (m, 2H), 2.70 (m, 2H), 1.46 (s, 9H), 1.44 (s, 3H), 1.37 (s, 3H).

Intermediate 10

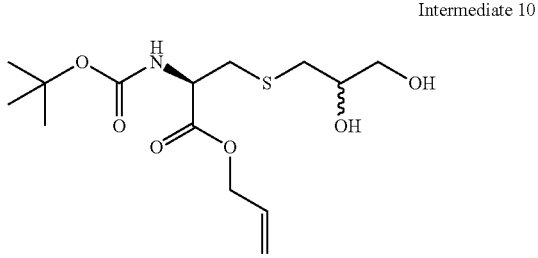 [SMILES: C=CCOC(=O)[C@H](CSCC(O)CO)NC(=O)OC(C)(C)C]

(R)-allyl 2-(tert-butoxycarbonylamino)-3-(2,3-dihydroxypropylthio)propanoate: The intermediate 9 (7.18 g, 19.1 mmol) was dissolved in a solution of AcOH 70% (220 mL). The mixture was stirred at RT overnight. The solvent was then removed in vacuo and the residue was directly applied to a column of silica gel (4% MeOH/DCM) to give the subject compound (5.01 g, yield 78%). Intermediate 10 was characterized by the following spectroscopic data: $^1$H NMR (CDCl$_3$-d$_1$, 300 MHz) δ (ppm) 5.93 (m, 1H), 5.40 (m, 1H), 5.34 (m, 2H), 4.67 (d, 2H), 4.62 (m, 1H), 3.79 (m, 3H), 3.61 (m, 1H), 3.05-2.65 (m, 5H), 1.47 (s, 9H).

Intermediate 11

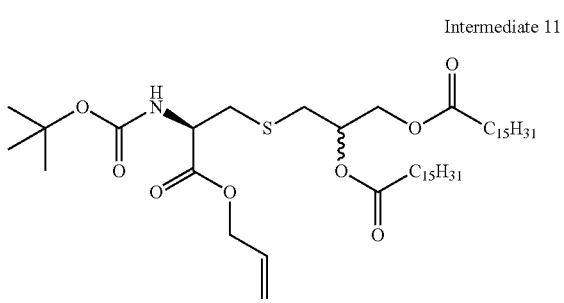

(R)-3-(3-(allyloxy)-2-(tert-butoxycarbonylamino)-3-oxopropylthio)propane-1,2-diyl dipalmitate: A solution of intermediate 10 (4.22 g, 12.6 mmol) in dry DCM (150 mL) was cooled in an ice bath. EDCI (6.27 g, 32.7 mmol), DMAP (3.99 g, 32.7 mmol) and palmitic acid (8.38 g, 32.7 mmol) were added to the solution. The mixture was stirred for 10 min then warmed up to rt and stirred overnight. The reaction mixture was diluted with DCM, washed with 0.1 N HCl solution water and brine. The organic layer was dried over MgSO$_4$, filtered and concentrated in vacuo. The crude compound was purified on column of silica gel (DCM) to give the subject compound (9.55 g, yield 93%). Intermediate 11 was characterized by the following spectroscopic data: $^1$H NMR (CDCl$_3$-d$_1$, 300 MHz) δ (ppm) 5.93 (m, 1H), 5.32 (m, 3H), 5.15 (m, 1H), 4.67 (d, 2H), 4.57 (m, 1H), 4.36-4.13 (m, 2H), 3.04 (m, 2H), 2.75 (m, 2H), 2.32 (m, 4H), 1.67 (m, 4H), 1.46 (s, 9H), 1.27 (s, 48H), 0.89 (t, 6H).

Intermediate 12

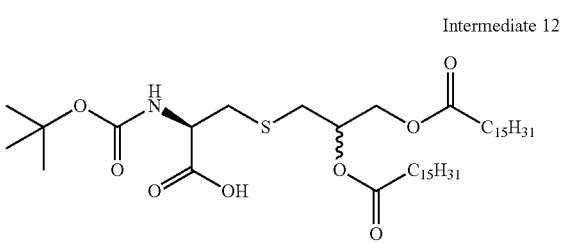

(R)-3-(2,3-bis(palmitoyloxy)propylthio)-2-(tert-butoxycarbonylamino)propanoic acid: To a solution of intermediate 11 (7.51 g, 9.2 mmol) in dry THF (120 mL) were added Tetrakis(triphenylphosphine)palladium(0) (2.13 g, 1.8 mmol) and N-methylaniline (2.97 mL, 27.74 mmol). The mixture was stirred at RT for 1H00. The solvent was then removed in vacuo and the residue was dissolved in EtOAc (150 mL) and washed with 0.1 N HCl solution, water and brine. The organic layer was dried over MgSO$_4$, filtered and concentrated in vacuo. The crude compound was purified on column of silica gel (DCM) to give the subject compound (6.94 g, yield 97%). Intermediate 12 was characterized by the following spectroscopic data: $^1$H NMR (CDCl$_3$-d$_1$, 300 MHz) δ (ppm) 5.48 (m, 1H), 5.16 (m, 1H), 4.50 (m, 1H), 4.38-4.13 (m, 2H), 3.04 (m, 2H), 2.77 (m, 2H), 2.33 (m, 4H), 1.61 (m, 4H), 1.46 (s, 9H), 1.27 (s, 48H), 0.89 (t, 6H).

Intermediate 13

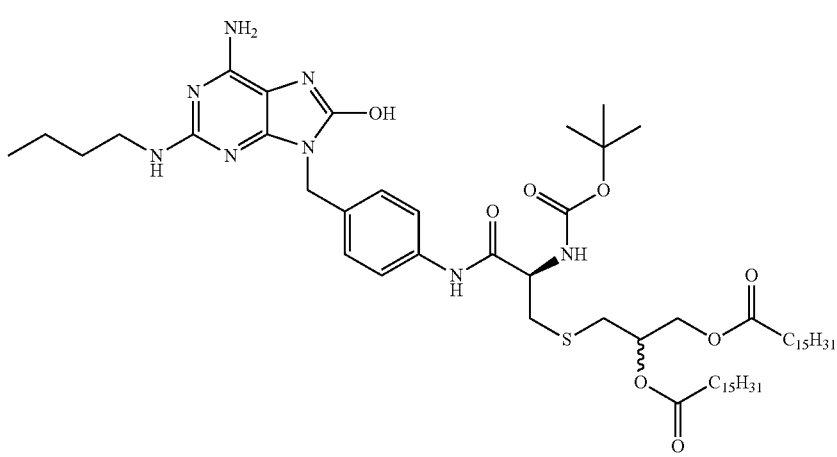

(R)-3-(3-(4-((6-amino-2-(butylamino)-8-hydroxy-9H-purin-9-yl)methyl)phenylamino)-2-(tert-butoxycarbonylamino)-3-oxopropylthio)propane-1,2-diyl dipalmitate: To a solution of intermediate 5 (512 mg, 1.5 mmol) in dry DMF (30 mL) was added intermediate 12 (1.20 g, 1.5 mmol), HATU (654 mg, 1.7 mmol), and DIEA (5.77 µL, 3.1 mmol). The mixture was stirred at rt for 4 h. The solvent was then removed in vacuo and the residue was dissolved in DCM (50 mL) and washed with 0.1 N HCl solution, water and brine. The organic layer was dried over MgSO$_4$, filtered and concentrated in vacuo. The crude compound was purified on column of silica gel (5% MeOH/DCM) to give the subject compound (765 mg, yield 45%). Intermediate 8 was characterized by the following spectroscopic data: $^1$H NMR (DMSO-d$_6$, 300 MHz) δ (ppm) 10.06 (sl, 1H), 7.52 (d, 2H), 7.25 (d, 2H), 7.16 (m, 1H), 6.16 (m, 1H), 5.96 (sl, 2H), 5.09 (m, 1H), 4.71 (s, 2H), 4.30-4.09 (m, 4H), 3.17 (m, 2H), 2.87-2.71 (m, 4H), 2.27 (m, 4H), 1.50 (m, 4H), 1.48 (s, 9H), 1.27 (m, 52H), 0.85 (m, 9H).

Example 2

Molecule CL549

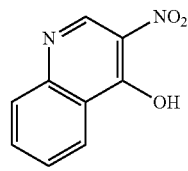

Intermediate 15

3-nitroquinolin-4-ol: 4-Hydroxyquinoline (20.0 g, 138 mmol) was added to propionic acid (150 mL) and the solution was heated to about 125° C. Nitric acid (6.85 mL, 165 mmol) was added dropwise with stirring. When the addition was complete, the mixture was stirred at about 125° C. overnight. Then the mixture was cooled to room tem-

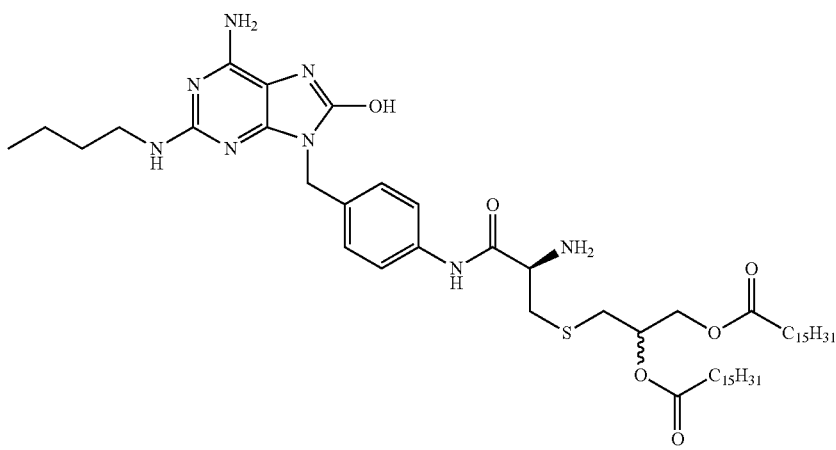

Compound 14

CL401

(R)-3-(2-amino-3-(4-((6-amino-2-(butylamino)-8-hydroxy-9H-purin-9-yl)methyl)phenyl amino)-3-oxopropylthio)propane-1,2-diyl dipalmitate: To a solution of intermediate 13 (765 mg, 0.7 mmol) in dioxane (10 mL) was added 4N HCl solution in dioxane (20 mL). The mixture was stirred at RT overnight. Then the solvent were removed in vacuo, the residue was triturated with Et$_2$O, filtrated, and dried. The crude compound was purified on column of silica gel (5% MeOH/DCM) to give the subject compound (677 mg, yield 97%). Compound 14 was characterized by the following spectroscopic data: $^1$H NMR (DMSO-d$_6$, 300 MHz) δ (ppm) 10.56 (sl, 1H), 10.10 (m, 1H), 8.38 (sl, 2H), 7.54 (d, 2H), 7.32 (d, 2H), 6.16 (m, 1H), 5.96 (sl, 2H), 5.11 (m, 1H), 4.79 (s, 2H), 4.11-4.05 (m, 3H), 3.24 (m, 2H), 3.16-2.99 (m, 4H), 2.23 (m, 4H), 1.48 (m, 4H), 1.28 (m, 52H), 0.84 (m, 9H). MS (+)-ES [M+H]$^+$ 981.6 perature and was poured on ice. The precipitated solid was filtered, washed sequentially with water, EtOH and Et$_2$O, and dried to afford 3-nitro-4-hydroxyquinoline (18.7 g, yield 71%) as a light yellow powder.

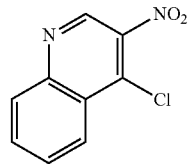

Compound 16

4-chloro-3-nitroquinoline: The Intermediate 3-nitro-4-hydroxyquinoline 15 (18.7 g, 98.4 mmol) was suspended in dichloromethane (150 mL). Thionyl chloride (17.2 mL, 236 mmol) and DMF (9.2 mL, 118 mmol) were added. The reaction mixture was then heated at reflux overnight. The reaction mixture was then poured in ice. The layers were separated and the organic layer was washed with NaHCO₃ solution, water and brine. The organic layer was dried over Na₂SO₄, filtered and concentrated in vacuo. The residue (20.52 g, yield 93%) was used for the next step without any further purification.

Intermediate 17

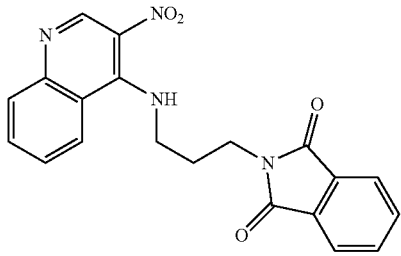

2-(3-(3-nitroquinolin-4-ylamino)propyl)isoindoline-1,3-dione: To a solution of intermediate 16 (2.00 g, 10 mmol) in dry DCM (25 mL) was added a solution of 3-phthalimido propylamine (2.44 g, 12 mmol), and triethylamine (6.69 mL, 47.9 mmol) in dichloromethane (25 mL) at 0° C. The resulting solution was heated at reflux overnight. Then the reaction mixture was cooled to RT and the solvent was removed at reduced pressure to afford a yellow solid product. The product was slurred in water, filtered, washed with water, and dried partially. The partially dried product was then slurred in ethanol (75 mL), filtered, washed successively with a small amount of ethanol and a small amount of diethyl ether, and dried at reduced pressure to afford the subject compound (3.55 g, yield 98%). Intermediate 17 was characterized by the following spectroscopic data: ¹H NMR (DMSO-d₆, 300 MHz) δ (ppm) 8.99 (s, 1H), 8.85 (t, 1H), 8.45 (d, 1H), 7.92 (d, 1H), 7.77 (m, 5H), 7.55 (m, 1H), 3.65 (m, 4H), 2.09 (t, 2H).

Intermediate 18

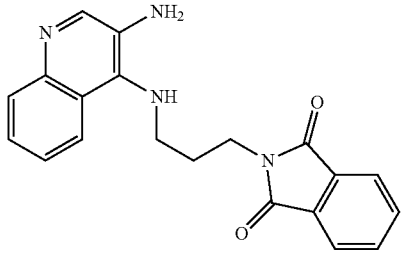

2-(3-(3-aminoquinolin-4-ylamino)propyl)isoindoline-1,3-dione: To a solution of intermediate 17 (3.55 g, 9.4 mmol) in a mixture of THF/MeOH (1/1) (100 mL) was added palladium on activated carbon 10% (0.05 eq). The reaction mixture was stirred under hydrogen (1 atm) overnight. The palladium was filtered off the filtrate was concentrated in vacuo. The crude mixture was purified on column of silica gel (5% MeOH/DCM) to give the subject compound (2.00 g, yield 61%). Intermediate 18 was characterized by the following spectroscopic data: ¹H NMR (DMSO-d₆, 300 MHz) δ (ppm) 8.42 (s, 1H), 8.05 (m, 1H), 7.85 (m, 4H), 7.73 (m, 1H), 7.32 (m, 2H), 5.02 (sl, 2H), 3.66 (m, 4H), 1.86 (m, 2H).

Intermediate 19

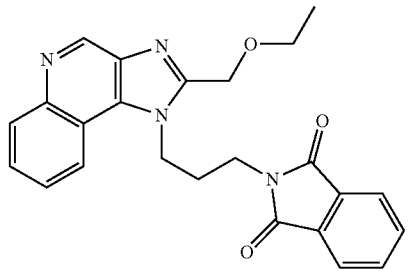

2-(3-(4-amino-2-(ethoxymethyl)-1H-imidazo[4,5-c]quinolin-1-yl)propyl)isoindoline-1,3-dione: The intermediate 18 (550 mg, 1.60 mole) was dissolved in ethoxyacetic acid (15 mL). The solution was heated at 120° C. for 20 h. The reaction mixture was allowed to cool to ambient temperature then the mixture was diluted with water and NH₄OH solution. The mixture was extracted 3 times with EtOAc. The organic layer was dried over MgSO4, filtered and concentrated under vacuum. The residue was purified on a column of silica gel (6% MeOH/DCM) to give the subject compound (622 mg, yield 94%). Intermediate 19 was characterized by the following spectroscopic data: ¹H NMR (DMSO-d₆, 300 MHz) δ (ppm) 9.16 (s, 1H), 8.31 (d, 1H), 8.15 (d, 1H), 7.90 (m, 4H), 7.86 (m, 1H), 7.55 (m, 1H), 4.80 (s, 2H), 4.73 (m, 2H), 3.87 (m, 2H), 3.50 (m, 2H), 2.26 (m, 2H), 1.09 (t, 3H).

Intermediate 20

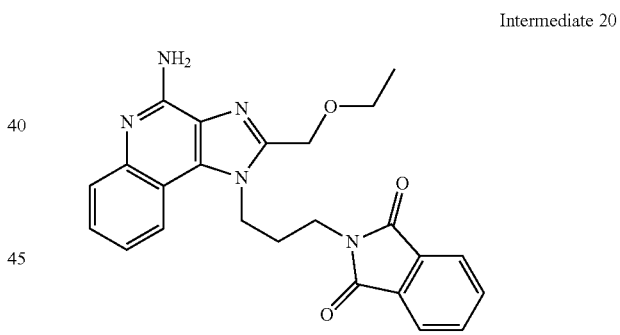

2-(3-(4-amino-2-(ethoxymethyl)-1H-imidazo[4,5-c]quinolin-1-yl)propyl)isoindoline-1,3-dione: The intermediate 19 (622 mg, 1.5 mmol) was dissolved in chloroform (5 mL). mCPBA (387 mg, 2.2 mmol) was added and the solution was heated at reflux overnight. The solution was then cooled and the solvents were removed at reduced pressure. The residue was then dissolved in dichloromethane (10 mL) and NH₄OH 20% solution (10 mL) was added to the stirred solution. The reaction mixture was refluxed overnight. A crystalline solid formed and was filtered from the mixture, washed with dichloromethane and hexane and dried to give the subject compound (341 mg, yield 53%). Intermediate 20 was characterized by the following spectroscopic data: ¹H NMR (DMSO-d₆, 300 MHz) δ (ppm) 7.92 (m, 5H), 7.62 (d, 1H), 7.43 (m, 1H), 7.15 (m, 1H), 6.60 (sl, 2H), 4.73 (s, 2H), 4.65 (m, 2H), 3.87 (m, 2H), 3.49 (q, 2H), 2.23 (m, 2H), 1.10 (t, 3H).

Intermediate 21

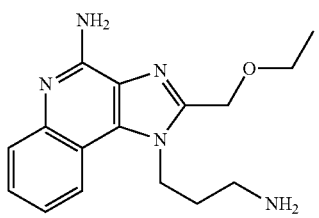

1-(3-aminopropyl)-2-(ethoxymethyl)-1H-imidazo[4,5-c]quinolin-4-amine: To a solution of intermediate 20 (341 mg, 0.79 mmol) in absolute EtOH (10 mL) was added hydrazine monohydrate (77 μL, 1.58 mmol). The reaction mixture was warmed to 90° C. and was stirred at this temperature overnight. Then, the solution was cooled to 0° C. and a solution of HCl 37% (100 μL) was added dropwise and the mixture was stirred for 2 h at 90° C. Then the mixture was cooled to rt, the solvents were removed in vacuo and the crude mixture was purified on column of silica gel (15% MeOH/DCM) to give the subject compound (200 mg, yield 85%). Intermediate 21 was characterized by the following spectroscopic data: $^1$H NMR (DMSO-$d_6$, 300 MHz) δ (ppm) 8.14 (d, 1H), 7.62 (d, 1H), 7.46 (m, 1H), 7.26 (m, 1H), 6.66 (sl, 2H), 4.78 (s, 2H), 4.68 (m, 2H), 3.59 (m, 2H), 2.95 (q, 2H), 2.16 (m, 2H), 1.19 (t, 3H).

Intermediate 22

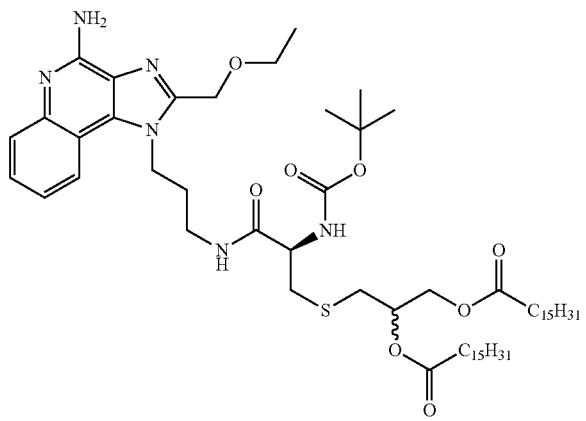

(R)-3-(3-(3-(4-amino-2-(ethoxymethyl)-1H-imidazo[4,5-c]quinolin-1-yl)propylamino)-2-(tert-butoxycarbonylamino)-3-oxopropylthio)propane-1,2-diyl dipalmitate: The title compound was prepared from intermediate 21 by following the procedure described for example 1, intermediate 13. Intermediate 22 was characterized by the following spectroscopic data: $^1$H NMR (DMSO-$d_6$, 300 MHz) δ (ppm) 8.17 (d, 1H), 7.66 (d, 1H), 7.49 (m, 1H), 7.29 (m, 1H), 6.69 (sl, 2H), 5.09 (m, 1H), 4.81 (s, 2H), 4.71 (m, 2H), 4.30-4.09 (m, 4H), 3.62 (m, 2H), 2.98 (q, 2H), 2.87-2.71 (m, 4H), 2.19 (m, 6H), 1.50 (m, 4H), 1.48 (s, 9H), 1.27 (m, 52H), 0.85 (m, 6H).

Compound 23

CL549

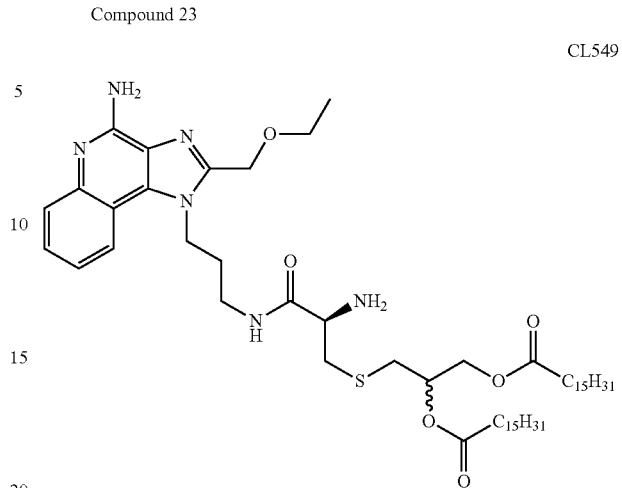

(R)-3-(2-amino-3-(3-(4-amino-2-(ethoxymethyl)-1H-imidazo[4,5-c]quinolin-1-yl)propyl amino)-3-oxopropylthio)propane-1,2-diyl dipalmitate: The title compound was prepared from intermediate 22 by following the procedure described for example 1, compound 14. Compound 11 was characterized by the following spectroscopic data: $^1$H NMR (DMSO-$d_6$, 300 MHz) δ (ppm) 8.14 (d, 1H), 7.62 (d, 1H), 7.46 (m, 1H), 7.26 (m, 1H), 6.66 (sl, 2H), 5.11 (m, 1H), 4.78 (s, 2H), 4.68 (m, 2H), 4.11-4.05 (m, 3H), 3.59 (m, 2H), 3.24 (m, 2H), 3.16-2.99 (m, 4H), 2.95 (q, 2H), 2.16 (m, 2H), 2.23 (m, 4H), 1.48 (m, 4H), 1.28 (m, 52H), 0.84 (m, 6H). MS (+)-ES [M+H]$^+$ 953.7.

Example 3

Molecule CL550

Intermediate 24

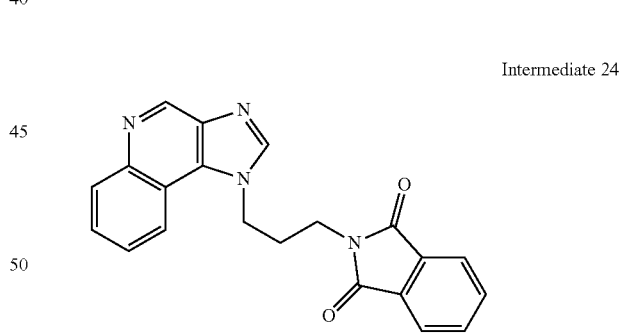

2-(3-(1H-imidazo[4,5-c]quinolin-1-yl)propyl)isoindoline-1,3-dione: The intermediate 18 (510 mg, 1.44 mole) was dissolved in triethyl orthoformate (15 mL). The solution was heated at 140° C. for 20 h. The reaction mixture was allowed to cool to ambient temperature then the reaction mixture was concentrated under vacuum. The residue was directly applied to a column of silica gel (6% MeOH/DCM) to give the subject compound (455 mg, yield 88%). Intermediate 24 was characterized by the following spectroscopic data: $^1$H NMR (DMSO-$d_6$, 300 MHz) δ (ppm) 8.81 (s, 1H), 8.22 (m, 1H), 7.98 (m, 1H), 7.92 (s, 1H), 7.88 (m, 4H), 7.78 (m, 1H), 7.60 (m, 1H), 4.55 (m, 2H), 4.05 (m, 2H), 2.65 (m, 2H).

Intermediate 25

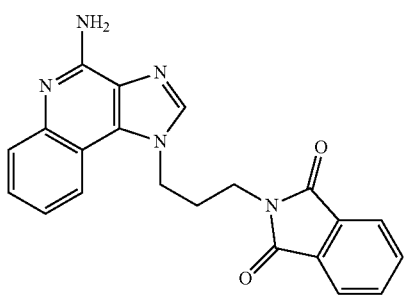

2-(3-(4-amino-1H-imidazo[4,5-c]quinolin-1-yl)propyl)isoindoline-1,3-dione

The title compound was prepared from intermediate 24 by following the procedure described for example 2, compound 20. Intermediate 25 was characterized by the following spectroscopic data: $^1$H NMR (DMSO-d$_6$, 300 MHz) δ (ppm) 8.10 (m, 1H), 7.95 (s, 1H), 7.86 (m, 4H), 7.75 (m, 1H), 7.69 (m, 1H), 7.37 (m, 1H), 6.96 (sl, 2H), 4.58 (m, 2H), 4.08 (m, 2H), 2.63 (m, 2H).

Intermediate 26

1-(3-aminopropyl)-1H-imidazo[4,5-c]quinolin-4-amine: The title compound was prepared from intermediate 25 by following the procedure described for example 2, compound 21. Intermediate 26 was characterized by the following spectroscopic data: $^1$H NMR (DMSO-d$_6$, 300 MHz) δ (ppm) 8.12 (m, 1H), 7.92 (s, 1H), 7.66 (d, 1H), 7.55 (m, 1H), 7.28 (m, 1H), 6.66 (sl, 2H), 4.68 (m, 2H), 2.92 (m, 2H), 2.16 (m, 2H).

Intermediate 27

(R)-3-(3-(3-(4-amino-1H-imidazo[4,5-c]quinolin-1-yl)propylamino)-2-(tert-butoxy carbonylamino)-3-oxopropyl-thio)propane-1,2-diyl dipalmitate: The title compound was prepared from intermediate 26 by following the procedure described for example 1, intermediate 13. Intermediate 27 was characterized by the following spectroscopic data: $^1$H NMR (DMSO-d$_6$, 300 MHz) δ (ppm) 8.13 (m, 1H), 7.83 (s, 1H), 7.65 (m, 1H), 7.54 (m, 1H), 7.24 (m, 1H), 6.15 (sl, 2H), 5.09 (m, 1H), 4.68 (m, 2H), 4.30-4.09 (m, 5H), 3.62 (m, 2H), 2.92 (m, 2H), 2.87-2.71 (m, 4H), 2.16 (m, 2H), 1.50 (m, 4H), 1.48 (s, 9H), 1.27 (m, 50H), 0.85 (m, 6H).

Compound 28

CL550

(R)-3-(2-amino-3-(3-(4-amino-1H-imidazo[4,5-c]quinolin-1-yl)propylamino)-3-oxopropyl thio)propane-1,2-diyl dipalmitate: The title compound was prepared from intermediate 27 by following the procedure described for example 1, compound 14. Compound 28 was characterized by the following spectroscopic data: $^1$H NMR (DMSO-d$_6$, 300 MHz) δ (ppm) 8.16 (m, 1H), 7.86 (s, 1H), 7.68 (m, 1H), 7.57 (m, 1H), 7.28 (m, 1H), 6.20 (sl, 2H), 5.09 (m, 1H), 4.68 (m, 2H), 4.30-4.09 (m, 4H), 3.62 (m, 4H), 2.92 (m, 2H), 2.87-2.71 (m, 4H), 2.16 (m, 2H), 1.50 (m, 4H), 1.27 (m, 50H), 0.85 (m, 6H). MS (+)-ES [M+H]$^+$ 895.6.

Example 4

Molecule CL551

Intermediate 29

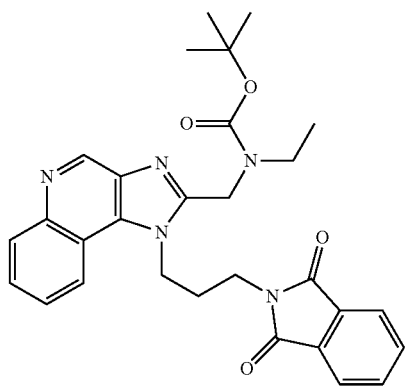

Tert-butyl-(1-(3-(1,3-dioxoisoindolin-2-yl)propyl)-1H-imidazo[4,5-c]quinolin-2-yl)methyl(ethyl)carbamate: The intermediate 18 (550 mg, 1.6 mole) was dissolved in N-Boc-N-Ethyl glycine (490 mg, 2.4 mmol). The solution was heated at 130° C. for 20 h. The reaction mixture was allowed to cool to rt then the mixture was diluted with water and NH₄OH solution. The mixture was extracted 3 times with EtOAc. The organic layer was dried over MgSO4, filtered and concentrated under vacuum. The residue was purified on a column of silica gel (6% MeOH/DCM) to give the subject compound (607 mg, yield 74%). Intermediate 29 was characterized by the following spectroscopic data: $^1$H NMR (DMSO-d$_6$, 300 MHz) δ (ppm) 8.81 (s, 1H), 8.22 (d, 1H), 7.98 (d, 1H), 7.88 (m, 4H), 7.78 (m, 1H), 7.60 (m, 1H), 4.22 (s, 2H), 4.55 (m, 2H), 3.75 (q, 2H), 3.60 (m, 2H), 2.28 (m, 2H), 1.38 (s, 9H), 1.09 (t, 3H).

Intermediate 30

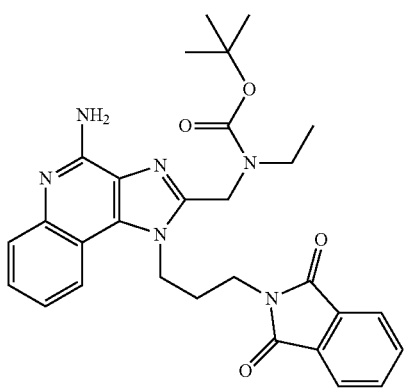

Tert-butyl-(4-amino-1-(3-(1,3-dioxoisoindolin-2-yl)propyl)-1H-imidazo[4,5-c]quinolin-2-yl)methyl(ethyl)carbamate: The title compound was prepared from intermediate 29 by following the procedure described for example 2, compound 20. Intermediate 30 was characterized by the following spectroscopic data: $^1$H NMR (DMSO-d$_6$, 300 MHz) δ (ppm) 8.10 (d, 1H), 7.92 (m, 4H), 7.65 (d, 1H), 7.44 (m, 1H), 7.16 (m, 1H), 6.86 (sl, 2H), 4.73 (m, 2H), 4.65 (s, 2H), 3.87 (m, 2H), 3.49 (q, 2H), 2.23 (m, 2H), 1.42 (s, 9H), 1.10 (t, 3H).

Intermediate 31

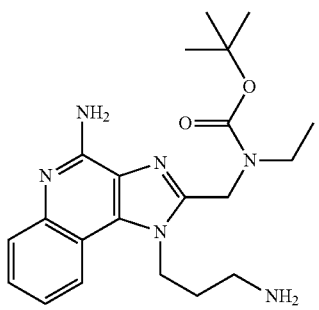

Tert-butyl-(4-amino-1-(3-aminopropyl)-1H-imidazo[4,5-c]quinolin-2-yl)methyl(ethyl)carbamate: The title compound was prepared from intermediate 30 by following the procedure described for example 2, compound 21. Intermediate 31 was characterized by the following spectroscopic data: $^1$H NMR (DMSO-d$_6$, 300 MHz) δ (ppm) 8.14 (d, 1H), 7.62 (d, 1H), 7.46 (m, 1H), 7.20 (m, 1H), 6.66 (sl, 2H), 4.73 (s, 2H), 4.65 (m, 2H), 3.67 (m, 2H), 3.55 (q, 2H), 2.25 (m, 2H), 1.42 (s, 9H), 1.10 (t, 3H).

Intermediate 32

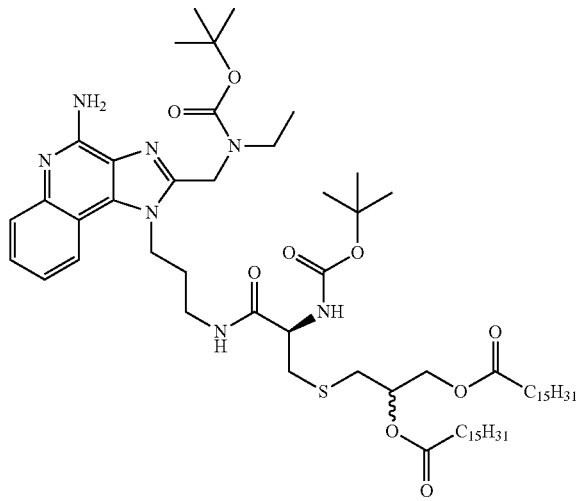

(R)-3-(3-(3-(4-amino-2-((tert-butoxycarbonyl(ethyl)amino)methyl)-1H-imidazo[4,5-c]quinolin-1-yl)propylamino)-2-(tert-butoxycarbonylamino)-3-oxopropylthio) propane-1,2-diyl dipalmitate: The title compound was prepared from intermediate 31 by following the procedure described for example 1, intermediate 13. Intermediate 32 was characterized by the following spectroscopic data: $^1$H NMR (DMSO-d$_6$, 300 MHz) δ (ppm) 8.14 (d, 1H), 7.62 (d, 1H), 7.46 (m, 1H), 7.20 (m, 1H), 6.66 (sl, 2H), 5.09 (m, 1H), 4.73 (s, 2H), 4.65 (m, 2H), 4.30-4.09 (m, 4H), 3.67 (m, 6H), 3.55 (q, 2H), 2.92 (m, 2H), 2.76 (m, 4H), 2.25 (m, 2H), 2.16 (m, 2H), 1.42 (s, 18H), 1.27 (m, 53H), 0.85 (m, 6H).

Compound 33

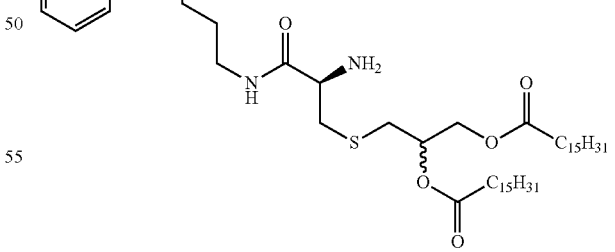

CL551

(R)-3-(2-amino-3-(3-(4-amino-2-((ethylamino)methyl)-1H-imidazo[4,5-c]quinolin-1-yl)propylamino)-3-oxopropylthio)propane-1,2-diyl dipalmitate: The title compound was prepared from intermediate 32 by following the procedure described for example 1, compound 14. Compound 33 was characterized by the following spectroscopic data: $^1$H NMR (DMSO-d$_6$, 300 MHz) δ (ppm) 8.17 (d, 1H), 7.63 (d, 1H), 7.49 (m, 1H), 7.21 (m, 1H), 6.67 (sl, 2H), 5.10 (m, 1H), 4.74 (s, 2H), 4.69 (m, 2H), 4.33-4.09 (m, 5H), 3.68 (m, 6H), 3.58 (q, 2H), 2.90 (m, 2H), 2.77 (m, 4H), 2.24 (m, 2H), 2.15 (m, 2H), 1.27 (m, 53H), 0.86 (m, 6H). MS (+)-ES [M+H]$^+$ 952.7.

Example 5

Molecule CL552

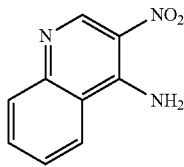

Intermediate 34

3-nitroquinolin-4-amine: To a solution of intermediate 16 (1.20 g, 5.7 mmol) in dioxane (50 mL) was added a solution of NH$_4$OH 20% (50 mL). The mixture was stirred at 120° C. for 1 h. The solvent was then removed in vacuo and the residue was dissolved in EtOAc (50 mL) and washed with water and brine. The organic layer was dried over MgSO$_4$, filtered and concentrated in vacuo. The crude compound was purified on column of silica gel (5% MeOH/DCM) to give the subject compound (1.09 g, yield 100%). Intermediate 34 was characterized by the following spectroscopic data: $^1$H NMR (DMSO-d$_6$, 300 MHz) δ (ppm) 9.18 (s, 1H), 9.01 (sl, 2H), 8.60 (d, 1H), 7.86 (m, 2H), 7.62 (m, 1H).

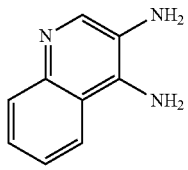

Intermediate 35

Quinoline-3,4-diamine: To a solution of intermediate 34 (1.09 g, 5.7 mmol) in a mixture of THF/MeOH (1/1) (60 mL) was added palladium on activated carbon 10% (0.05 eq). hydrogen gas was introduced via a balloon; the reaction mixture was stirred overnight at rt. The mixture was filtered through Celite and was washed with MeOH, the filtrate was concentrated in vacuo. The resulting solid was used for the next step without any further purification.

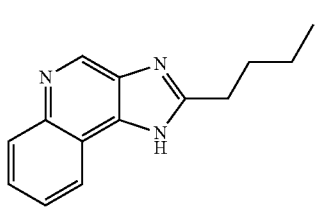

Intermediate 36

2-butyl-1H-imidazo[4,5-c]quinolone: The intermediate 17 (200 mg, 1.2 mmol) and valeric acid (5 ml, 4.53 mmol) were stirred at 130° C. under argon atmosphere overnight. The mixture was cooled and was diluted with water and NH$_4$OH solution (50 mL). The solution was extracted 3 times with EtOAc. The organic layer was washed with NaHCO3 solution water and brine, dried over MgSO4, filtered and concentrated in vacuo. The crude material was purified on column of silica gel (6% MeOH/DCM) to give the subject compound (170 mg, yield 60%). Intermediate 36 was characterized by the following spectroscopic data: $^1$H NMR (DMSO-d$_6$, 300 MHz) δ (ppm) 9.10 (s, 1H), 8.31 (s, 1H), 8.08 (m, 1H), 7.65 (m, 2H), 2.96 (t, 2H), 1.83 (m, 2H), 1.441 (m, 2H), 0.95 (t, 3H).

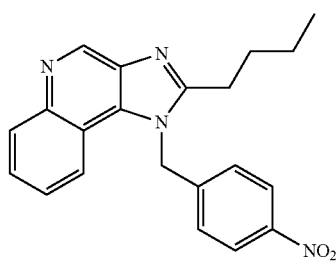

Intermediate 37

2-butyl-1-(4-nitrobenzyl)-1H-imidazo[4,5-c]quinolone: The intermediate 36 (170 mg, 0.754 mmol) and Cs$_2$CO$_3$ (246 mg, 0.7 mmol) were suspended in DMF (2 ml). 4-nitrobenzyl bromide (195 mg, 0.9 mmol) was added thereto and the mixture was stirred at room temperature for 18 h. The solvent was removed in vacuo, and the residue was dissolved in EtOAc (20 mL). The organic layer was washed with water and brine, dried on MgSO$_4$, filtered and the solvent was evaporated in vacuo. The residue was purified on column of silica gel (5% MeOH/DCM) to give the subject compound (179 mg, yield 65%). Intermediate 37 was characterized by the following spectroscopic data: $^1$H NMR (DMSO-d$_6$, 300 MHz) δ (ppm) 9.13 (s, 1H), 8.48 (m, 1H), 8.22 (m, 2H), 8.10 (m, 1H), 7.69 (d, 2H), 7.37 (d, 2H), 5.76 (s, 2H), 2.96 (m, 2H), 1.76 (m, 2H), 1.40 (m, 2H), 0.92 (t, 3H).

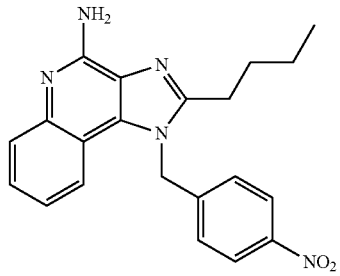

Intermediate 38

2-butyl-1-(4-nitrobenzyl)-1H-imidazo[4,5-c]quinolin-4-amine: The title compound was prepared from intermediate 37 by following the procedure described for example 2, compound 20. Intermediate 38 was characterized by the following spectroscopic data: $^1$H NMR (DMSO-d$_6$, 300 MHz) δ (ppm) 8.20 (m, 3H), 7.58 (d, 1H), 7.45 (m, 1H), 7.31 (m, 1H), 7.19 (d, 2H), 6.29 (sl, 2H), 5.98 (s, 2H), 2.89 (m, 2H), 1.72 (m, 2H), 1.39 (m, 2H), 0.87 (t, 3H).

Intermediate 39

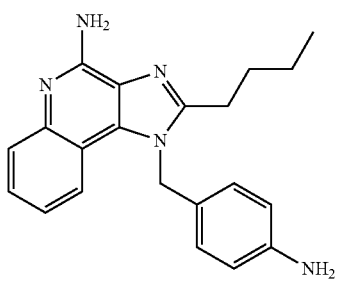

1-(4-aminobenzyl)-2-butyl-1H-imidazo[4,5-c]quinolin-4-amine: The title compound was prepared from intermediate 38 by following the procedure described for example 5, intermediate 35.

Intermediate 40

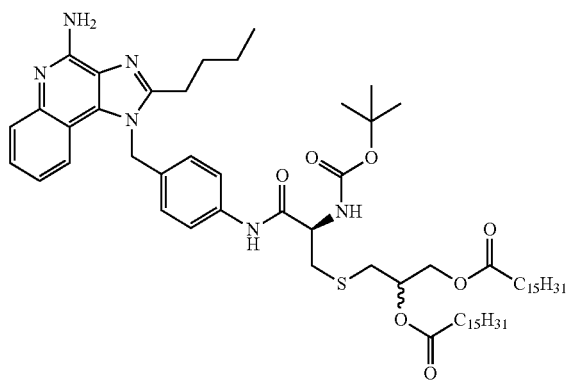

(R)-3-(3-(4-((4-amino-2-butyl-1H-imidazo[4,5-c]quinolin-1-yl)methyl)phenylamino)-2-(tert-butoxycarbonylamino)-3-oxopropylthio)propane-1,2-diyl dipalmitate: The title compound was prepared from intermediate 39 by following the procedure described for example 1, intermediate 13. Intermediate 40 was characterized by the following spectroscopic data: $^1$H NMR (DMSO-$d_6$, 300 MHz) δ (ppm) 8.20 (d, 1H), 7.60 (d, 1H), 7.46 (m, 1H), 7.31 (m, 1H), 6.76 (d, 2H), 6.45 (d, 2H), 6.38 (sl, 2H), 5.55 (s, 2H), 5.11 (m, 1H), 4.30-4.09 (m, 5H), 2.89 (m, 6H), 2.16 (m, 2H), 1.73 (m, 4H), 1.50 (m, 15H), 1.27 (m, 48H), 0.90 (m, 9H).

Compound 41

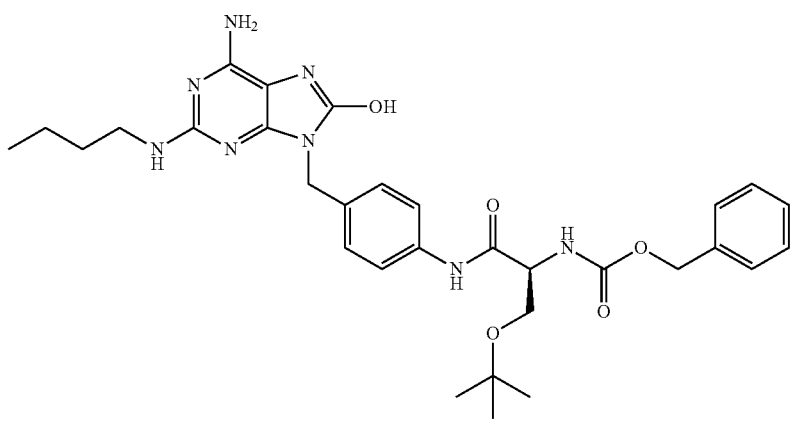

CL552

(R)-3-(2-amino-3-(4-((4-amino-2-butyl-1H-imidazo[4,5-c]quinolin-1-yl)methyl)phenyl amino)-3-oxopropylthio) propane-1,2-diyl dipalmitate: The title compound was prepared from intermediate 40 by following the procedure described for example 1, compound 14. Compound 41 was characterized by the following spectroscopic data: $^1$H NMR (DMSO-$d_6$, 300 MHz) δ (ppm) 8.21 (d, 1H), 7.62 (d, 1H), 7.47 (m, 1H), 7.33 (m, 1H), 6.75 (d, 2H), 6.45 (d, 2H), 6.39 (sl, 2H), 5.57 (s, 2H), 5.09 (m, 1H), 4.33-4.12 (m, 5H), 2.90 (m, 6H), 2.17 (m, 2H), 1.74 (m, 4H), 1.51 (m, 6H), 1.28 (m, 48H), 0.91 (m, 9H). MS (+)-ES [M+H]$^+$ 999.7.

Example 6

Molecule CL453

Intermediate 42

(S)-benzyl-1-(4-((6-amino-2-(butylamino)-8-hydroxy-9H-purin-9-yl)methyl)phenyl amino)-3-tert-butoxy-1-oxo-propan-2-ylcarbamate: To a solution of intermediate 5 (150 mg, 0.4 mmol) in dry DMF (10 mL) was added Z-Ser(otBu)OH (135 mg, 0.4 mmol), HATU (182 mg, 0.5 mmol), and N-methyl morpholine (151 µL, 1.4 mmol). The mixture was stirred at RT for 2 h. The solvent was then removed in vacuo and the residue was dissolved in DCM (50 mL) and washed with saturated NH₄Cl solution water and brine. The organic layer was dried over MgSO₄, filtered and concentrated in vacuo. The crude compound was purified on column of silica gel (3% MeOH/DCM) to give the subject compound (204 mg, yield 73%). Intermediate 42 was characterized by the following spectroscopic data: $^1$H NMR (DMSO-d$_6$, 300 MHz) δ (ppm) 9.98 (s, 1H), 9.60 (s, 1H), 7.55 (m, 2H), 7.26 (m, 7H), 6.19 (t, 1H), 5.98 (sl, 2H), 5.05 (s, 2H), 4.74 (s, 2H), 4.25 (t, 1H), 3.51 (m, 2H), 3.16 (m, 2H), 1.47 (m, 2H), 1.30 (m, 2H), 1.09 (s, 9H), 0.85 (t, 3H).

Intermediate 43

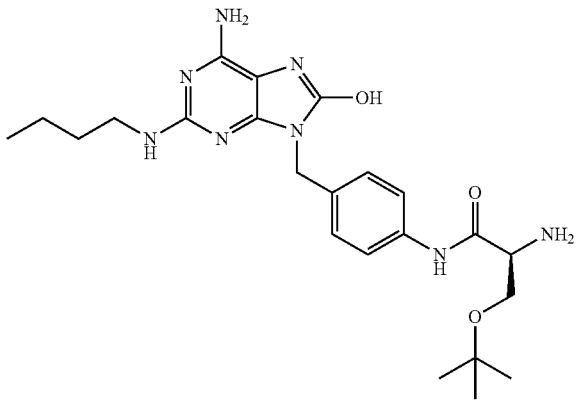

(S)-2-amino-N-(4-((6-amino-2-(butylamino)-8-hydroxy-9H-purin-9-yl)methyl)phenyl)-3-tert-butoxypropanamide: The title compound was prepared from intermediate 42 by following the procedure described for example 5, intermediate 35.

Intermediate 44

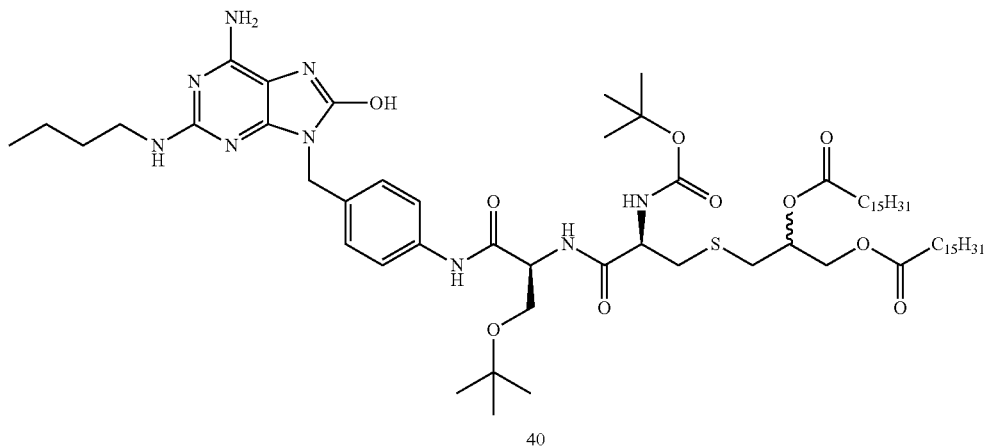

3-((R)-3-((S)-1-(4-((6-amino-2-(butylamino)-8-hydroxy-9H-purin-9-yl)methyl)phenyl amino)-3-tert-butoxy-1-oxo-propan-2-ylamino)-2-(tert-butoxycarbonylamino)-3-oxo propylthio)propane-1,2-diyl dipalmitate: The title compound was prepared from intermediate 43 by following the procedure described for example 1, intermediate 13. Intermediate 44 was characterized by the following spectroscopic data: $^1$H NMR (DMSO-d$_6$, 300 MHz) δ (ppm) 9.93 (s, 1H), 9.59 (s, 1H), 7.90 (m, 1H), 7.53 (m, 2H), 7.24 (m, 2H), 6.16 (t, 1H), 5.97 (sl, 2H), 5.09 (m, 1H), 4.74 (s, 2H), 4.46 (m, 1H), 4.26 (m, 1H), 4.13 (m, 2H), 3.51 (m, 2H), 3.18 (m, 2H), 2.89-2.54 (m, 4H), 2.26 (m, 4H), 1.48 (m, 6H), 1.43 (m, 9H), 1.28 (m, 52H), 1.09 (s, 9H), 0.89 (m, 9H).

Compound 45

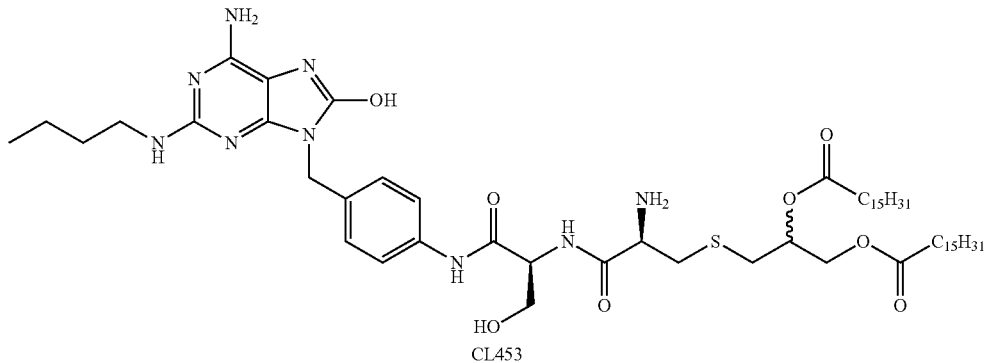

CL453

3-((R)-2-amino-3-((S)-1-(4-((6-amino-2-(butylamino)-8-hydroxy-9H-purin-9-yl)methyl)phenylamino)-3-hydroxy-1-oxopropan-2-ylamino)-3-oxopropylthio)propane-1,2-diyl dipalmitate: The title compound was prepared from intermediate 44 by following the procedure described for example 1, intermediate 14. Intermediate 45 was characterized by the following spectroscopic data: $^1$H NMR (DMSO-$d_6$, 300 MHz) δ (ppm) 9.97 (s, 1H), 9.73 (s, 1H), 8.25 (m, 1H), 7.52 (m, 2H), 7.25 (m, 2H), 6.14 (t, 1H), 6.04 (sl, 2H), 5.09 (m, 1H), 4.74 (s, 2H), 4.44 (m, 1H), 4.27 (m, 1H), 4.10 (m, 1H), 3.65 (m, 2H), 3.60 (m, 1H), 3.16 (m, 2H), 2.83-2.68 (m, 5H), 2.23 (m, 4H), 1.43 (m, 6H), 1.30 (m, 52H), 0.89 (m, 9H). MS (+)-ES [M+H]$^+$ 1068.7.

Example 7

Molecule CL446

Intermediate 46

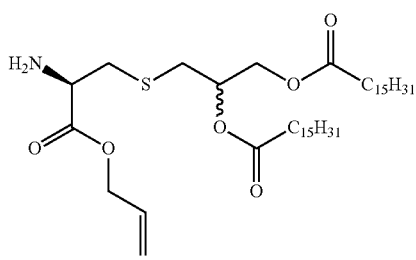

3-((R)-3-(allyloxy)-2-amino-3-oxopropylthio)propane-1,2-diyl dipalmitate: To a solution of intermediate 11 (9.55 g, 11.8 mmol) in DCM (100 mL) was added 25 mL of TFA. The mixture was stirred at RT overnight. Then the solvent were removed in vacuo, the residue was coevaporated 3 times with toluene. The residue was precipitated in diethyl ether to give the subject compound (9.71 g, yield 100%). Intermediate 46 was used for the next step without any further purification.

Intermediate 47

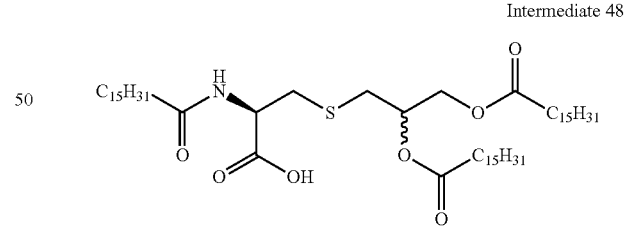

3-((R)-3-(allyloxy)-3-oxo-2-palmitamidopropylthio)propane-1,2-diyldipalmitate: To a solution of intermediate 46 (9.71 g, 11.8 mmol) in dry DMF (120 mL) were added HATU (4.69 g, 12.3 mmol), DIEA (4.07 mL, 23.5 mmol) and palmitic acid (3.16 g, 12.3 mmol). The mixture was stirred at rt overnight. The solvent was removed in vacuo. The residue was dissolved in DCM, washed with 0.1 N HCl solution water and brine. The organic layer was dried over MgSO$_4$, filtered and concentrated in vacuo. The crude compound was purified on column of silica gel (1% MeOH/DCM) to give the subject compound (10.9 g, yield 97%). Intermediate 47 was characterized by the following spectroscopic data: $^1$H NMR (CDCl$_3$-$d_1$, 300 MHz) δ (ppm) 6.35 (t, 1H), 5.92 (m, 1H), 5.34 (m, 2H), 5.14 (m, 1H), 4.87 (m, 1H), 4.67 (d, 2H), 4.33 (m, 1H), 4.16 (m, 1H), 3.09 (m, 2H), 2.73 (d, 2H), 2.33 (m, 6H), 1.61 (m, 6H), 1.28 (m, 72H), 0.89 (t, 9H).

Intermediate 48

(2R)-3-(2,3-bis(palmitoyloxy)propylthio)-2-palmitamidopropanoic acid: The title compound was prepared from intermediate 47 by following the procedure described for example 1, intermediate 12. Intermediate 48 was characterized by the following spectroscopic data: $^1$H NMR (CDCl$_3$-$d_1$, 300 MHz) δ (ppm) 5.18 (m, 1H), 4.76 (m, 1H), 4.35 (m, 1H), 4.16 (m, 1H), 3.14 (m, 2H), 2.75 (m, 2H), 2.34 (m, 6H), 1.64 (m, 6H), 1.25 (m, 72H), 0.89 (t, 9H).

Compound 49

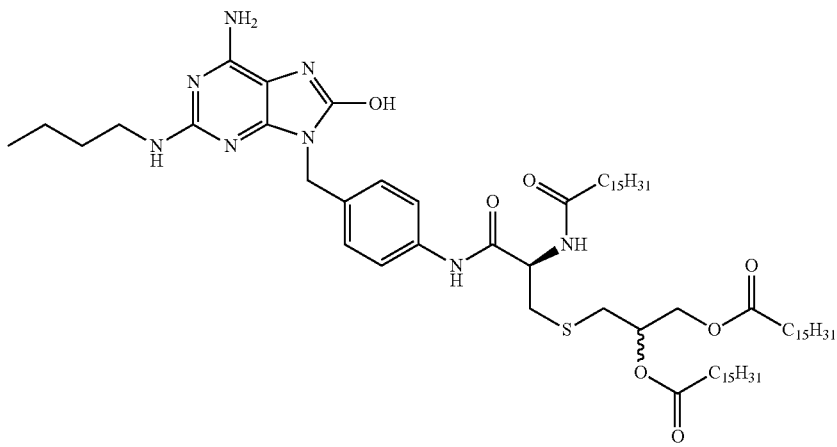

CL446

(R)-3-(3-(4-((6-amino-2-(butylamino)-8-hydroxy-9H-purin-9-yl)methyl)phenylamino)-3-oxo-2-palmitamidopropylthio)propane-1,2-diyl dipalmitate: The title compound was prepared from intermediate 5 and intermediate 48 by following the procedure described for example 1, intermediate 13. Intermediate 49 was characterized by the following spectroscopic data: $^1$H NMR (CDCl$_3$-d$_1$, 300 MHz) δ (ppm) 9.61 (s, 1H), 8.22 (m, 1H), 7.54 (d, 2H), 7.26 (d, 2H), 6.17 (t, 1H), 5.99 (sl, 2H), 5.14 (m, 1H), 4.76 (s, 2H), 4.27-4.13 (m, 4H), 3.18 (m, 2H), 2.29 (m, 6H), 1.93 (m, 10H), 1.28 (m, 76H), 0.86 (m, 12H). MS (+)-ES [M+H]$^+$ 1219.9.

Example 8

Molecule CL555

Intermediate 50

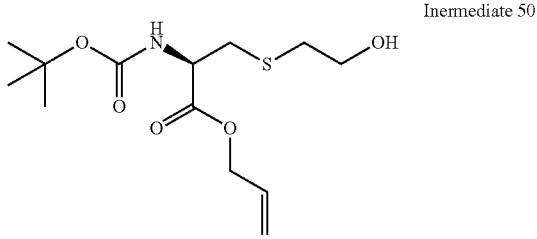 [SMILES: C=CCOC(=O)[C@H](CSCCO)NC(=O)OC(C)(C)C]

(R)-allyl 2-(tert-butoxycarbonylamino)-3-(2-hydroxyethylthio)propanoate: To a solution of intermediate 8 (10.85 g, 41.5 mmol) in dry DMF (150 mL) was added DIEA (14.37 mL, 83.0 mmol) and 2-bromoethanol (3.53 mL, 49.8 mmol). The mixture was stirred at 90° C. overnight. The solvent was then removed in vacuo and the residue was dissolved in EtOAc (200 mL) and washed with 0.1 N HCl solution water and brine. The organic layer was dried over MgSO$_4$, filtered and concentrated in vacuo. The crude compound was purified on column of silica gel (2% MeOH/DCM) to give the subject compound (10.3 g, yield 81%). Intermediate 50 was characterized by the following spectroscopic data: $^1$H NMR (CDCl$_3$-d$_1$, 300 MHz) δ (ppm) 5.88 (m, 1H), 5.32 (m, 1H), 5.23 (m, 2H), 4.59 (d, 2H), 4.51 (m, 1H), 3.68 (m, 2H), 2.94 (m, 2H), 2.86 (m, 2H), 2.44 (m, 1H), 1.46 (s, 9H).

Intermediate 51

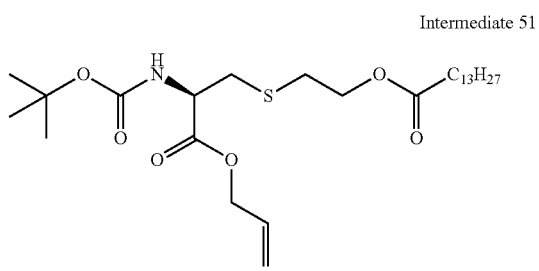

(R)-2-(3-(allyloxy)-2-(tert-butoxycarbonylamino)-3-oxopropylthio)ethyl tetradecanoate: A solution of intermediate 50 (1 g, 3.3 mmol) in dry DMF (20 mL) was cooled in an ice bath. EDCI (690 mg, 3.6 mmol), DMAP (440 mg, 3.6 mmol) and myristic acid (822 mg, 3.6 mmol) were added to the solution. The mixture was stirred for 10 min then warmed up to rt and stirred overnight. The reaction mixture was diluted with EtOAc, washed with 0.1 N HCl solution water and brine. The organic layer was dried over MgSO$_4$, filtered and concentrated in vacuo. The crude compound was purified on column of silica gel (1% DCM/MeOH) to give the subject compound (1.49 g, yield 88%). Intermediate 51 was characterized by the following spectroscopic data: $^1$H NMR (CDCl$_3$-d$_1$, 300 MHz) δ (ppm) 5.90 (m, 1H), 5.41-5.30 (m, 3H), 4.68 (d, 2H), 4.59 (m, 1H), 4.21 (t, 2H), 3.04 (m, 2H), 2.77 (m, 2H), 2.32 (m, 2H), 1.63 (m, 2H), 1.47 (s, 9H), 1.29 (s, 20H), 0.89 (t, 3H).

Intermediate 52

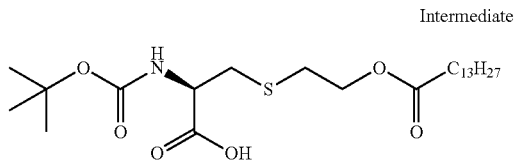

(R)-2-(tert-butoxycarbonylamino)-3-(2-(tetradecanoyloxy)ethylthio)propanoic Acid: The title compound was prepared from intermediate 51 by following the procedure described for example 1, compound 12. Intermediate 52 was characterized by the following spectroscopic data: $^1$H NMR (CDCl$_3$-d$_1$, 300 MHz) δ (ppm) 5.44 (m, 1H), 4.54 (m, 1H), 4.23 (t, 2H), 3.08 (m, 2H), 2.80 (t, 2H), 2.32 (t, 2H), 1.62 (m, 2H), 1.49 (s, 9H), 1.25 (s, 20H), 0.89 (t, 3H).

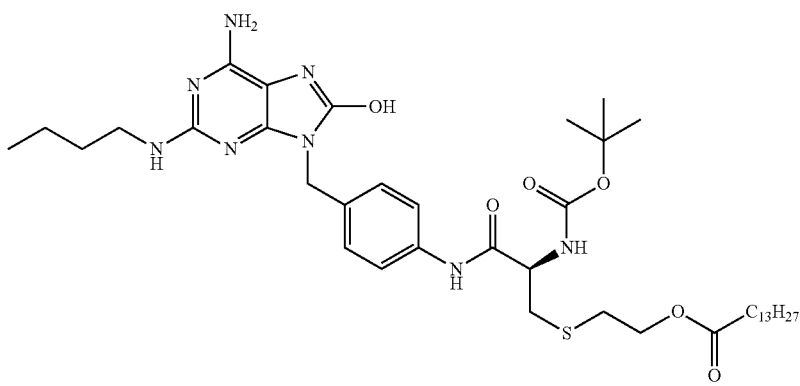

Intermediate 53

(R)-2-(3-(4-((6-amino-2-(butylamino)-8-hydroxy-9H-purin-9-yl)methyl)phenylamino)-2-(tert-butoxycarbonylamino)-3-oxopropylthio)ethyl tetradecanoate: The title compound was prepared from intermediate 5 and intermediate 52 by following the procedure described for example 1, compound 13. Intermediate 53 was characterized by the following spectroscopic data: $^1$H NMR (DMSO-$d_6$, 300 MHz) δ (ppm) 9.58 (sl, 1H), 7.52 (d, 2H), 7.24 (d, 2H), 7.10 (m, 1H), 6.14 (m, 1H), 5.96 (sl, 2H), 5.09 (m, 1H), 4.74 (s, 2H), 4.22-4.12 (m, 3H), 3.16 (m, 2H), 2.89-2.73 (m, 4H), 2.25 (t, 2H), 1.45 (m, 2H), 1.38 (s, 9H), 1.28 (m, 24H), 0.85 (m, 6H).

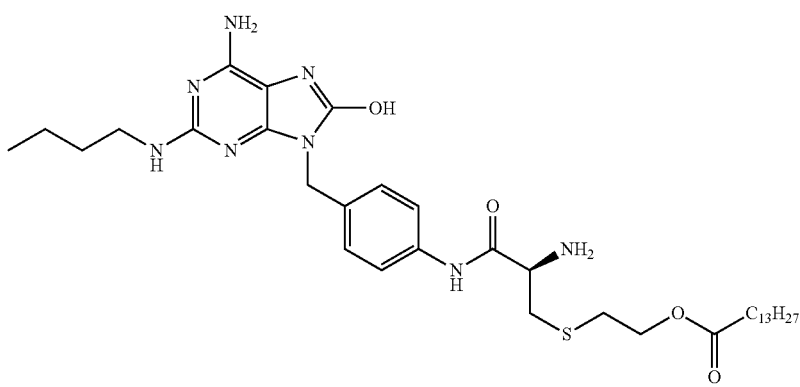

Compound 54

CL555

(R)-2-(2-amino-3-(4-((6-amino-2-(butylamino)-8-hydroxy-9H-purin-9-yl)methyl)phenyl amino)-3-oxopropylthio)ethyl tetradecanoate: The title compound was prepared from intermediate 53 by following the procedure described for example 1, compound 14. Compound 54 was characterized by the following spectroscopic data: $^1$H NMR (DMSO-$d_6$, 300 MHz) δ (ppm) 10.77 (sl, 1H), 8.45 (sl, 2H), 7.57 (d, 2H), 7.32 (d, 2H), 4.82 (s, 2H), 4.17 (m, 3H), 3.30 (m, 2H), 3.07-3.02 (m, 2H), 2.83 (m, 2H), 2.25 (t, 2H), 1.50 (m, 4H), 1.28 (m, 24H), 0.84 (m, 6H). MS (+)-ES [M+H]$^+$ 685.4.

Example 9

Molecule CL556

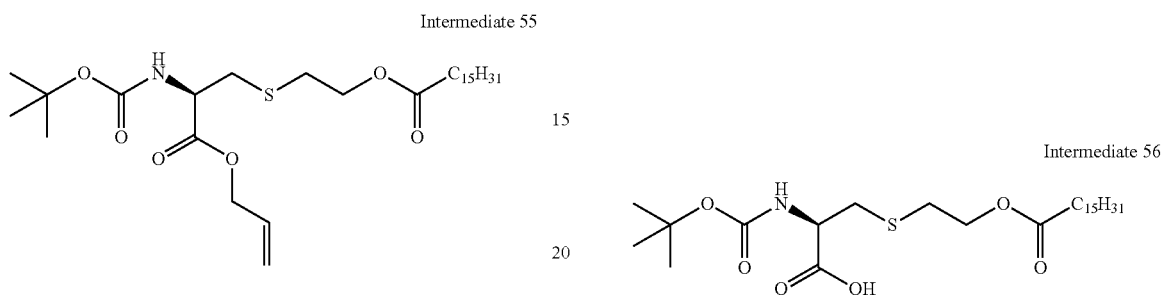

Intermediate 55

(R)-2-(3-(allyloxy)-2-(tert-butoxycarbonylamino)-3-oxo-propylthio)ethyl palmitate: A solution of intermediate 50 (1 g, 3.3 mmol) in dry DMF (20 mL) was cooled in an ice bath. EDCI (690 mg, 3.6 mmol), DMAP (440 mg, 3.6 mmol) and palmitic acid (924 mg, 3.6 mmol) were added to the solution. The mixture was stirred for 10 min then warmed up to room temperature and stirred overnight. The reaction mixture was diluted with EtOAc, washed with 0.1 N HCl solution water and brine. The organic layer was dried over $MgSO_4$, filtered and concentrated in vacuo. The crude compound was purified on column of silica gel (1% DCM/MeOH) to give the subject compound (1.19 g, yield 66%). Intermediate 55 was characterized by the following spectroscopic data: $^1$H NMR (CDCl$_3$-d$_1$, 300 MHz) δ (ppm) 5.96 (m, 1H), 5.33 (m, 3H), 4.67 (d, 2H), 4.58 (m, 1H), 4.22 (t, 2H), 3.04 (m, 2H), 2.78 (t, 2H), 2.33 (t, 2H), 1.64 (m, 2H), 1.46 (s, 9H), 1.27 (s, 24H), 0.89 (t, 3H).

Intermediate 56

(R)-2-(tert-butoxycarbonylamino)-3-(2-(palmitoyloxy)ethylthio)propanoic acid: The title compound was prepared from intermediate 55 by following the procedure described for example 1, compound 12. Intermediate 56 was characterized by the following spectroscopic data: $^1$H NMR (CDCl$_3$-d$_1$, 300 MHz) δ (ppm) 5.37 (m, 1H), 4.54 (m, 1H), 4.23 (t, 2H), 3.08 (m, 2H), 2.83 (t, 2H), 2.33 (t, 2H), 1.63 (m, 2H), 1.47 (s, 9H), 1.27 (s, 24H), 0.89 (t, 3H).

Intermediate 57

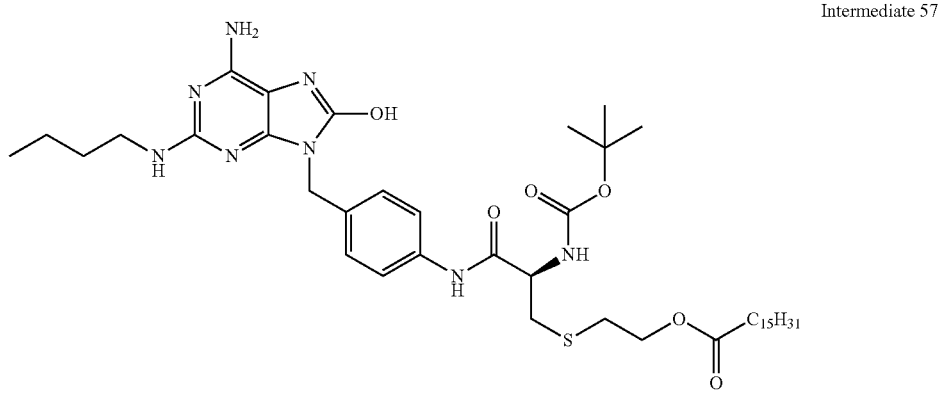

(R)-2-(3-(4-((6-amino-2-(butylamino)-8-hydroxy-9H-purin-9-yl)methyl)phenylamino)-2-(tert-butoxycarbonylamino)-3-oxopropylthio)ethyl palmitate: The title compound was prepared from intermediate 5 and intermediate 56 by following the procedure described for example 1, compound 13. Intermediate 57 was characterized by the following spectroscopic data: $^1$H NMR (DMSO-d$_6$, 300 MHz) δ (ppm) 9.58 (s, 1H), 7.52 (d, 2H), 7.25 (d, 2H), 7.14 (m, 1H), 6.15 (m, 1H), 5.95 (sl, 2H), 4.74 (s, 2H), 4.14 (m, 3H), 3.20 (m, 2H), 2.86-2.74 (m, 4H), 2.25 (t, 2H), 1.48-1.38 (m, 13H), 1.27 (m, 28H), 0.85 (m, 6H).

(R)-2-(3-(allyloxy)-2-(tert-butoxycarbonylamino)-3-oxopropylthio)ethyl stearate: A solution of intermediate 50 (1 g, 3.3 mmol) in dry DMF (20 mL) was cooled in an ice bath. EDCI (690 mg, 3.6 mmol), DMAP (440 mg, 3.6 mmol) and stearic acid (1.02 g, 3.6 mmol) were added to the solution. The mixture was stirred for 10 min then warmed up to room temperature and stirred overnight. The reaction mixture was diluted with EtOAc, washed with 0.1 N HCl solution water and brine. The organic layer was dried over MgSO$_4$, filtered and concentrated in vacuo. The crude compound was purified on column of silica gel (1% DCM/MeOH) to give the Compound 58

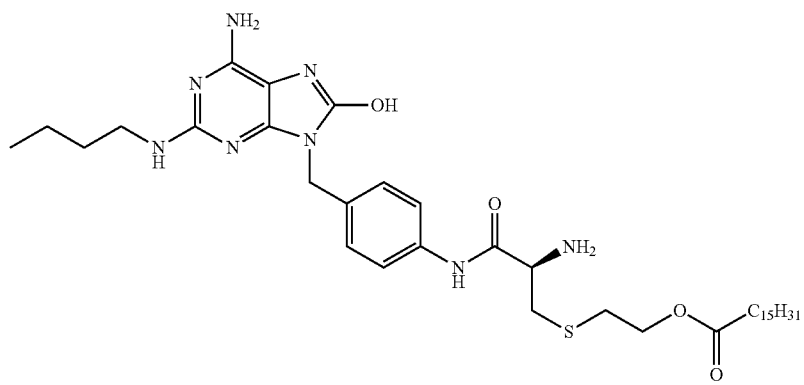

CL556

(R)-2-(2-amino-3-(4-((6-amino-2-(butylamino)-8-hydroxy-9H-purin-9-yl)methyl)phenyl amino)-3-oxopropylthio)ethyl palmitate: The title compound was prepared from intermediate 57 by following the procedure described for example 1, compound 14. Compound 58 was characterized by the following spectroscopic data: $^1$H NMR (DMSO-d$_6$, 300 MHz) δ (ppm) 8.45 (sl, 3H), 7.58 (d, 2H), 7.32 (d, 2H), 4.82 (s, 2H), 4.17 (m, 3H), 3.31 (m, 2H), 3.04 (m, 2H), 2.84 (m, 2H), 2.25 (t, 2H), 1.48 (m, 4H), 1.28 (m, 30H), 0.84 (m, 6H). MS (+)-ES [M+H]$^+$ 713.4.

subject compound (1.32 g, yield 70%). Intermediate 59 was characterized by the following spectroscopic data: $^1$H NMR (CDCl$_3$-d$_1$, 300 MHz) δ (ppm) 5.92 (m, 1H), 5.34 (m, 3H), 4.67 (d, 2H), 4.57 (m, 1H), 4.22 (t, 2H), 3.04 (m, 2H), 2.78 (t, 2H), 2.32 (t, 2H), 1.63 (m, 2H), 1.46 (s, 9H), 1.27 (s, 28H), 0.89 (t, 3H).

Example 10

Molecule CL557

Intermediate 60

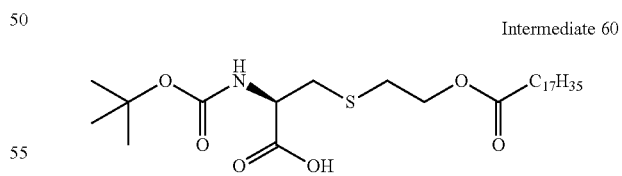

Intermediate 59

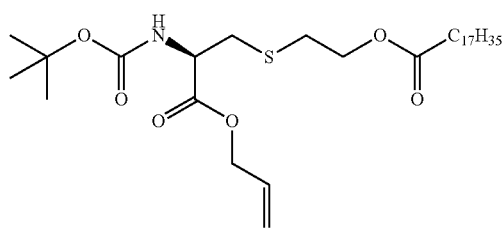

(R)-2-(tert-butoxycarbonylamino)-3-(2-(stearoyloxy)ethylthio)propanoic acid: The title compound was prepared from intermediate 59 by following the procedure described for example 1, compound 12. Intermediate 60 was characterized by the following spectroscopic data: $^1$H NMR (CDCl$_3$-d$_1$, 300 MHz) δ (ppm) 5.42 (m, 1H), 4.54 (m, 1H), 4.24 (t, 2H), 3.08 (m, 2H), 2.83 (t, 2H), 2.33 (t, 2H), 1.63 (m, 2H), 1.46 (s, 9H), 1.27 (s, 28H), 0.89 (t, 3H).

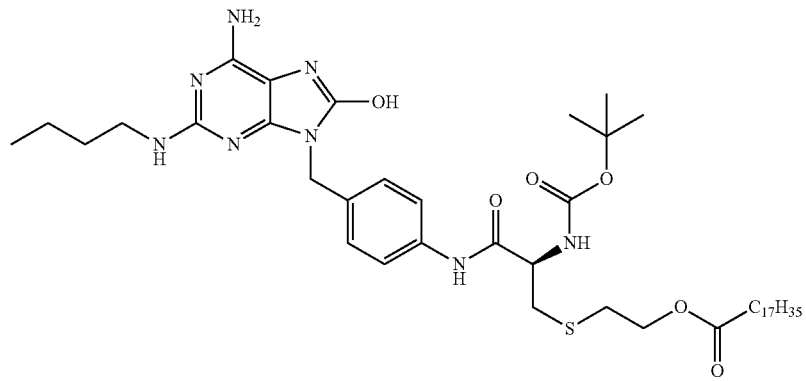

Intermediate 61

(R)-2-(3-(4-(((6-amino-2-(butylamino)-8-hydroxy-9H-purin-9-yl)methyl)phenylamino)-2-(tert-butoxycarbonylamino)-3-oxopropylthio)ethyl Stearate: The title compound was prepared from intermediate 5 and intermediate 60 by following the procedure described for example 1, compound 13. Intermediate 61 was characterized by the following spectroscopic data: $^1$H NMR (DMSO-d$_6$, 300 MHz) δ (ppm) 9.58 (sl, 1H), 7.52 (d, 2H), 7.25 (d, 2H), 7.16 (m, 1H), 6.14 (m, 1H), 5.95 (sl, 2H), 4.74 (s, 2H), 4.14 (m, 3H), 3.18 (m, 2H), 2.80-2.72 (m, 4H), 2.25 (t, 2H), 1.50 (m, 2H), 1.48 (s, 9H), 1.27 (m, 32H), 0.85 (m, 6H).

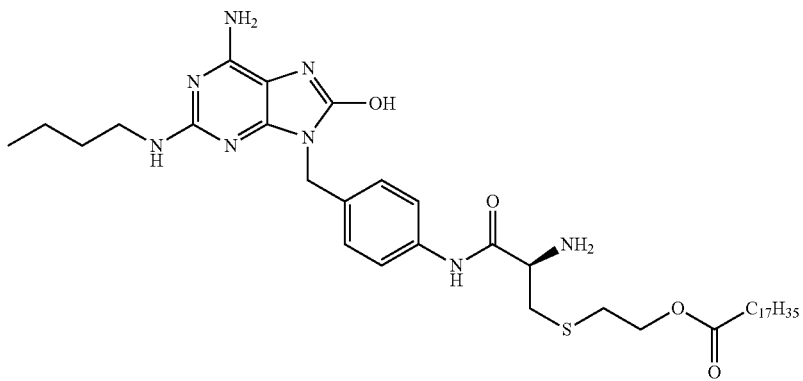

Compound 62

CL557

(R)-2-(2-amino-3-(4-(((6-amino-2-(butylamino)-8-hydroxy-9H-purin-9-yl)methyl)phenyl amino)-3-oxopropylthio)ethyl stearate: The title compound was prepared from intermediate 61 by following the procedure described for example 1, compound 14. Compound 62 was characterized by the following spectroscopic data: $^1$H NMR (DMSO-d$_6$, 300 MHz) δ (ppm) 10.85 (sl, 1H), 8.47 (sl, 2H), 7.58 (d, 2H), 7.32 (d, 2H), 4.82 (s, 2H), 4.17 (m, 3H), 3.45 (m, 2H), 3.05 (m, 2H), 2.83 (m, 4H), 2.25 (t, 2H), 1.51 (m, 4H), 1.28 (m, 32H), 0.84 (m, 6H). MS (+)-ES [M+H]$^+$ 741.5.

Example 11

Molecule CL558

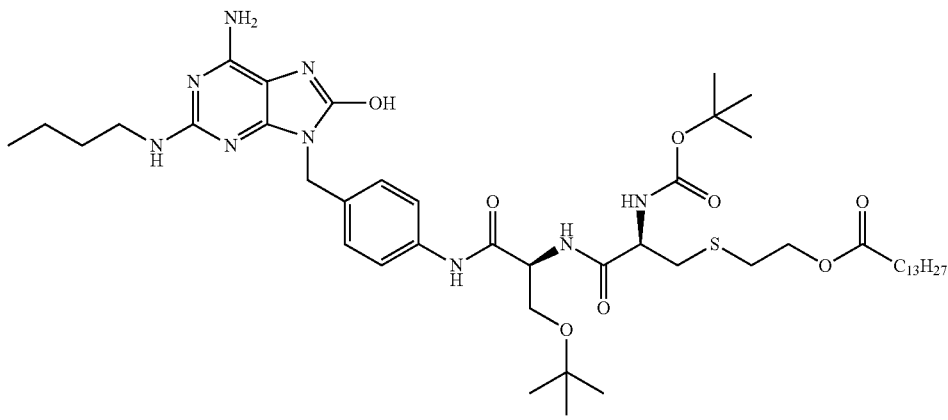

Intermediate 63

2-((R)-3-((S)-1-(4-((6-amino-2-(butylamino)-8-hydroxy-9H-purin-9-yl)methyl)phenyl amino)-3-tert-butoxy-1-oxopropan-2-ylamino)-2-(tert-butoxycarbonylamino)-3-oxo propylthio)ethyl tetradecanoate: The title compound was prepared from intermediate 43 and intermediate 52 by following the procedure described for example 1, compound 13. Intermediate 63 was characterized by the following spectroscopic data: $^1$H NMR (DMSO-$d_6$, 300 MHz) δ (ppm) 9.91 (s, 1H), 9.59 (sl, 1H), 7.95 (d, 1H), 7.51 (d, 2H), 7.25 (d, 2H), 7.05 (d, 1H), 6.15 (m, 1H), 5.96 (sl, 2H), 4.74 (s, 2H), 4.45 (m, 1H), 4.15 (m, 3H), 3.53 (m, 2H), 3.16 (m, 2H), 2.77-2.73 (m, 4H), 2.23 (t, 2H), 1.48 (m, 2H), 1.45 (s, 18H), 1.22 (m, 24H), 0.84 (m, 6H).

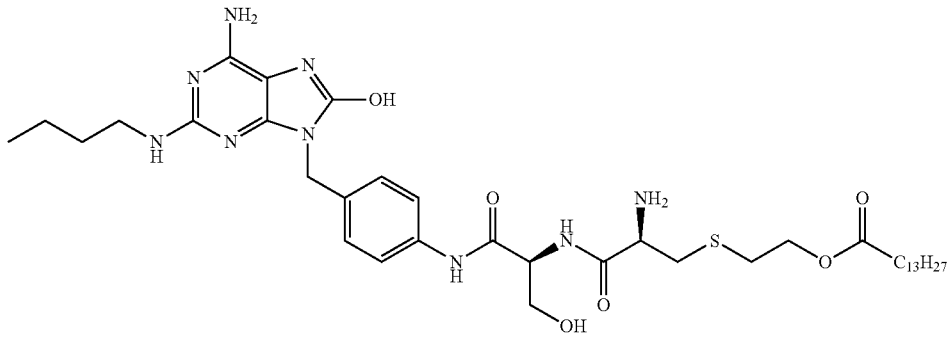

Compound 64

CL558

2-((R)-2-amino-3-((S)-1-(4-((6-amino-2-(butylamino)-8-hydroxy-9H-purin-9-yl)methyl)phenylamino)-3-hydroxy-1-oxopropan-2-ylamino)-3-oxopropylthio)ethyltetradecanoate: The title compound was prepared from intermediate 63 by following the procedure described for example 1, compound 14. Compound 64 was characterized by the following spectroscopic data: $^1$H NMR (DMSO-$d_6$, 300 MHz) δ (ppm) 10.56 (s, 1H), 10.12 (m, 1H), 8.88 (d, 1H), 8.37 (sl, 2H), 7.55 (d, 2H), 7.36 (d, 2H), 6.16 (m, 1H), 5.96 (sl, 2H), 4.75 (s, 2H), 4.48 (m, 1H), 4.08 (m, 2H), 3.63 (m, 2H), 3.16 (m, 2H), 2.95 (m, 4H), 2.25 (m, 2H), 1.50 (m, 4H), 1.28 (m, 24H), 0.84 (m, 6H). MS (+)-ES [M+H]$^+$ 772.4.

Example 12

Molecule CL559

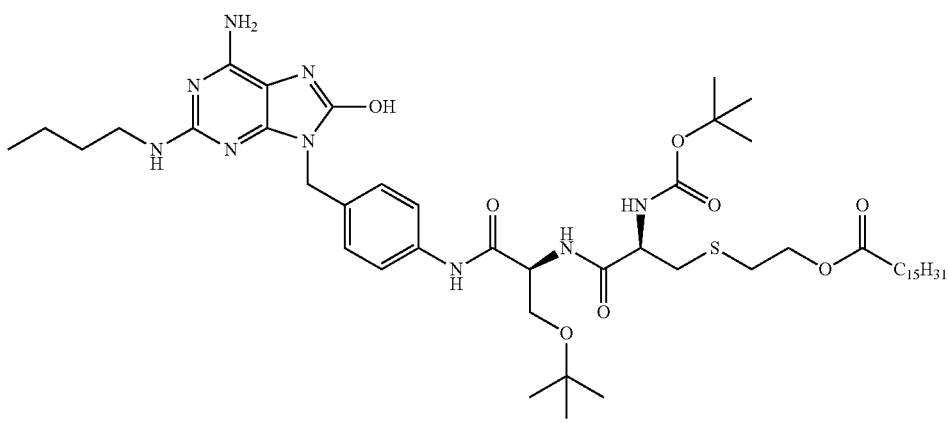

Intermediate 65

2-((R)-3-((S)-1-(4-((6-amino-2-(butylamino)-8-hydroxy-9H-purin-9-yl)methyl)phenyl amino)-3-tert-butoxy-1-oxopropan-2-ylamino)-2-(tert-butoxycarbonylamino)-3-oxo propylthio)ethyl palmitate: The title compound was prepared from intermediate 43 and intermediate 56 by following the procedure described for example 1, compound 13. Intermediate 65 was characterized by the following spectroscopic data: $^{1}$H NMR (DMSO-$d_6$, 300 MHz) δ (ppm) 9.91 (sl, 1H), 9.58 (s, 1H), 7.93 (d, 1H), 7.51 (d, 2H), 7.25 (d, 2H), 7.05 (d, 1H), 6.13 (m, 1H), 5.96 (sl, 2H), 4.74 (s, 2H), 4.48 (m, 1H), 4.13 (m, 3H), 3.52 (m, 2H), 3.15 (m, 2H), 2.78-2.73 (m, 4H), 2.26 (m, 2H), 1.48 (m, 4H), 1.43 (s, 11H), 1.27 (m, 24H), 1.10 (s, 9H), 0.85 (m, 6H).

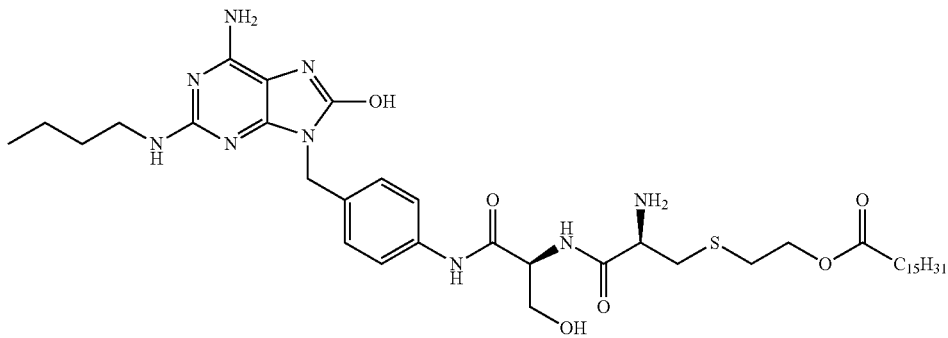

Compound 66

CL559

2-((R)-2-amino-3-((S)-1-(4-((6-amino-2-(butylamino)-8-hydroxy-9H-purin-9-yl)methyl)phenylamino)-3-hydroxy-1-oxopropan-2-ylamino)-3-oxopropylthio)ethyl palmitate: The title compound was prepared from intermediate 65 by following the procedure described for example 1, compound 14. Compound 66 was characterized by the following spectroscopic data: $^{1}$H NMR (DMSO-$d_6$, 300 MHz) δ (ppm) 10.76 (s, 1H), 10.16 (m, 1H), 8.93 (d, 1H), 8.35 (sl, 2H), 7.57 (d, 2H), 7.27 (d, 2H), 6.16 (m, 1H), 5.96 (sl, 2H), 4.79 (s, 2H), 4.52 (m, 1H), 4.15 (m, 3H), 3.69 (m, 2H), 3.36 (m, 2H), 2.82 (m, 4H), 2.26 (m, 2H), 1.51 (m, 4H), 1.28 (m, 28H), 0.85 (m, 6H). MS (+)-ES [M+H]$^+$ 800.5.

Example 13

Molecule CL560

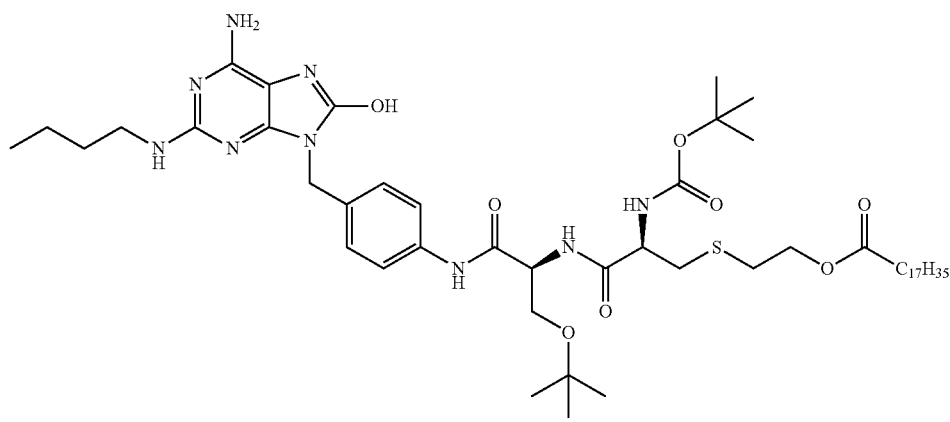

Intermediate 67

2-((R)-3-((S)-1-(4-((6-amino-2-(butylamino)-8-hydroxy-9H-purin-9-yl)methyl)phenyl amino)-3-tert-butoxy-1-oxo-propan-2-ylamino)-2-(tert-butoxycarbonylamino)-3-oxo propylthio)ethyl stearate: The title compound was prepared from intermediate 43 and intermediate 60 by following the procedure described for example 1, compound 13. Intermediate 67 was characterized by the following spectroscopic data: $^1$H NMR (DMSO-$d_6$, 300 MHz) δ (ppm) 9.91 (sl, 1H), 9.58 (s, 1H), 7.95 (d, 1H), 7.51 (d, 2H), 7.25 (d, 2H), 7.04 (d, 1H), 6.14 (m, 1H), 5.95 (sl, 2H), 4.74 (s, 2H), 4.48 (m, 1H), 4.13 (m, 3H), 3.52 (m, 2H), 3.18 (m, 2H), 2.77-2.73 (m, 4H), 2.26 (m, 2H), 1.50 (m, 4H), 1.48 (s, 11H), 1.27 (m, 28H), 1.08 (s, 9H), 0.85 (m, 6H).

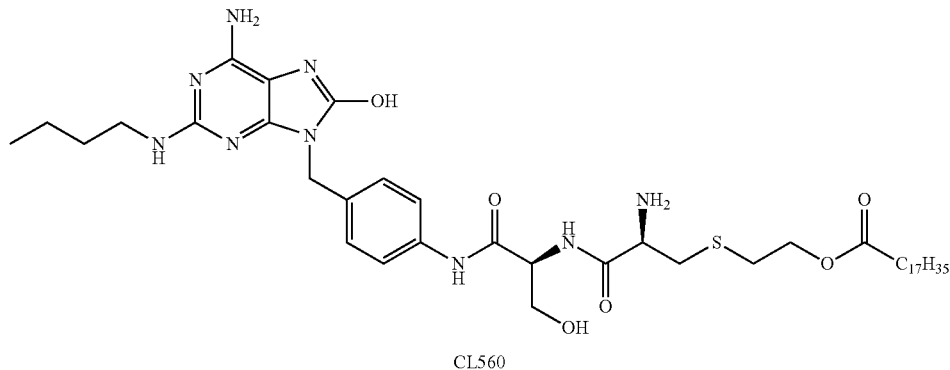

Compound 68

CL560

2-((R)-2-amino-3-((S)-1-(4-((6-amino-2-(butylamino)-8-hydroxy-9H-purin-9-yl)methyl)phenylamino)-3-hydroxy-1-oxopropan-2-ylamino)-3-oxopropylthio)ethyl stearate: The title compound was prepared from intermediate 67 by following the procedure described for example 1, compound 14. Compound 68 was characterized by the following spectroscopic data: $^1$H NMR (DMSO-$d_6$, 300 MHz) δ (ppm) 10.85 (s, 1H), 10.16 (m, 1H), 8.92 (d, 1H), 8.34 (sl, 2H), 7.56 (d, 2H), 7.26 (d, 2H), 6.16 (m, 1H), 5.96 (sl, 2H), 4.79 (s, 2H), 4.51 (m, 1H), 4.13 (m, 2H), 3.69 (m, 2H), 3.39 (m, 2H), 3.11-2.79 (m, 4H), 2.26 (m, 2H), 1.53 (m, 4H), 1.28 (m, 32H), 0.85 (m, 6H). MS (+)-ES [M+H]$^+$ 828.5.

Example 14

Molecule CL572

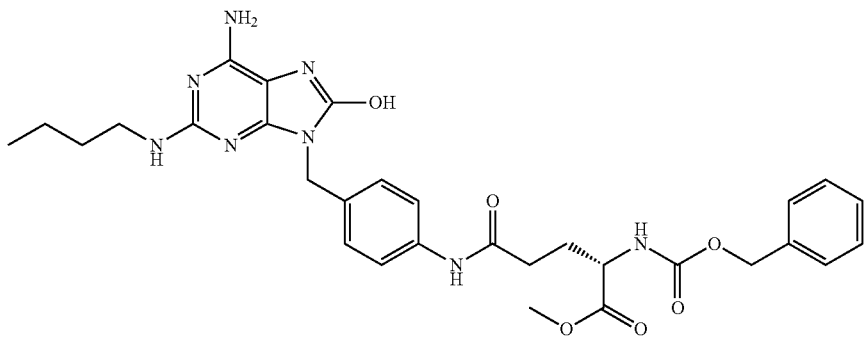

Intermediate 69

(S)-methyl-5-(4-((6-amino-2-(butylamino)-8-hydroxy-9H-purin-9-yl)methyl)phenyl amino)-2-(benzyloxycarbonylamino)-5-oxopentanoate: To a solution of intermediate 5 (530 mg, 1.6 mmol) in dry DMF (20 mL) was added Z-GluOMe (478 mg, 1.6 mmol), HATU (677 mg, 1.8 mmol), and DIEA (1.41 mL, 8.1 mmol). The mixture was stirred at RT for 4 h. The solvent was then removed in vacuo and the residue was dissolved in EtOAc (50 mL) and washed with saturated NaHCO$_3$ solution water and brine. The organic layer was dried over MgSO$_4$, filtered and concentrated in vacuo. The crude compound was purified on column of silica gel (3% MeOH/DCM) to give the subject compound (680 mg, yield 69%). Intermediate 69 was characterized by the following spectroscopic data: $^1$H NMR (DMSO-d$_6$, 300 MHz) δ (ppm) 9.89 (s, 1H), 9.59 (s, 1H), 7.76 (d, 1H), 7.49 (d, 2H), 7.35 (m, 5H), 7.22 (d, 2H), 6.18 (t, 1H), 5.98 (sl, 2H), 5.03 (s, 2H), 4.73 (s, 2H), 4.08 (m, 1H), 3.63 (s, 3H), 3.17 (m, 2H), 2.39 (m, 2H), 2.05 (m, 1H), 1.83 (m, 1H), 1.43 (m, 2H), 1.27 (m, 2H), 0.87 (t, 3H).

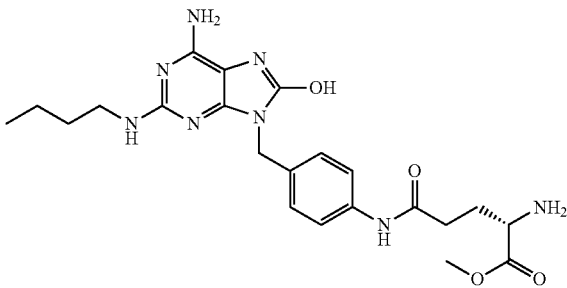

Intermediate 70

(S)-methyl-2-amino-5-(4-((6-amino-2-(butylamino)-8-hydroxy-9H-purin-9-yl)methyl)phenylamino)-5-oxopentanoate: The title compound was prepared from intermediate 69 by following the procedure described for example 5, intermediate 35.

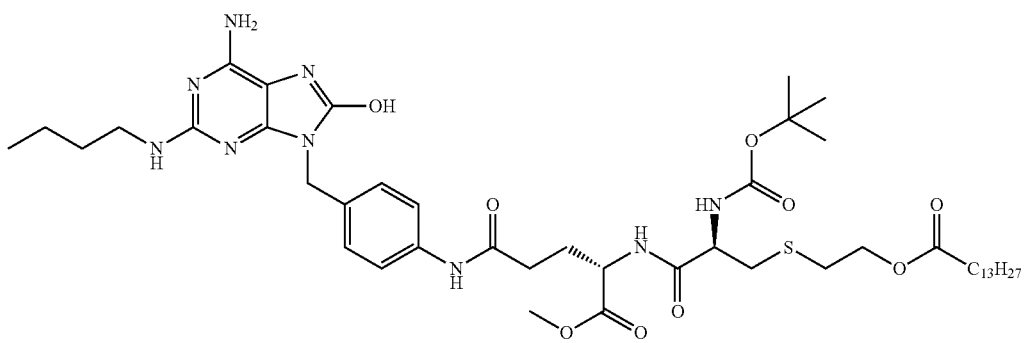

Intermediate 71

2-((R)-3-((S)-5-(4-((6-amino-2-(butylamino)-8-hydroxy-9H-purin-9-yl)methyl)phenyl amino)-1-methoxy-1,5-dioxopentan-2-ylamino)-2-(tert-butoxycarbonylamino)-3-oxopropylthio)ethyl tetradecanoate: The title compound was prepared from intermediate 70 and intermediate 52 by following the procedure described for example 1, intermediate 13. Intermediate 71 was characterized by the following spectroscopic data: $^1$H NMR (DMSO-d$_6$, 300 MHz) δ (ppm) 9.88 (s, 1H), 9.58 (s, 1H), 8.36 (d, 1H), 7.50 (m, 2H), 7.26 (m, 2H), 6.93 (d, 1H), 6.17 (t, 1H), 5.97 (sl, 2H), 4.73 (s, 2H), 4.28 (m, 1H), 4.13 (m, 2H), 3.61 (s, 3H), 3.51 (m, 2H), 3.16 (m, 2H), 2.90-2.55 (m, 4H), 2.38 (m, 2H), 2.28 (m, 2H), 2.03 (m, 1H), 1.83 (m, 1H), 1.48 (m, 4H), 1.43 (m, 9H), 1.28 (m, 21H), 0.89 (m, 6H).

(R)-2-(3-(3-(4-amino-2-(ethoxymethyl)-1H-imidazo[4,5-c]quinolin-1-yl)propylamino)-2-(tert-butoxycarbonylamino)-3-oxopropylthio)ethyl palmitate: The title compound was prepared from intermediate 21 and intermediate 56 by following the procedure described for example 1, compound 13. Intermediate 73 was characterized by the following spectroscopic data: $^1$H NMR (DMSO-d$_6$, 300 MHz) δ (ppm) 8.16 (d, 1H), 7.64 (d, 1H), 7.58 (m, 1H), 7.52-7.47 (m, 2H), 7.28 (m, 1H), 6.65 (sl, 2H), 5.00 (m, 1H), 4.82 (s, 2H), 4.74 (m, 2H), 4.68-4.23 (m, 4H), 3.66 (m, 2H), 3.12 (m, 2H), 2.95-2.83 (m, 4H), 2.35 (t, 2H), 1.70 (m, 2H), 1.48 (s, 9H), 1.25 (m, 27H), 0.89 (t, 3H).

Compound 72

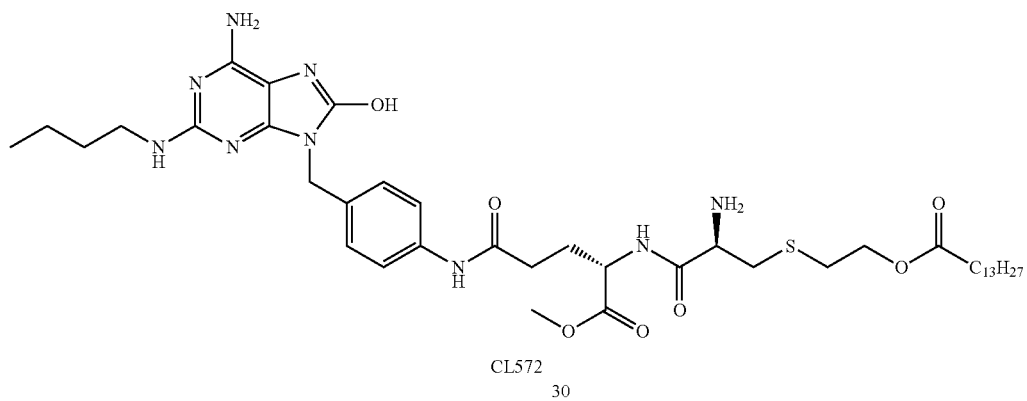

CL572

2-((R)-2-amino-3-((S)-5-(4-((6-amino-2-(butylamino)-8-hydroxy-9H-purin-9-yl)methyl)phenylamino)-1-methoxy-1,5-dioxopentan-2-ylamino)-3-oxopropylthio)ethyl tetradecanoate: The title compound was prepared from intermediate 71 by following the procedure described for example 1, intermediate 14. Intermediate 45 was characterized by the following spectroscopic data: $^1$H NMR (DMSO-d$_6$, 300 MHz) δ (ppm) 10.77 (s, 1H), 10.15 (s, 1H), 9.08 (d, 1H), 8.43 (sl, 2H), 7.91 (m, 1H), 7.56 (m, 2H), 7.25 (m, 2H), 4.78 (s, 2H), 4.36 (m, 1H), 4.18 (m, 2H), 4.02 (m, 1H), 3.64 (m, 2H), 3.60 (s, 3H), 3.31 (m, 2H), 3.08-2.83 (m, 5H), 2.28 (m, 2H), 2.08 (m, 1H), 1.85 (m, 1H), 1.50 (m, 4H), 1.23 (m, 21H), 0.89 (m, 6H). MS (+)-ES [M+H]$^+$ 828.5.

Example 15

Molecule CL567

Compound 74

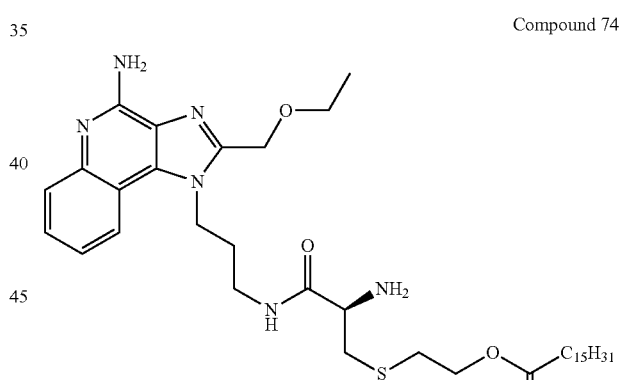

CL567

Intermediate 73

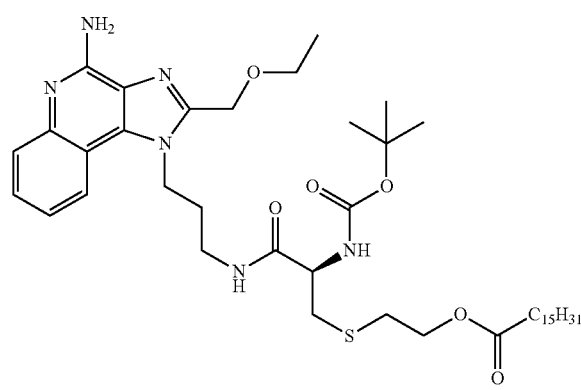

(R)-2-(2-amino-3-(3-(4-amino-2-(ethoxymethyl)-1H-imidazo[4,5-c]quinolin-1-yl)propyl amino)-3-oxopropylthio)ethyl palmitate: The title compound was prepared from intermediate 73 by following the procedure described for example 1, compound 14. Compound 74 was characterized by the following spectroscopic data: $^1$H NMR (DMSO-d$_6$, 300 MHz) δ (ppm) 8.42 (sl, 2H), 8.14 (d, 1H), 7.62 (d, 1H), 7.46 (m, 2H), 7.26 (m, 1H), 6.66 (sl, 2H), 4.98 (m, 1H), 4.78 (s, 2H), 4.76 (m, 2H), 4.66-4.21 (m, 4H), 3.64 (m, 2H), 3.10 (m, 2H), 2.93-2.80 (m, 4H), 2.35 (t, 2H), 1.75 (m, 2H), 1.27 (m, 24H), 1.19 (t, 3H), 0.89 (t, 3H). MS (+)-ES [M+H]$^+$ 685.4.

Example 16

Molecule CL568

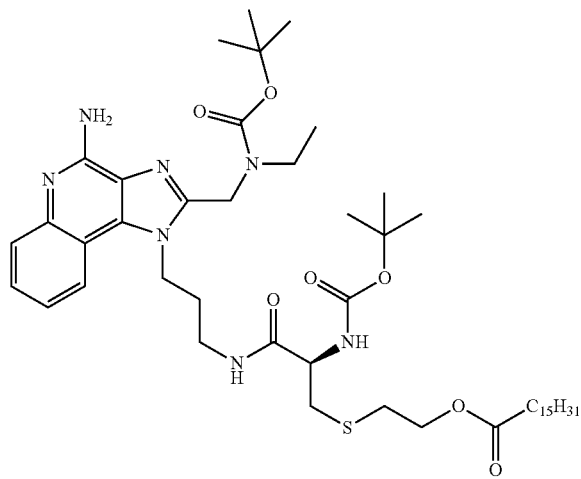

Intermediate 75

(R)-2-(3-(3-(4-amino-2-((tert-butoxycarbonyl(ethyl) amino)methyl)-1H-imidazo[4,5-c]quinolin-1-yl)propylamino)-2-(tert-butoxycarbonylamino)-3-oxopropylthio) ethyl palmitate: The title compound was prepared from intermediate 31 and intermediate 56 by following the procedure described for example 1, compound 13. Intermediate 75 was characterized by the following spectroscopic data: $^1$H NMR (DMSO-$d_6$, 300 MHz) δ (ppm) 8.14 (d, 1H), 7.62 (d, 1H), 7.46 (m, 1H), 7.20 (m, 1H), 6.66 (sl, 2H), 5.05 (m, 1H), 4.75 (s, 2H), 4.66 (m, 2H), 4.56 (m, 1H), 4.22 (t, 2H), 3.65 (m, 2H), 3.57 (m, 2H), 3.15 (m, 2H), 2.78 (t, 2H), 2.35 (t, 2H), 2.20 (m, 4H), 1.70 (m, 2H), 1.45 (s, 18H), 1.25 (t, 27H), 0.89 (t, 3H).

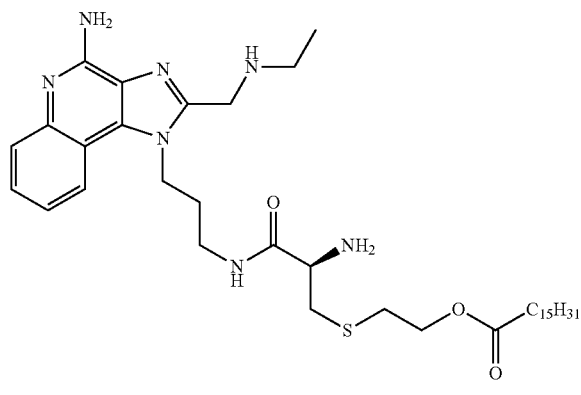

Compound 76

CL568

(R)-2-(2-amino-3-(3-(4-amino-2-((ethylamino)methyl)-1H-imidazo[4,5-c]quinolin-1-yl)propylamino)-3-oxopropylthio)ethyl palmitate: The title compound was prepared from intermediate 75 by following the procedure described for example 1, compound 14. Compound 76 was characterized by the following spectroscopic data: $^1$H NMR (DMSO-$d_6$, 300 MHz) δ (ppm) 8.37 (sl, 2H), 8.17 (d, 1H), 7.63 (d, 1H), 7.49-7.34 (m, 3H), 7.21 (m, 1H), 6.67 (sl, 2H), 5.01 (m, 1H), 4.76 (s, 2H), 4.75 (m, 2H), 4.60-4.20 (m, 4H), 3.68 (m, 2H), 3.15 (m, 2H), 2.90 (m, 2H), 2.77 (t, 2H), 2.34 (t, 2H), 1.70 (m, 2H), 1.27 (m, 24H), 1.20 (t, 3H), 0.89 (t, 3H). MS (+)-ES [M+H]$^+$ 684.5.

Example 17

In Vitro Testing of Conjugated Compounds of the Invention

Testing Activation of TLR7 and TLR2 Receptors

Some conjugated compounds of the invention were tested for their ability to activate TLR7 and TLR2 receptor signaling. Cell-based assays were carried out using TLR7 and TLR2 reporter cell lines (InvivoGen). The reporter cell lines are engineered HEK293 cells, a human embryonic kidney cell line (ATCC, CRL-1573) that stably express either murine TLR7 (HEK-Blue™ mTLR7) or human TLR7 (HEK-Blue™ hTLR7) or murine TLR2 (HEK-Blue™ mTLR2) or human TLR2 (HEK-Blue™ hTLR2) with an NF-κB-inducible secreted embryonic alkaline phosphatase (SEAP) as the reporter gene. The SEAP reporter gene is placed under the control of the NF-κB and AP-inducible promoter. Stimulation with the corresponding TLR ligand activates NF-κB and AP-1, which induces the production of SEAP. Detection of SEAP is measured following culturing cells in HEK-Blue™ Detection media (InvivoGen). HEK-Blue™ Detection contains a SEAP substrate, which upon hydrolysis by SEAP produces a colorimetric change allowing for detection of SEAP as the protein is secreted. The conjugated compounds were also assayed for their ability to activate both TLR7 and TLR2 in a physiological relevant cell line that naturally expresses these receptors to demonstrate their function as conjugated TLR7-TLR2 small molecule agonists. These assays were carried out using RAW-Blue™ Cells (InvivoGen), derived from RAW 264.7 mouse leukemic monocytic macrophage cell line (ATCC, CRL 2278) stably overexpressing a NF-κB/AP-1 inducible SEAP reporter constructs.

To perform the assay, cells were seeded on 96 well microliter plates at 50,000 or 100,000 cells per well for HEK-Blue™ Cells and RAW-Blue™ Cells respectively, and cultured at 37° C. in the presence of the conjugated compounds. The conjugated compounds were prepared as follows: First, stock solutions of the small molecule conjugated compounds of the invention were prepared in ethanol or water to a concentration of 10 mg/ml. A working dilution of the conjugated TLR7-TLR2 small molecules was made up in water and added to cells at a final range of concentrations from 10 μg/mL to 10 pg/ml. The working dilutions of the conjugated TLR7-TLR2 small molecules as the stated concentrations were directly added to the reporter cell lines and incubated at 37° C. for 24 hours. After 24 hours of incubation, the effect on reporter gene activity was determined by reading the OD at 655 nm using iMark™ Microplate Reader (BIO-RAD).

The conjugated compounds were tested alone for their ability to specifically activate TLR7 and TLR2, alongside the known TLR7 activators R848 or CL264 (InvivoGen) and the TLR2 agonists Pam$_2$CSK$_4$ or Pam$_3$CSK$_4$ (InvivoGen). The specificity of the TLR activity was determined by use of reporter cell lines to the other TLRs (data not shown). FIGS. 1A and 1B demonstrate the molecules of the invention that best activate hTLR7. FIGS. 2A and 2B demonstrate the molecules of the invention that best activate mTLR7. FIGS.

3A and 3B demonstrate the molecules of the invention that best activate hTLR2. FIG. 4 demonstrates the molecules of the invention that best activate mTLR2. FIGS. 5A and 5B demonstrate the molecules of the invention that best activate endogenous TLR7 to induce NF-κB in RAW-Blue™ Cells. Although RAW-Blue™ cells contain endogenous TLR2, the conjugated compounds of the invention that contain mono-acylated TLR2 agonist moiety selectively activate human but not murine TLR2 and therefore do not activate the endogenous TLR2 in RAW-Blue™ cells. Furthermore, these molecules containing mono-acylated TLR2 agonist moiety of the invention did not show any response when tested on the murine B16 mouse melanoma cell line, which endogenously express TLR2 but not TLR7 nor on a HEK293 cell line engineered to express bovine TLR2 (data not shown). In summary, the results demonstrate that conjugation of TLR7 agonist moieties to small molecule TLR2 agonist generates chimeras that retain TLR7 and TLR2 activity. The molecules show a tendency to activate mouse TLR7 with greater sensitivity than human TLR7. The conjugated compounds activate hTLR2 robustly, whereas, the mono-acylated compounds failed to induce mTLR2 and bTLR2. Furthermore, dose-dependent responses of the conjugated compounds indicate significant TLR activities of TLR7 and TLR2 compared to the corresponding controls.

All the variants conjugated compounds exhibit dual activities to TLR7 and TLR2 including derivatives of TLR7 agonists, 8-hydroxy purines or imidazoquinolines. These results indicate that the conjugation of small molecule TLR2 agonists to a TLR7 agonist moiety does not abrogate TLR7 or TLR2 activity.

Example 18

In Vivo Testing of Conjugated Small Molecule Agonist CL401 on a Mouse B16 Tumor Model To investigate whether administering in vivo a therapeutically effective amount of a composition concerned by the invention into a tumor environment affects tumor growth, C57BL/6 mice (Janvier S.A.S.) were shaved (on their backs) and were injected subcutaneously with approximately 50 μl ($5 \times 10^5$) of viable B16-F1 cells (ATCC, CRL-6323) under anesthesia, using 7 mice per group. Once the tumor volume reached about 5 mm in diameter, around day 7 after tumor cells were grafted, the mice were divided into 2 groups. A first group (control) received intra-tumoral injections of vehicle (Glucose 5% ethanol 8% that is often used to facilitate drug solubilization and so enhance delivery), for a total of 3 injections. All animal work was carried out at the animal facility at the Institut de Pharmacologie et de Biologie Structurale (IPBS) in Toulouse, in accordance with institutional guidelines. The second group received intra-tumoral injections of CL401 conjugated small molecule of the invention, selected for its superior TLR7 and TLR2 stimulatory activities in vitro, for a total of 3 injections. Tumor growth was significantly reduced in CL401-treated mice compared to the control mice. By day 51 following the tumor cell graft, 60% of mice in the CL401 conjugated TLR7-TLR2 small molecule treated group were still alive. In contrast, by day 26, there was no survival of mice from the control group of vehicle treated. Tumor growth was monitored and measured with calipers after day 5 of grafting tumor cells into mice and then every 2 days after. Measurements were performed under gas anesthesia. Tumor volume in mm$^3$ was determined according to the formula $V = W^2 \times L/2$, where L=length (mm) and W=width (mm)

FIG. 6A shows the significant reduction in tumor volume and FIG. 6B shows the increased rate of survival in mice treated with the CL401 conjugated TLR7-TLR2 small molecule compared to the vehicle control.

Altogether these data demonstrate that the conjugated small molecules of the invention are TLR7 and/or TLR8 and TLR2 agonists that induce an effective response to suppress tumor growth.

REFERENCES

Throughout this application, various references describe the state of the art to which this invention pertains. The disclosures of these references are hereby incorporated by reference into the present disclosure.

Biggadike et al., US 2011/0229500 A1 (Glaxo). Sep. 22, 2011. Purine derivatives for use in the treatment of allergic, inflammatory and infectious diseases.

Carson et al., US 2010/0210598 A1. Aug. 19 2010. Toll-like modulators and treatment of diseases.

Cook et al., US 2010/0240623 (AstraZeneca). Sep. 23, 2010. 8-oxoadenine derivatives acting as modulator of TLR7.

Finberg et al., US 2011/0152251. Jun. 23, 2011. Compounds for modulating TLR2.

Fink et al., U.S. Pat. No. 7,485,432 B2 (3M). Feb. 3, 2009. Selective Modulation of TLR-mediated biological Activity.

Gerster et al. U.S. Pat. No. 4,689,338. (Riker) Aug. 25, 1987. 1H-Imidazo[4,5-c]quinolin-4-amines and antiviral use.

Gorden et al., US 2011/0070575 A1 (Coley). Mar. 24, 2011 Immunomodulatory compositions, combinations and Methods (TLR7).

Isobe et al., US 2011/8044056 B2 (Sumitomo). Oct. 25, 2011. Adenine Compound.

Jackson et al., US 2010/0310595 A1. Dec. 9, 2010. Methods of Transfection and compositions therefor.

Johnson et al., US 2011/0282061 A1. (Glaxo). Nov. 17, 2011. Lipidated imidazoquinoline derviatives.

Jones et al., WO/2007/093901. Aug. 28, 2007. 3-Dezazapurine derivatives as TLR7 modulators.

Nakaar et al., US 2009/0028889 (Vaxinnate). Novel polypeptide ligands for Toll-like receptor 2.

Wu et al., US 2011/0053893 A1 (Novartis). Mar. 3, 2011. Compounds and compositions as TLR activity modulators.

Adams S. 2009. Toll-like receptor agonists in cancer therapy. *Immunotherapy* 1: 949-964.

Agnihotri G, Crall B M, Lewis T C, Day T P, Balakrishna R, Warshakoon H J, Malladi S S, David S A. 2011. Structure-activity relationships in toll-like receptor 2-agonists leading to simplified monoacyl lipopeptides. *Journal of medicinal chemistry* 54: 8148-8160.

Bennaceur K, Chapman J A, Touraine J L, Portoukalian J. 2009 Immunosuppressive networks in the tumour environment and their effect in dendritic cells. *Biochimica et biophysica acta* 1795: 16-24.

Bourquin C, Hotz C, Noerenberg D, Voelkl A, Heidegger S, Roetzer L C, Storch B, Sandholzer N, Wurzenberger C, Anz D et al. 2011. Systemic cancer therapy with a small molecule agonist of toll-like receptor 7 can be improved by circumventing TLR tolerance. *Cancer research* 71: 5123-5133.

Caproni E, Tritto E, Cortese M, Muzzi A, Mosca F, Monaci E, Baudner B, Seubert A, De Gregorio E. 2012. MF59 and Pam3CSK4 boost adaptive responses to influenza subunit vaccine through an IFN type I-independent mechanism of action. *J Immunol* 188: 3088-3098.

Curtin J F, Liu N, Candolfi M, Xiong W, Assi H, Yagiz K, Edwards M R, Michelsen K S, Kroeger K M, Liu C et al. 2009. HMGB1 mediates endogenous TLR2 activation and brain tumor regression. *PLoS medicine* 6: e10.

Duggan J M, You D, Cleaver J O, Larson D T, Garza R J, Guzman Pruneda F A, Tuvim M J, Zhang J, Dickey B F, Evans S E. 2011. Synergistic interactions of TLR2/6 and TLR9 induce a high level of resistance to lung infection in mice. *J Immunol* 186: 5916-5926.

El-Omar E M, Ng M T, Hold G L. 2008. Polymorphisms in Toll-like receptor genes and risk of cancer. *Oncogene* 27: 244-252.

Garaude J, Kent A, van Rooijen N, Blander J M. 2012. Simultaneous targeting of toll- and nod-like receptors induces effective tumor-specific immune responses. *Science translational medicine* 4: 120ra116.

Garay R P, Viens P, Bauer J, Normier G, Bardou M, Jeannin J F, Chiavaroli C. 2007. Cancer relapse under chemotherapy: why TLR2/4 receptor agonists can help. *European journal of pharmacology* 563: 1-17.

Hemmi H, Kaisho T, Takeuchi O, Sato S, Sanjo H, Hoshino K, Horiuchi T, Tomizawa H, Takeda K, Akira S. 2002. Small anti-viral compounds activate immune cells via the TLR7MyD88-dependent signaling pathway. *Nature immunology* 3: 196-200.

Hoebe K, Janssen E, Beutler B. 2004. The interface between innate and adaptive immunity. *Nature immunology* 5: 971-974.

Hotz C, Bourquin C. 2012. Systemic cancer immunotherapy with Toll-like receptor 7 agonists: Timing is everything. *Oncoimmunology* 1: 227-228.

Huang B, Zhao J, Unkeless J C, Feng Z H, Xiong H. 2008. TLR signaling by tumor and immune cells: a double-edged sword. *Oncogene* 27: 218-224.

Jayakumar A, Castilho T M, Park E, Goldsmith-Pestana K, Blackwell J M, McMahon-Pratt D. 2011. TLR1/2 activation during heterologous prime-boost vaccination (DNA-MVA) enhances CD8+ T Cell responses providing protection against Leishmania (Viannia). *PLoS neglected tropical diseases* 5: e1204.

Jones P, Pryde D C, Tran T D, Adam F M, Bish G, Cabo F, Ciaramella G, Dixon R, Duckworth J, Fox D N et al. 2011. Discovery of a highly potent series of TLR7 agonists. *Bioorganic & medicinal chemistry letters* 21: 5939-5943.

Kanzler H, Barrat F J, Hessel E M, Coffman R L. 2007. Therapeutic targeting of innate immunity with Toll-like receptor agonists and antagonists. *Nature medicine* 13: 552-559.

Kauffman E C, Liu H, Schwartz M J, Scherr D S. 2012. Toll-like receptor 7 agonist therapy with imidazoquinoline enhances cancer cell death and increases lymphocytic infiltration and proinflammatory cytokine production in established tumors of a renal cell carcinoma mouse model. *Journal of oncology* 2012: 103298.

Kawai T, Akira S. 2011. Toll-like receptors and their crosstalk with other innate receptors in infection and immunity. *Immunity* 34: 637-650.

Krieg A M. 2008. Toll-like receptor 9 (TLR9) agonists in the treatment of cancer. *Oncogene* 27: 161-167.

Kurimoto A, Ogino T, Ichii S, Isobe Y, Tobe M, Ogita H, Takaku H, Sajiki H, Hirota K, Kawakami H. 2004. Synthesis and evaluation of 2-substituted 8-hydroxyadenines as potent interferon inducers with improved oral bioavailabilities. *Bioorganic & medicinal chemistry* 12: 1091-1099.

Kutikhin AG. 2011. Association of polymorphisms in TLR genes and in genes of the Toll-like receptor signaling pathway with cancer risk. *Human immunology* 72: 1095-1116.

Leah E. 2011. Rheumatoid arthritis: spontaneous release of cytokines from synovial tissue is blocked by anti-TLR2. *Nature Reviews Rheumatology* 7: 254.

Lee J, Chuang T H, Redecke V, She L, Pitha P M, Carson D A, Raz E, Cottam H B. 2003. Molecular basis for the immunostimulatory activity of guanine nucleoside analogs: activation of Toll-like receptor 7. *Proceedings of the National Academy of Sciences of the United States of America* 100: 6646-6651.

Lombardi V, Van Overtvelt L, Horiot S, Moussu H, Chabre H, Louise A, Balazuc A M, Mascarell L, Moingeon P. 2008. Toll-like receptor 2 agonist Pam3CSK4 enhances the induction of antigen-specific tolerance via the sublingual route. *Clinical and experimental allergy: journal of the British Society for Allergy and Clinical Immunology* 38: 1819-1829.

MacLeod H, Wetzler L M. 2007. T cell activation by TLRs: a role for TLRs in the adaptive immune response. *Science's STKE: signal transduction knowledge environment* 2007: pe48.

Mandal R K, George G P, Mittal R D. 2012. Association of Toll-like receptor (TLR) 2, 3 and 9 genes polymorphism with prostate cancer risk in North Indian population. *Molecular biology reports* 39: 7263-7269.

Metzger J W, Beck-Sickinger A G, Loleit M, Eckert M, Bessler W G, Jung G. 1995. Synthetic S-(2,3-dihydroxypropyl)-cysteinyl peptides derived from the N-terminus of the cytochrome subunit of the photoreaction centre of *Rhodopseudomonas viridis* enhance murine splenocyte proliferation. *Journal of peptide science: an official publication of the European Peptide Society* 1: 184-190.

Meyer T, Stockfleth E. 2008. Clinical investigations of Toll-like receptor agonists. *Expert opinion on investigational drugs* 17: 1051-1065.

Muhlradt P F, Kiess M, Meyer H, Sussmuth R, Jung G. 1998. Structure and specific activity of macrophage-stimulating lipopeptides from *Mycoplasma hyorhinis*. *Infection and immunity* 66: 4804-4810.

Newton K, Dixit V M. 2012. Signaling in innate immunity and inflammation. *Cold Spring Harbor perspectives in biology* 4.

Okusawa T, Fujita M, Nakamura J, Into T, Yasuda M, Yoshimura A, Hara Y, Hasebe A, Golenbock D T, Morita M, Kuroki Y, Ogawa T, Shibata K. 2004. Relationship between structures and biological activities of mycoplasmal diacylated lipopeptides and their recognition by toll-like receptors 2 and 6. *Infect Immun.* 72: 1657-1665.

Palsson-McDermott E M, O'Neill L A. 2007. The potential of targeting Toll-like receptor 2 in autoimmune and inflammatory diseases. *Ir J Med Sci.* 176; 253-260.

Pasare C, Medzhitov R. 2005. Toll-like receptors: linking innate and adaptive immunity. *Advances in experimental medicine and biology* 560: 11-18.

Rakoff-Nahoum S, Medzhitov R. 2009. Toll-like receptors and cancer. *Nature reviews Cancer* 9: 57-63.

Sacht G, Marten A, Deiters U, Sussmuth R, Jung G, Wingender E, Muhlradt P F. 1998. Activation of nuclear factor-kappaB in macrophages by mycoplasmal lipopeptides. *European journal of immunology* 28: 4207-4212.

Salaun B, Zitvogel L, Asselin-Paturel C, Morel Y, Chemin K, Dubois C, Massacrier C, Conforti R, Chenard M P, Sabourin J C et al. 2011. TLR3 as a biomarker for the therapeutic efficacy of double-stranded RNA in breast cancer. *Cancer research* 71: 1607-1614.

Salunke D B, Shukla N M, Yoo E, Crall B M, Balakrishna R, Malladi S S, David S A. 2012. Structure-activity relationships in human Toll-like receptor 2-specific monoacyl lipopeptides. *Journal of medicinal chemistry* 55: 3353-3363.

Sato Y, Goto Y, Narita N, Hoon D S. 2009. Cancer Cells Expressing Toll-like Receptors and the Tumor Microenvironment. *Cancer microenvironment: official journal of the International Cancer Microenvironment Society* 2 Suppl 1: 205-214.

Schmidt J, Welsch T, Jager D, Muhlradt P F, Buehler M W, Marten A. 2007. Intratumoural injection of the toll-like receptor-2/6 agonist 'macrophage-activating lipopeptide-2' in patients with pancreatic carcinoma: a phase I/II trial. *British journal of cancer* 97: 598-604.

Schon M P, Schon M. 2004. Immune modulation and apoptosis induction: two sides of the antitumoral activity of imiquimod. *Apoptosis: an international journal on programmed cell death* 9: 291-298.

Smits E L, Ponsaerts P, Berneman Z N, Van Tendeloo V F. 2008. The use of TLR7 and TLR8 ligands for the enhancement of cancer immunotherapy. *The oncologist* 13: 859-875.

So E Y, Ouchi T. 2010. The application of Toll like receptors for cancer therapy. *International journal of biological sciences* 6: 675-681.

Tuvim M J, Gilbert B E, Dickey B F, Evans S E. 2012. Synergistic TLR2/6 and TLR9 activation protects mice against lethal influenza pneumonia. *PloS one* 7: e30596.

Wang R F, Miyahara Y, Wang H Y. 2008. Toll-like receptors and immune regulation: implications for cancer therapy. *Oncogene* 27: 181-189.

Whitmore M M, DeVeer M J, Edling A, Oates R K, Simons B, Lindner D, Williams B R. 2004. Synergistic activation of innate immunity by double-stranded RNA and CpG DNA promotes enhanced antitumor activity. *Cancer research* 64: 5850-5860.

Wiesmuller K H, Bessler W, Jung G. 1983. Synthesis of the mitogenic S-[2,3-bis(palmitoyloxy)propyl]-N-palmitoyl-pentapeptide from *Escherichia coli* lipoprotein. *Hoppe-Seyler's Zeitschrift fur physiologische Chemie* 364: 593-606.

Zahringer U, Lindner B, Inamura S, Heine H, Alexander C. 2008. TLR2-promiscuous or specific? A critical re-evaluation of a receptor expressing apparent broad specificity. *Immunobiology* 213: 205-224.

Zhang Y, Luo F, Cai Y, Liu N, Wang L, Xu D, Chu Y. 2011. TLR1/TLR2 agonist induces tumor regression by reciprocal modulation of effector and regulatory T cells. *J Immunol* 186: 1963-1969.

The invention claimed is:

1. A conjugated compound of Formula I:

Q-Z—$R^4$     Formula I wherein Q is a purine derivative agonist of TLR7 and/or TLR8 and Z—$R^4$ is a TLR2 agonist, said conjugated compound being chosen among compounds of Formula II:

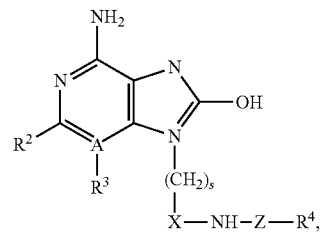

Formula II a tautomer thereof or a pharmaceutically acceptable salt, solvate or polymorph of said compound or tautomer, wherein:
$R^2$ is a $C_1$-$C_{10}$ alkylamino;
X is a phenylene;
and
Z—$R^4$ is a TLR2 agonist selected from the group consisting of:

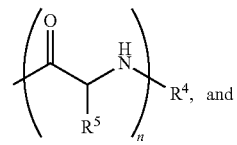

Formula III

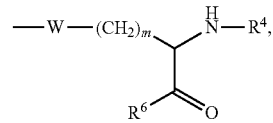

Formula IV wherein:
$R^5$ is the specific side chain of L or D isomers of alanine, valine, leucine, isoleuciane, phenylalanine, tryptophan, methionine, glycine, serine, threonine, cysteine, tyrosine, asparagine, glutamine, aspartic acid, glutamic acid, lysine, arginine, proline and histidine;
n is 0 or 1;
W is —C(O)—;
m is an integer from 1 to 4;
$R^6$ is H, OH, —O—$C_1$-$C_{30}$ alkyl, —NH—$C_1$-$C_{30}$ alkyl, —S—$C_1$-$C_{30}$ alkyl, or —O—$C_2$-$C_{30}$ alkylenyl;
$R^4$ is a lipid of formula V:

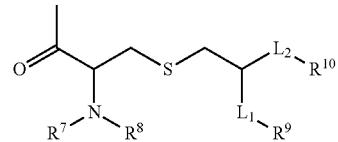

Formula V wherein:
$R^7$ and $R^8$ are independently from each other H, $C_1$-$C_{30}$ alkyl, $C_2$-$C_{30}$ alkylenyl, —C(O)—$C_1$-$C_{30}$ alkyl, —C(O)—$C_2$-$C_{30}$ alkylenyl, or —C(O)—O—$C_1$-$C_{30}$ alkyl;
$R^9$ is $C_1$-$C_{30}$ alkyl or $C_2$-$C_{30}$ alkylenyl;
$R^{10}$ is $C_1$-$C_{30}$ alkyl or $C_2$-$C_{30}$ alkylenyl;
$L_1$ is either absent, or —OC(O)—, 13 O—,—$NR^{11}$C(O)—,—OC(O)$NR^{11}$— or —$CH_2$ wherein $R^{11}$ is H, $C_1$-$C_{30}$ alkyl or $C_2$-$C_{30}$ alkylenyl;

$L_2$ is —CH$_2$OC(O)—, —CH$_2$O—, —CH$_2$NR$^{11}$C(O)— or —CH$_2$—, or if $L_1$ is absent, $L_2$ is —OC(O)—, —O—, —NR$^{11}$C(O)—, —NR$^{10}$R$^{11}$, —OC(O)NR$^{11}$— or —CH$_2$— wherein R$^{11}$ is as H, C$_1$-C$_{30}$alkyl or C$_2$-C$_{30}$alkylenyl.

2. The conjugated compound according to claim 1, wherein R$^2$ is a C$_1$-C$_6$alkylamino.

3. The conjugated compound according to claim 1, wherein —Z— is absent.

4. The conjugated compound according to claim 1, wherein —Z—R$^4$ is of Formula III, wherein n=1.

5. The conjugated compound according to claim 1, wherein —Z—R$^4$ is of Formula IV, wherein
m=1, 2, 3 or 4,
W is —C(O)—, and
R$^6$ is —OH, —O—C$_1$-C$_{30}$alkyl, or —NH—C$_1$C$_{30}$ alkyl.

6. The conjugated compound according to claim 1, wherein R$^4$ is a lipid of formula V:

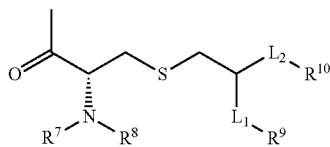

Formula V wherein:
R$^7$ and R$^8$ are independently from each other H or —C(O)—C$_1$-C$_{30}$alkyl;
R$^9$ and R$^{10}$ are independently from each other C$_1$-C$_{30}$alkyl; and
$L_1$ is absent and $L_2$ is —OC(O)—; or
$L_1$ is —OC(O)— and $L_2$ is —CH$_2$OC(O)—.

7. The conjugated compound according to claim 1, wherein:
R$^2$ is a C$_1$-C$_6$alkylamino,
X is a phenylene,
Z—R$^4$ is of Formula III, wherein:
n=0 or n=1 and R$^5$ is the specific side chain of L or D isormers of alanine, valine, leucine, isoleucine, phenylalanine, tryptophan, methionine, glycine, serince, threonine, cysteine, tyrosine, asparagine, glutamine, aspartic acid, glutamic acid, lysine, arginine, proline and histidine R$^4$ is a lipid of Formula V, wherein:
R$^7$ and R$^8$ are both a hydrogen atom,
R$^9$ and R$^{10}$ are independently from each other C$_1$-C$_{30}$alkyl; and
$L_1$ is absent and $L_2$ is —OC(O)—; or
$L_1$ is —OC(O)— and $L_2$ is —CH$_2$OC(O)—.

8. The conjugated compound according to claim 1, wherein said compound is selected from the group consisting of:
(R)-3-(2-amino-3-(4-((6-amino-2-(butylamino)-8-hydroxy-9H-purin-9-yl)methyl)phenyl amino)-3-oxopropylthio)propane-1,2-diyl dipalmitate,
3-((R)-2-amino-3-((S)-1-(4-((6-amino-2-(butylamino)-8-hydroxy-9H-purin-9-yl)methyl)phenylamino)-3-hydroxy-1-oxopropan-2-ylamino)-3-oxopropylthio)propane-1,2-diyl dipalmitate,
(R)-3-(3-(4-((6-amino-2-(butylamino)-8-hydroxy-9H-purin-9-yl)methyl)phenylamino)-3-oxo-2-palmitamidopropylthio)propane-1,2-diyl dipalmitate,
(R)-2-(2-amino-3-(4-((6-amino-2-(butylamino)-8-hydroxy-9H-purin-9yl)methyl)phenylamino)-3-oxopropylthio)ethyl tetradecanoate,
(R)-2-(2-amino-3-(4-((6-amino-2-(butylamino)-8-hydroxy-9H-purin-9yl)methyl)phenylamino)-3-oxopropylthio)ethyl palmitate,
(R)-2-(2-amino-3-(4-((6-amino-2-(butylamino)-8-hydroxy-9H-purin-9yl)methyl)phenylamino)-3-oxopropylthio)ethyl stearate,
2-((S)-2-amino-3-((S)-1-(4-((6-amino-2-(butylamino)-8-hydroxy-9H-purin-9-yl)methyl)phenylamino)-3-hydroxy-1-oxopropan-2-ylamino)-3-oxopropylthio)ethyl tetradecanoate,
2-((S)-2-amino-3-((S)-1-(4-((6-amino-2-(butylamino)-8-hydroxy-9H-purin-9-yl)methyl)phenylamino)-3-hydroxy-1-oxopropan-2-ylamino)-3-oxopropylthio)ethyl palmitate,
2-((S)-2-amino-3-((S)-1-(4-((6-amino-2-(butylamino)-8-hydroxy-9H-purin-9-yl)methyl)phenylamino)-3-hydroxy-1-oxopropan-2-ylamino)-3-oxopropylthio)ethyl stearate,
2-((R)-2-amino-3-((S)-5-(4-((6-amino-2-(butylamino)-8-hydroxy-9H-purin-9-yl)methyl)phenylamino)-1-methoxy-1,5-dioxopentan-2-ylamino)-3-oxopropylthio)ethyl tetradecanoate, and
a tautomer thereof or a pharmaceutically acceptable salt, solvate or polymorph of said compound or tautomer.

9. A pharmaceutical composition comprising the conjugated compound according to claim 1 and a pharmaceutically acceptable excipient or carrier.

10. A vaccine comprising the conjugated compound according to claim 1.

* * * * *